US012558240B2

(12) United States Patent
Mendelsohn et al.

(10) Patent No.: US 12,558,240 B2
(45) Date of Patent: Feb. 24, 2026

(54) AORTIC ARCH BARORECEPTOR IMPLANTS FOR TREATMENT OF HYPERTENSION

(71) Applicant: ARCHimedes Vascular, LLC, Birmingham, AL (US)

(72) Inventors: Farrell O. Mendelsohn, Birmingham, AL (US); Craig Bonsignore, Scottsdale, AZ (US)

(73) Assignee: ARCHimedes Vascular, Inc., Birmingham, AL (US)

( * ) Notice: Subject to any disclaimer, the term of this patent is extended or adjusted under 35 U.S.C. 154(b) by 0 days.

(21) Appl. No.: 18/929,399

(22) Filed: Oct. 28, 2024

(65) Prior Publication Data

US 2025/0049557 A1     Feb. 13, 2025

Related U.S. Application Data

(63) Continuation-in-part of application No. PCT/US2023/020612, filed on May 1, 2023.
(Continued)

(51) Int. Cl.
*A61F 2/856*     (2013.01)
*A61F 2/06*     (2013.01)
*A61F 2/90*     (2013.01)

(52) U.S. Cl.
CPC ................ *A61F 2/856* (2013.01); *A61F 2/06* (2013.01); *A61F 2002/061* (2013.01);
(Continued)

(58) Field of Classification Search
CPC ................ A61F 2/82–945; A61F 2/954; A61F 2230/0008; A61F 2230/0017–0026
See application file for complete search history.

(56) References Cited

U.S. PATENT DOCUMENTS

| | | | |
|---|---|---|---|
| 5,104,404 | A | 4/1992 | Wolff |
| 5,755,781 | A | 5/1998 | Jayaraman |

(Continued)

FOREIGN PATENT DOCUMENTS

| | | |
|---|---|---|
| CN | 109009562 A | 12/2018 |
| DE | 19611755 A1 | 2/1998 |

(Continued)

OTHER PUBLICATIONS

Abraham, "The Structure of Baroreceptors in Pathological Conditions in Man", Baroreceptors and Hypertension, 1967, pp. 273-291.
(Continued)

*Primary Examiner* — Rebecca S Preston
(74) *Attorney, Agent, or Firm* — Gordon Rees Scully & Mansukhani, LLP

(57) ABSTRACT

Implant devices for hypertension and methods of treatment are provided. Implant devices are configured for placement in a target region of an aortic arch of the patient, thereby engaging arterial walls in the target region sufficiently to stretch and/or tension arterial walls, thereby inducing the baroreflex response. Such implants can include one or more expandable structures configured to engage an elongated target region in the aortic arch. The target region can extend along a majority of the aortic arch including a cylindrical segment of aortic arch between the left common carotid artery and the left subclavian artery. An elongated target zone can further extend at least between the brachiocephalic artery takeoff and the left subclavian artery takeoff. Such embodiments can utilize one or more expandable structures with a non-circular cross-section that stretch and reshape the arterial walls to induce tension in the arterial walls, thereby generating a robust baroreflex response.

10 Claims, 54 Drawing Sheets

Related U.S. Application Data

(60) Provisional application No. 63/657,565, filed on Jun. 7, 2024, provisional application No. 63/594,903, filed on Oct. 31, 2023, provisional application No. 63/443,656, filed on Feb. 6, 2023, provisional application No. 63/336,818, filed on Apr. 29, 2022.

(52) U.S. Cl.
  CPC ........... *A61F 2002/068* (2013.01); *A61F 2/90* (2013.01); *A61F 2210/0014* (2013.01); *A61F 2230/0008* (2013.01); *A61F 2230/0017* (2013.01); *A61F 2250/0039* (2013.01)

(56) References Cited

U.S. PATENT DOCUMENTS

| | | | |
|---|---|---|---|
| 6,875,228 | B2 | 4/2005 | Pinchasik et al. |
| 8,257,430 | B2 | 9/2012 | Mead |
| 8,454,677 | B2 * | 6/2013 | Fischell ................... A61F 2/915 |
| | | | 623/1.34 |
| 8,663,541 | B2 | 3/2014 | Chun et al. |
| 8,923,972 | B2 | 12/2014 | Gross |
| 9,125,567 | B2 | 9/2015 | Gross et al. |
| 9,125,732 | B2 | 9/2015 | Gross et al. |
| 9,402,751 | B2 | 8/2016 | Zukowski |
| 9,457,174 | B2 | 10/2016 | Gross |
| 9,550,048 | B2 | 1/2017 | Gross |
| 9,592,136 | B2 | 3/2017 | Gross et al. |
| 9,642,726 | B2 | 5/2017 | Gross et al. |
| 10,279,184 | B2 | 5/2019 | Pierce et al. |
| 10,384,043 | B2 | 8/2019 | Gross et al. |
| 10,588,763 | B2 | 3/2020 | Kassab et al. |
| 10,653,513 | B2 | 5/2020 | Seybold et al. |
| 10,779,965 | B2 | 9/2020 | Dagan et al. |
| 10,786,372 | B2 | 9/2020 | Yeh et al. |
| 2003/0093142 | A1 | 5/2003 | Edelman et al. |
| 2006/0149353 | A1 | 7/2006 | Schatz et al. |
| 2007/0005127 | A1 | 1/2007 | Boekstegers et al. |
| 2008/0177350 | A1 | 7/2008 | Kieval et al. |
| 2010/0042202 | A1 | 2/2010 | Ramzipoor et al. |
| 2010/0179614 | A1 | 7/2010 | Kieval et al. |
| 2011/0077729 | A1 | 3/2011 | Gross et al. |
| 2011/0230957 | A1 | 9/2011 | Bonsignore et al. |
| 2012/0232613 | A1 | 9/2012 | Kieval et al. |
| 2013/0304102 | A1 | 11/2013 | Gross et al. |
| 2013/0338748 | A1 | 12/2013 | Dagan |
| 2015/0073533 | A1 | 3/2015 | Kassab et al. |
| 2016/0303381 | A1 | 10/2016 | Pierce et al. |
| 2017/0135829 | A1 | 5/2017 | Gross et al. |
| 2017/0196713 | A1 | 7/2017 | Gross et al. |
| 2017/0304042 | A1 | 10/2017 | Ren |
| 2018/0235745 | A1 | 8/2018 | Seybold et al. |
| 2019/0224484 | A1 | 7/2019 | Pierce et al. |
| 2019/0247050 | A1 | 8/2019 | Goldsmith |
| 2020/0384248 | A1 | 12/2020 | Gross et al. |
| 2021/0007837 | A1 * | 1/2021 | Haldis ........................ A61F 2/90 |
| 2021/0077283 | A1 | 3/2021 | Yeh et al. |
| 2022/0183865 | A1 * | 6/2022 | Gifford, III .............. A61F 2/90 |
| 2022/0257279 | A1 * | 8/2022 | Deaton .................. A61B 50/20 |

FOREIGN PATENT DOCUMENTS

| | | |
|---|---|---|
| EP | 0828461 A1 | 3/1998 |
| EP | 1006938 A1 | 6/2000 |
| EP | 2471491 A2 | 7/2012 |
| WO | 2009118912 A1 | 10/2009 |
| WO | 2020214110 A1 | 10/2020 |

OTHER PUBLICATIONS

Armour, "Physiological Behavior of Thoracic Cardiovascular Receptors", American Journal of Physiology, vol. 225, No. 1, Jul. 1973, pp. 177-185.

Aumonier, "Histological Observations on the Distribution of Baroreceptors in the Carotid and Aortic Regions of the Rabbit, Cat and Dog", Acta Anatomica, vol. 82, No. 1, 1972, pp. 1-16.

Benson et al., "Aortic Arch Baroreceptor Stimulation in an Experimental Goat Model: A Novel Method to Lower Blood Pressure", Frontiers in Cardiovascular Medicine, vol. 5, No. 193, Jan. 15, 2019, 7 pages.

Bergwerff et al., "Unique Vascular Morphology of the Fourth Aortic Arches: Possible Implications for Pathogenesis of Type-B Aortic Arch Interruption and Anomalous Right Subclavian Artery", Cardiovascular Research, vol. 44, No. 1, Oct. 1999, pp. 185-196.

Daly et al., "The Localisation of Receptors Involved in the Reflex Regulation of the Heart Rate", From the Institute of Physiology, Cardiff, and the Laboratories of the Medical Unit, University College Hospital Medical School, London, pp. 330-340.

Donald et al., "Comparison of Aortic and Carotid Baroreflexes in the Dog", J. Physiol., 215, pp. 521-538.

Hauss et al., "Uber die Reizung der Pressorezeptoren im Sinus Caroticus Beim Hund", Zeitschrift fur Kreislaufforschung, vol. 38, 1949, pp. 28-33.

Kember et al., "Mechanism of Smart Baroreception in the Aortic Arch", Physical Review E: Statistical, Nonlinear, and Soft Matter Physics, vol. 74, Sep. 2006, 5 pages.

Krauhs, "Structure of Rat Aortic Baroreceptors and Their Relationship to Connective Tissue", Journal of Neurocytology, vol. 8, Aug. 1979, pp. 401-414.

Lau et al., "Aortic Baroreceptors Display Higher Mechanosensitivity Than Carotid Baroreceptors", Frontiers in Physiology, vol. 7, No. 384, Aug. 31, 2016, 8 pages.

Lauder et al., "Device-Based Therapies for Arterial Hypertension", Nature Reviews Cardiology, vol. 17, Oct. 2020, pp. 614-628.

Mahfoud et al., "Device Therapy of Hypertension", Circulation Research, vol. 128, No. 7, Apr. 2, 2021, pp. 1080-1099.

Mendelowitz et al., "Pulsatile Sinus Pressure Changes Evoke Sustained Baroreflex Responses in Awake Dogs", American Journal of Physiology, vol. 255, Sep. 1988, pp. H673-H678.

Min et al., "Arterial Baroreceptors Sense Blood Pressure Through Decorated Aortic Claws", Supplemental Information, Cell Reports, vol. 29, No. 8, Nov. 19, 2019, 11 pages.

Min et al., "Arterial Baroreceptors Sense Blood Pressure Through Decorated Aortic Claws", Cell Reports, vol. 29, No. 8, Nov. 19, 2019, pp. 2192-2201.e3.

Sanders et al., "Arterial baroreflex control of sympathetic nerve activity during elevation of blood pressure in normal man: dominance of aortic baroreflexes", Pathophysiology and Natural History—Hypertension, vol. 77, No. 2, Feb. 1988, pp. 279-288.

Spiering et al., "Endovascular Baroreflex Amplification for Resistant Hypertension: A Safety and Proof-of-Principle Clinical Study", Lancet, vol. 390, No. 10113, Dec. 16, 2017, pp. 2655-2661.

Sutton et al., "Archives of Internal Medicine", Pain, vol. 45, No. 6, 1930, pp. 827-867.

Van Kleef et al., "Endovascular baroreflex amplification and the effect on sympathetic nerve activity in patients with resistant hypertension: A proof-of-principle study", PLoS ONE 16(11): e0259826, Nov. 16, 2021, 1-14.

Zangirolami et al., "Ortner's Syndrome: Secondary Laryngeal Paralysis Caused by a Great Thoracic Aorta Aneurysm", International Archives of Otorhinolaryngology, vol. 19, No. 2, Apr. 2015, pp. 180-182.

* cited by examiner

Right common carotid artery

Left common carotid artery

Right subclavian artery

Left subclavian artery

Left Aortic Arch

T

Ascending aorta

Descending aorta

⊘ 3ʳᵈ Pharyngeal arch artery
◔ 4ᵗʰ Pharyngeal arch artery    ⊘ Aortic sac
◯ 6ᵗʰ Pharyngeal arch artery    ◓ Truncus arteriosus
⊕ 7ᵗʰ Intersegmental artery    ◎ Dorsal aorta

R4PA—  —L4PA

⊘ 3ʳᵈ Pharyngeal arch artery
◌ 4ᵗʰ Pharyngeal arch artery  ⊘ Aortic sac
⊙ 6ᵗʰ Pharyngeal arch artery  ◌ Truncus arteriosus
⊕ 7ᵗʰ Intersegmental artery  ◌ Dorsal aorta Histology from
Target Region
(Section B in Fig. 14C)

Histology from
adjacent region
(Section C in Fig. 14C)

Baroreceptor nerve fibers stained pink are located on out

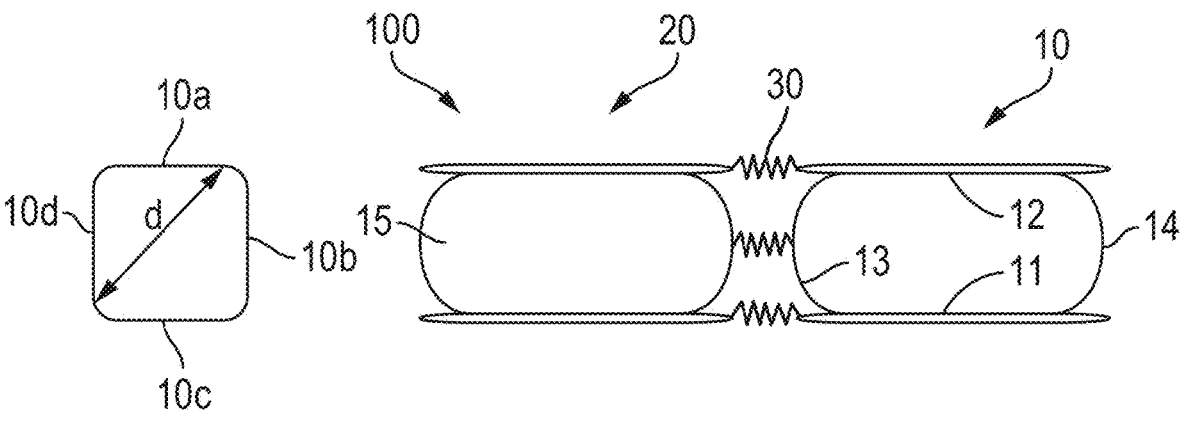
FIG. 10A                    FIG. 10B
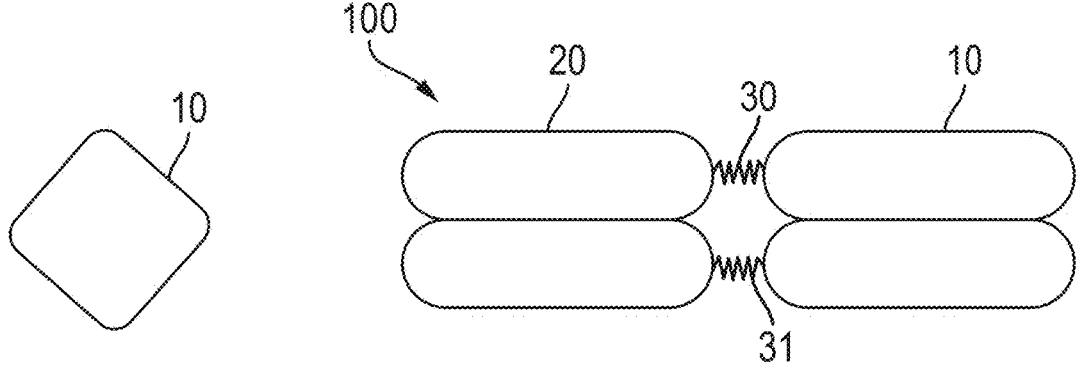
FIG. 10C                    FIG. 10D

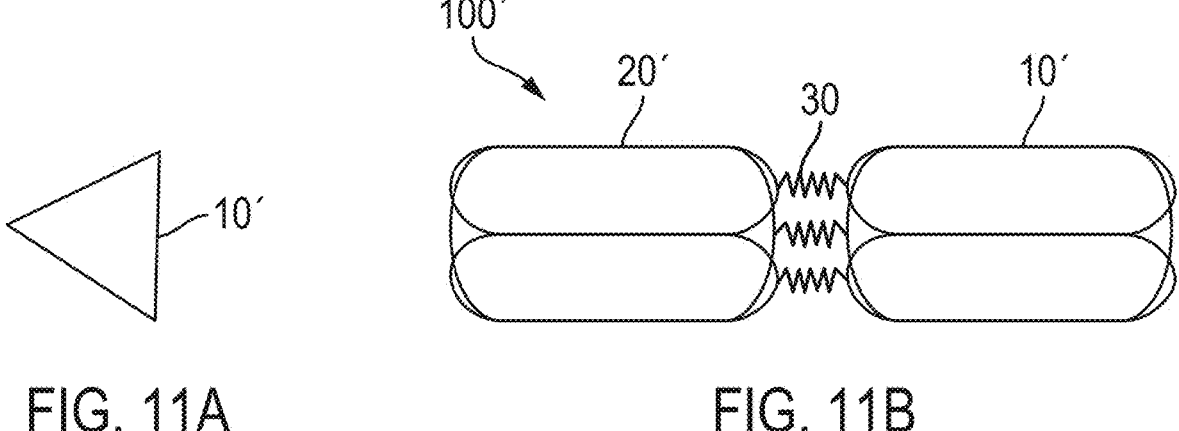
FIG. 11A                    FIG. 11B
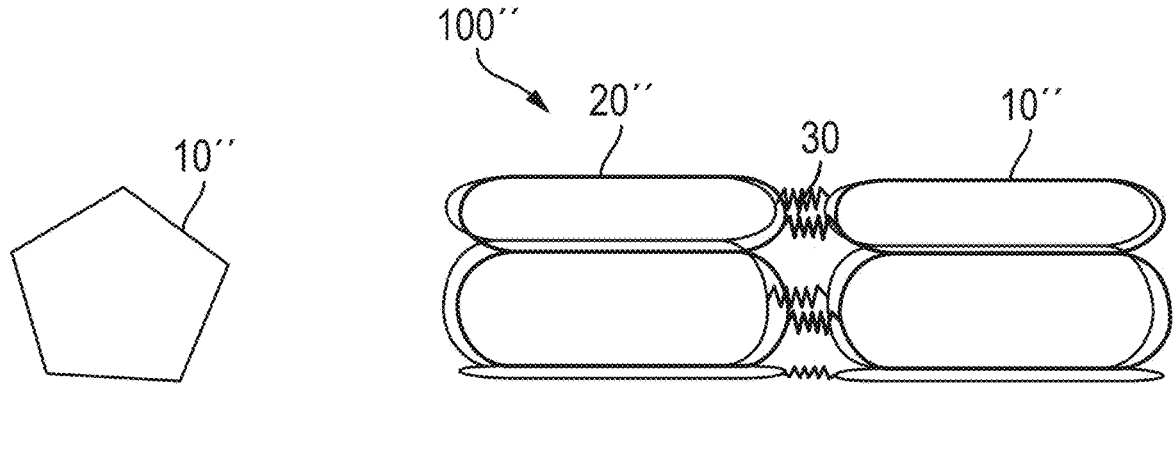
FIG. 12A                    FIG. 12B Aortic Arc Length (E)

Aortic Arch Diameters (A, B, C, D)

A = ascending aorta
B = brachiocephalic region
C = proximal arch
D = left common carotid region
E = distal arch
F = left subclavian region
G = descending aorta

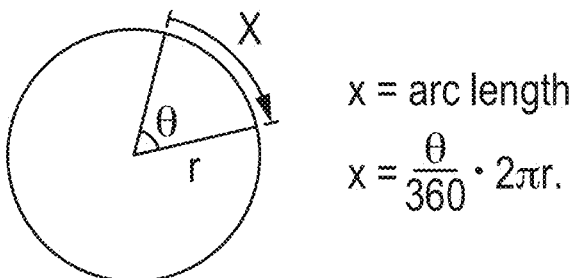
x = arc length
$$x = \frac{\theta}{360} \cdot 2\pi r.$$
FIG. 15A
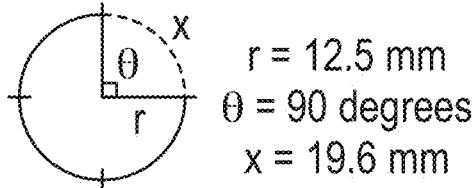
r = 12.5 mm
$\theta$ = 90 degrees
x = 19.6 mm
FIG. 15B
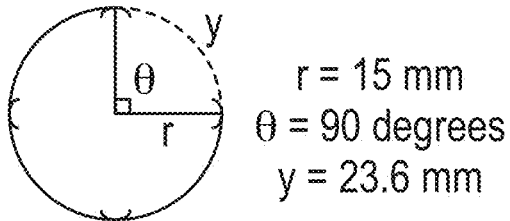
r = 15 mm
$\theta$ = 90 degrees
y = 23.6 mm
FIG. 15C
FIG. 15D
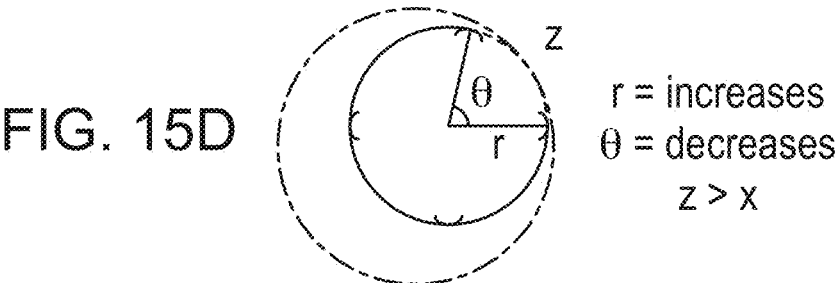
r = increases
$\theta$ = decreases
z > x Deploying an implant comprising one or more expandable structures to engage a target region in the aortic arch comprising a cylindrical segment of aortic arch between the LCCA and LSA Stretching, with struts of the implants, an arterial wall along target region of the aortic arch by at least 20%, thereby inducing a baroflex response that reduces blood pressure Exposing the target region being stretched to pulsatile blood flow through a major opening between the struts of the implant, thereby providing long term reduction in blood pressure

FIG. 19

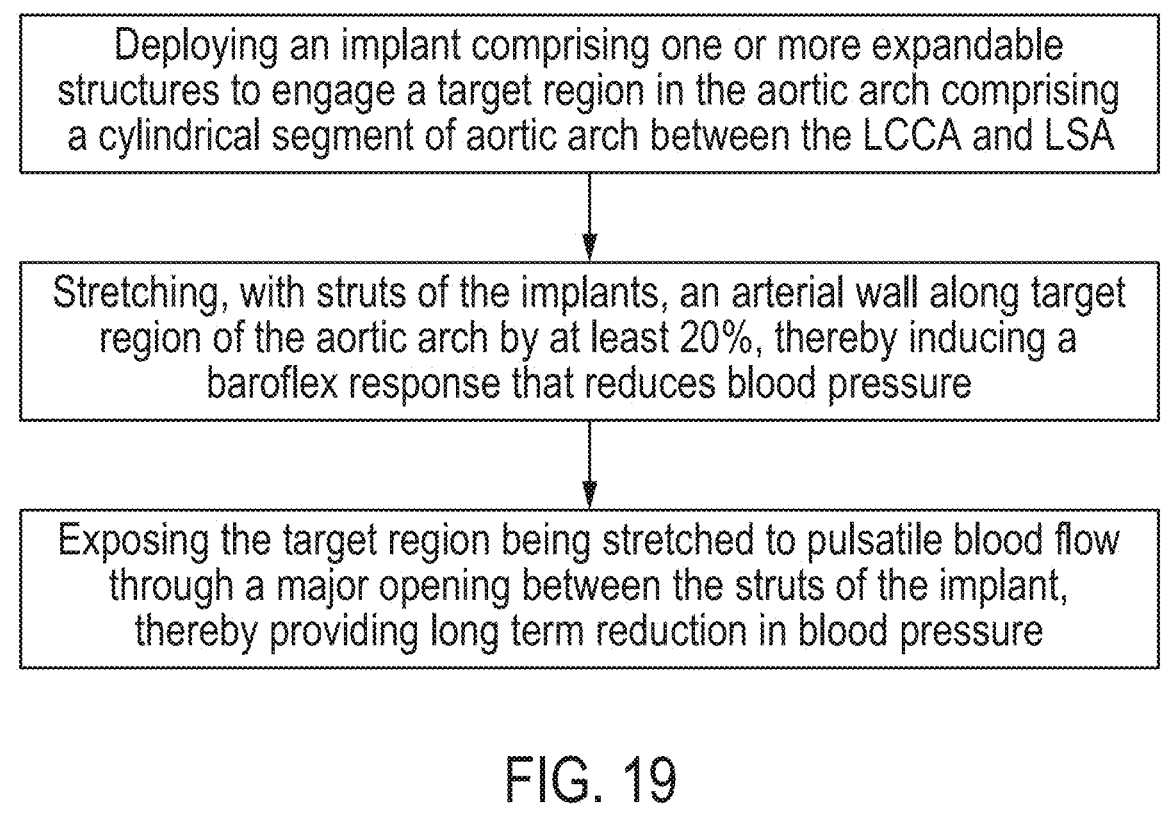

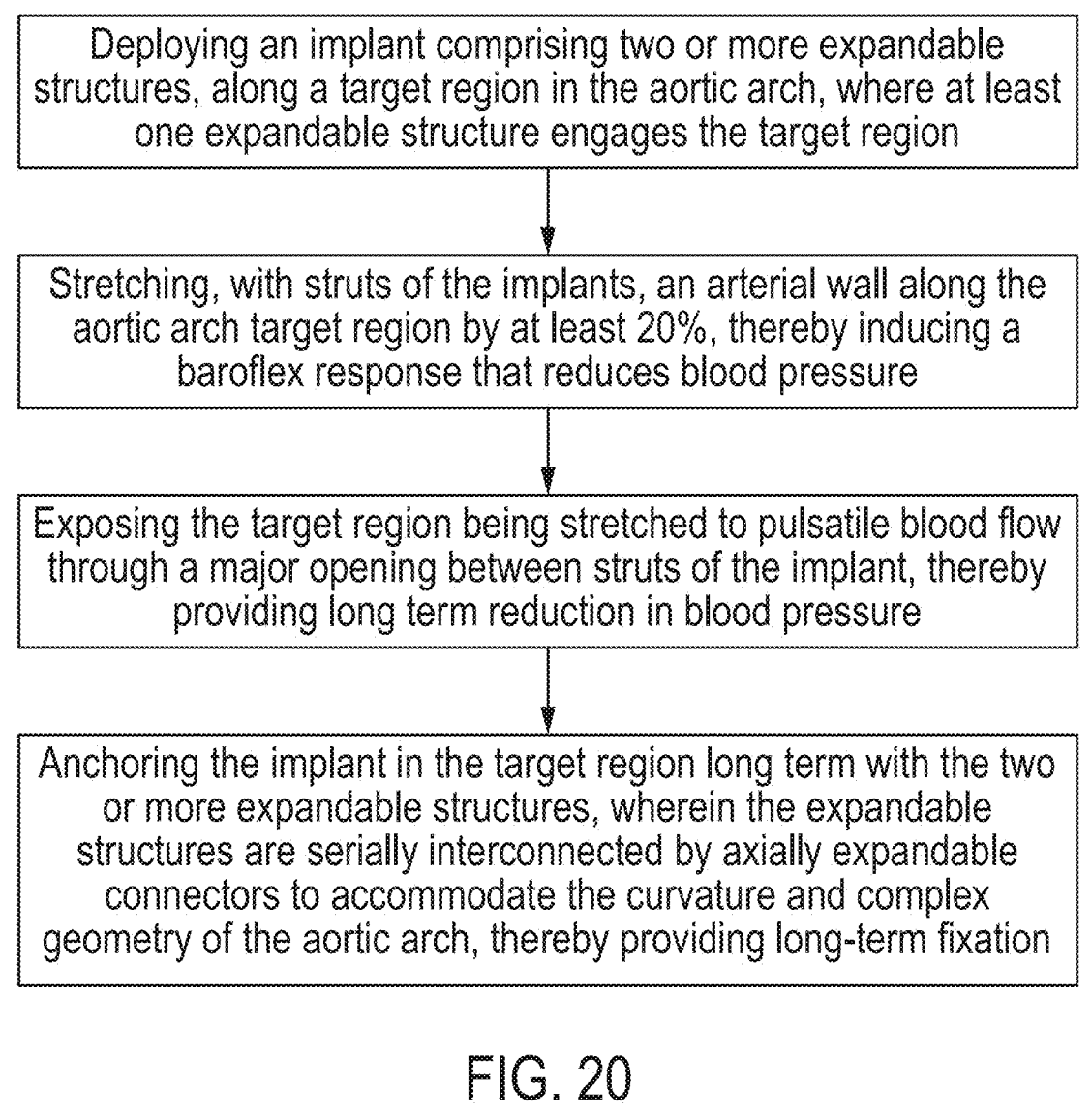

Deploying an implant comprising two or more expandable structures, along a target region in the aortic arch, where at least one expandable structure engages the target region Stretching, with struts of the implants, an arterial wall along the aortic arch target region by at least 20%, thereby inducing a baroflex response that reduces blood pressure Exposing the target region being stretched to pulsatile blood flow through a major opening between struts of the implant, thereby providing long term reduction in blood pressure Anchoring the implant in the target region long term with the two or more expandable structures, wherein the expandable structures are serially interconnected by axially expandable connectors to accommodate the curvature and complex geometry of the aortic arch, thereby providing long-term fixation

FIG. 20

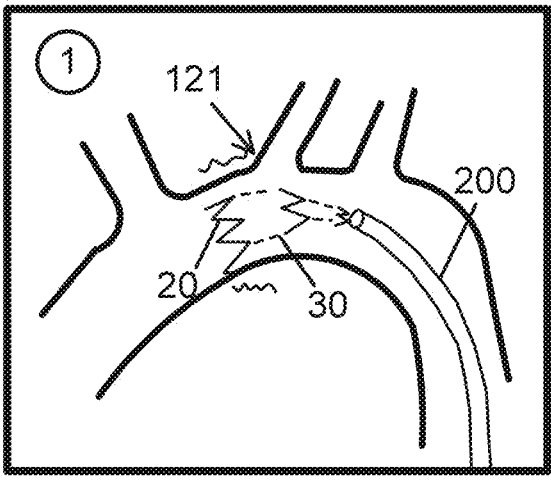
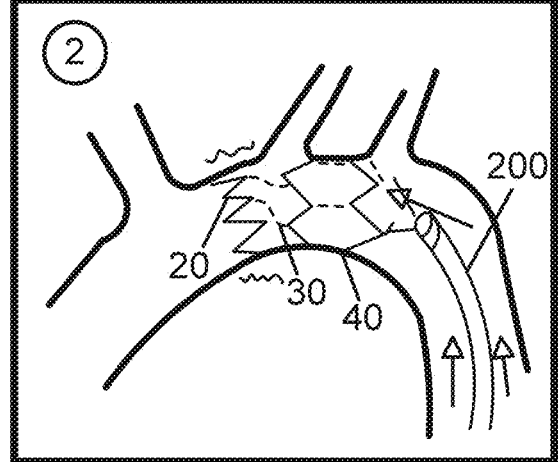
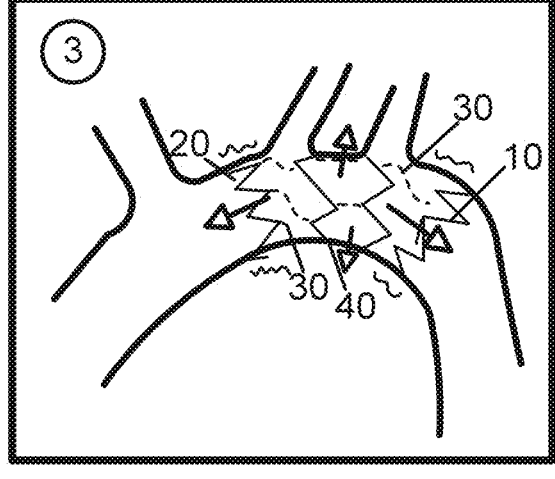
FIG. 26

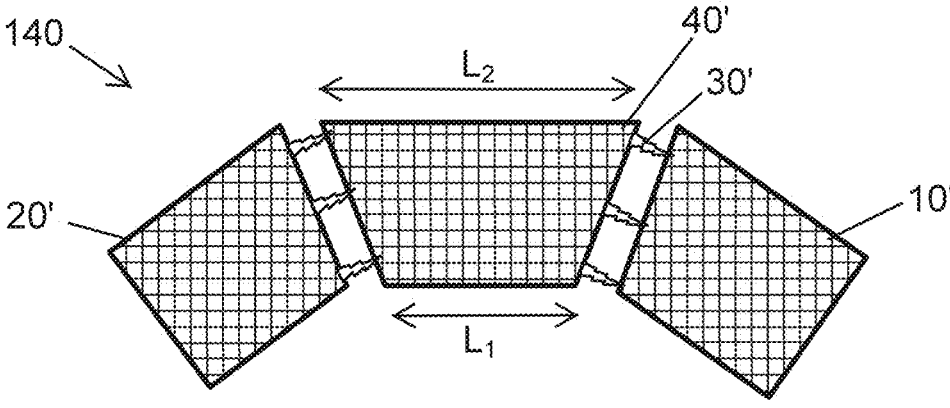
FIG. 27
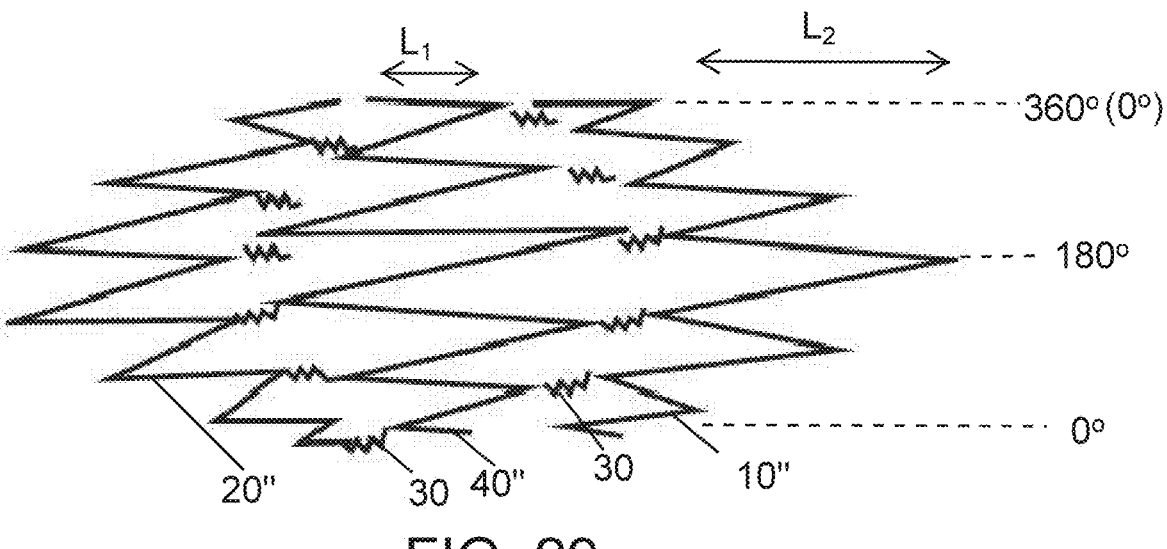
FIG. 28
FIG. 29

P1          P0          P1' option
1 option
2

140

140

150

150a

150

150a

151

152

ECG

BP (mm Hg)

Typical BP
(mm Hg)

target zone

A = ascending aorta
B = brachiocephalic region
C = proximal arch
D = left common carotid region
E = distal arch
F = left subclavian region
G = descending aorta

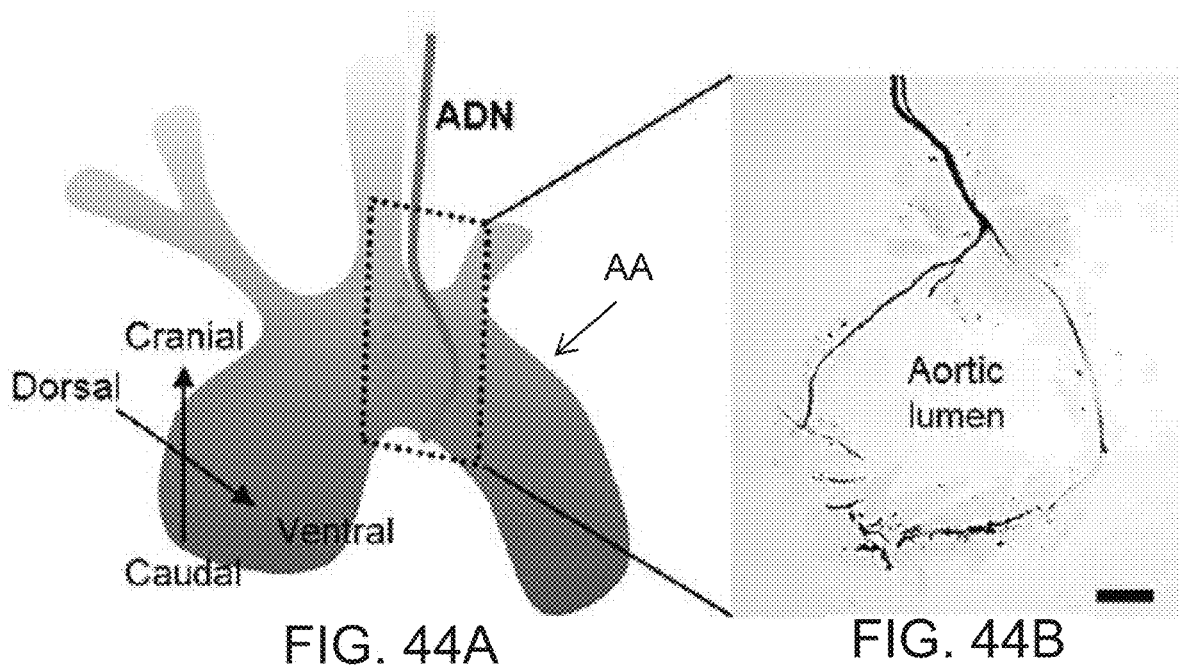
FIG. 44A                    FIG. 44B

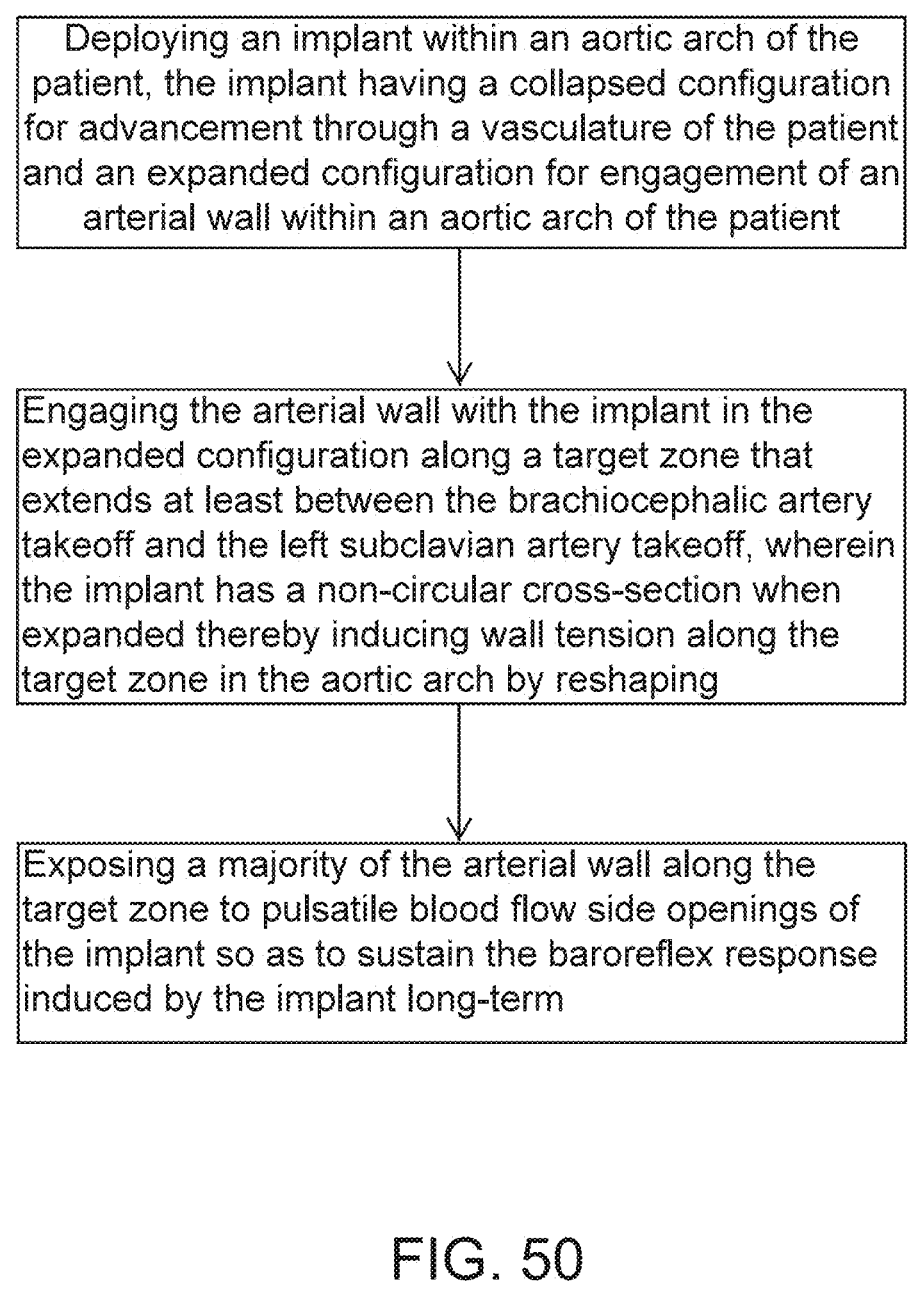

Deploying an implant within an aortic arch of the patient, the implant having a collapsed configuration for advancement through a vasculature of the patient and an expanded configuration for engagement of an arterial wall within an aortic arch of the patient Engaging the arterial wall with the implant in the expanded configuration along a target zone that extends at least between the brachiocephalic artery takeoff and the left subclavian artery takeoff, wherein the implant has a non-circular cross-section when expanded thereby inducing wall tension along the target zone in the aortic arch by reshaping Exposing a majority of the arterial wall along the target zone to pulsatile blood flow side openings of the implant so as to sustain the baroreflex response induced by the implant long-term

FIG. 50

AORTIC ARCH BARORECEPTOR IMPLANTS FOR TREATMENT OF HYPERTENSION

CROSS-REFERENCES TO RELATED APPLICATIONS

The present application is a Non-Provisional of and claims the benefit of priority of U.S. Provisional Appln. Nos. 63/594,903 filed Oct. 31, 2023 and 63/657,565 filed Jun. 7, 2024; and is a continuation-in-part of PCT Appln. No. PCT/US2023/020612 filed May 1, 2023, which claims the benefit of priority of U.S. Provisional Appln. No. 63/336, 818 filed Apr. 29, 2022 and 63/443,656 filed Feb. 6, 2023, the disclosures which are incorporated herein by reference in their entirety for all purposes.

This application is generally related to commonly-owned applications: PCT Patent Appln. No. PCT/US2023/020608 filed May 1, 2023, entitled "Delivery Catheter and Methods of Delivery for Aortic Arch Baroreceptor Hypertension Implants"; U.S. Non-Provisional application Ser. No. 18/929,165 filed concurrently herewith (Oct. 28, 2024), entitled "Delivery Catheter and Methods of Delivery for Aortic Arch Baroreceptor Hypertension Implants,"; and PCT Appln. No. PCT/US2024/016200 filed Feb. 16, 2024, entitled "Baroreflex Gauge and Mapping Device and Methods of Use"; the contents which are also incorporated herein by reference in their entireties for all purposes.

FIELD OF THE INVENTION

In one aspect, the invention pertains to implantable devices for treatment of hypertension, as well as associated components, systems and methods.

BACKGROUND OF THE INVENTION

Hypertension affects one of every two adults in the United States. Yet only 24% of patients have their blood pressure adequately controlled. Hypertension is the leading preventable cause of heart attack, stroke and death. However, a 10 mm Hg drop in blood pressure lowers this cardiovascular risk by 20%.

Pharmacologic therapy has been the mainstay of hypertension treatment for decades, despite the documented poor medical compliance of patients to their antihypertensive medical regimens. In 2004, the landmark trial for a catheter-based medical device (i.e., Symplicity 1) first demonstrated the blood pressure lowering effect of renal denervation by a radiofrequency ablation catheter. Findings from additional clinical trials of renal denervation with radiofrequency and ultrasound energy (i.e., the SPYRAL and RADIANCE trials, respectively) have confirmed these findings, albeit with more modest blood pressure lowering results on the order of 5-10 mm Hg drops in ambulatory recorded systolic blood pressure.

An endovascular implant developed by Vascular Dynamics for hypertension, relied on an expandable device inserted into the carotid artery that lowered blood pressure, it was thought, by stretching the artery wall from the inside and augmenting the carotid baroreflex. In a 2017 study, this carotid baroreflex modulating device lowered ambulatory recorded systolic blood pressure considerably, over twice what had been reported in the renal denervation trials. While clinical results initially appeared promising, with several patients reporting dramatic blood pressure lowering persisting two to three years, clinical outcomes were mixed as some patients suffered transient ischemic attacks (TIA), hindering further trials and subsequent development.

Another challenge arose in regard to deploying the device in the carotid sinus, which was the primary target of the device. Since the carotid sinus carries blood to the brain, any difficulties encountered in this area, for example trauma to arterial tissues during deployment, subsequent dislodgement of the device and/or accumulation of plaques in the region due to the device or trauma, may contribute to TIA or strokes, resulting in adverse or fatal patient outcomes. For clinicians that lack experience with this sensitive region, for example, placing carotid stents, performing procedures in this area may present unnecessary risks to the patient.

Additional devices have been developed specifically to stretch arterial walls at discrete targeted locations including particular locations in the carotid and the aorta, however, clinical study results so far have indicated such approaches remain lacking or inconsistent results and fail to lower blood pressure appreciably (e.g. greater than 10 mm Hg, preferably about 20 mmHg).

Thus, there is a continuing need for hypertension treatment devices and methods that provide a reliable and robust therapeutic response utilizing the baroreflex response, yet avoid the considerable drawbacks associated with conventional approaches described above. There is further need for such devices that allow for improved case and consistency of implantation in order to avoid the noted adverse effects, allow for implantation for a wide variety of clinicians and more reliably provide positive patient outcomes to reduce hypertension long term.

BRIEF SUMMARY OF THE INVENTION

The invention relates to an implantable hypertension treatment device for deployment within the aortic arch and associated methods of treatment.

In one aspect, the invention pertains to a method for treating hypertension in a patient. Such methods can include steps of: deploying an implant within the aortic arch of the patient, where the implant includes multiple expandable structures interconnected by angled or helically oriented bridges, where each of the plurality of expandable structure has an expanded configuration and a collapsed configuration. In the collapsed configuration, the implant is advanceable through the vasculature and, in the expanded configuration, the implant engages an arterial wall of the aortic arch. The method further entails stretching and preferably changing a shape of at least a portion of the arterial wall along a target region. In some embodiments, the target region includes a cylindrical segment that wraps around the aortic arch (particularly along an inner curvature) by engagement of one of the expandable structures, thereby triggering a baroreflex response of baroreceptors within the target region and exposing a majority of the arterial wall along the target region to pulsatile blood flow through one or more major openings of the implant so as to sustain the baroreflex response induced by the implant long-term. In some embodiments, the portion of the arterial wall is stretched preferably by at least 10%, typically at least 20%, and preferably reshaping. In some embodiments, the portion of the arterial wall is reshaped to an oblong or oval shape. In some embodiments, the target region includes the entire cylindrical strip of the aorta between the left common carotid artery and the left subclavian artery. Preferably, the implant extends beyond the target zone in both directions to ensure optimal engagement throughout the target region.

In another aspect, the invention pertains to an implant device for treating hypertension in a patient. Such implants can include one or more expandable structures interconnected serially by bridge members, the expandable structures having a collapsed configuration for advancement through a vasculature of the patient and an expanded configuration for engagement of an arterial wall within the aorta of the patient. In some embodiments, each of the expandable structures is formed of one or more wires formed in an expandable design (e.g., one or more Nitinol wires formed in a meandering, sinusoidal or zig-zag design to form a circumferential ring or band). In some embodiments, each expandable structure is defined by a single continuous wire. In some embodiments, each expandable structure is a laser cut design in a single tube or a plurality of wires (e.g. 12, 24, 35, 48, etc.). In some embodiments, the bridge members between adjacent expandable structures are angled or helically oriented to allow the implant to better accommodate the curvature of the aortic arch. In some embodiments, each expandable structure comprises an expandable ring (e.g., sinusoidal or zig-zag pattern with peaks and valleys). In some embodiments, the entire implant with multiple expandable structures and flexible connectors can be defined by a laser cut design of a single tube. In such wire or laser cut embodiments, the expandable structure can have a substantially circular cross-section. In some embodiments, each of the expandable structures include multiple elongated frames, each frame having a pair of struts that define opposing lateral sides and are spaced apart to define a major opening therebetween, where the frames are interconnected along adjacent lateral sides so as to form a regular polygonal cross-section. As used herein, "frame" can refer to "cells" or any similar such structure.

In some embodiments, the implant includes two expandable structures interconnected by flexible bridge members to accommodate the curvature of the arch. In some embodiments, the implant includes three expandable structures where the middle expandable structure is disposed at the target location to activate the baroreceptor nerves and the proximal and the proximal and distal expandable structures act as anchors to secure the middle structure at the target location. In such embodiments, the expandable structures can be of the same or differing dimensions. In some embodiments, the implant includes three expandable structures where the middle structure has a lateral dimension that is larger (e.g., 1.3-1.5 times) than the lateral dimension of the proximal and distal expandable structures. This approach allows for even more stretch (e.g., 10%, 20%, 30% or more) along the target region since the proximal and distal structures help transition the arterial walls and inhibit tearing or dissection of the stretched vasculature. It is further desirable to reshape the artery with the implant, as will be discuss in further detail below. In some embodiments, the implant or the one or more expandable structures of the implant have a variable diameter or flared shape. In some embodiments, the implant includes one or more barbs to facilitate long term anchoring. At least one of the expandable structures is dimensioned so that when expanded within a target region of the aortic arch, the pair of struts of a respective frame stretch arterial tissues in the target region sufficiently to induce a baroreflex response of baroreceptors in the target region, such as by 10% or more, typically 20% or more and/or reshape the arterial walls to impart wall tension, while a major opening between the struts exposes the arterial wall of the target region to pulsatile blood flow to sustain the baroreflex response long-term. It is appreciated that the expandable structures can be any described herein (e.g., joined frames, continuous wire, laser cut).

In some embodiments, the implant includes one or more proximally extending tethers by which the implant can be retracted by a tool or delivery sheath for removal or repositioning. The tethers can include proximal connectors thereon that releasably attach to a retention collar of a delivery tool or catheter. In such embodiments, the implant can be used to gauge a baroreflex response and the position of the implant can be adjusted based on the response.

In one aspect, the invention pertains to an implant for treating hypertension in a patient. The implant has a collapsed configuration for advancement through a vasculature of the patient and an expanded configuration for engagement of an arterial wall within an aortic arch of the patient. The implant can include one or more expandable structures. In some embodiments, the implant has a total length of at least 60 mm such that, when deployed in the aortic arch, the implant extends along a target zone that extends at least between the brachiocephalic artery takeoff and the left subclavian artery takeoff. In some embodiments, the implant has a non-circular cross-section, when expanded, along its entire length so as to induce wall tension along entire zone of the aortic arch thereby inducing a baroreflex response of baroreceptors in the target zone. The implant has sufficient flexibility to accommodate a curvature of the aortic arch along the elongated zone. In some embodiments, any side openings in the implant are sufficiently large to allow lateral blood flow therethrough to any side branches in the aortic arch and to expose arterial walls to pulsatile blood flow to maintain a long-term response.

In some embodiments, the implant has an elliptical, oval or pill-shaped cross section. In some embodiments, the non-circular cross-section is a regular polygonal shape. In some embodiments, the non-circular cross-section is constant along the entire length of the implant. In some embodiments, the non-circular cross-section is variable (e.g. increasing/decreasing or tapering) along a length of the implant. In some embodiments, a greatest lateral dimension of the implant is greater than 25 mm. In some embodiments, a greatest lateral dimension of the implant is between 40-60 mm. In some embodiments, a total length of the implant is about 60 mm or greater, typically between 70-90 mm. In some embodiments, the implant is self-expandable. In some embodiments, the implant is a woven or braided from one or more wires. Typically, the implant is formed of Nitinol. In some embodiments, the implant is formed from a laser cut tube. In some embodiments, when expanded, the implant design is such that interstitial openings have sufficient area, such as at least 9 mm$^2$, typically within a range of 9-30 mm$^2$ to allow blood flow therethrough and expose arterial walls to pulsatile blood flow.

In another aspect, the invention pertains to a method for treating hypertension in a patient. Such methods can include steps of: deploying an implant within an aortic arch of the patient, the implant having a collapsed configuration for advancement through a vasculature of the patient and an expanded configuration for engagement of an arterial wall within an aortic arch of the patient; engaging the arterial wall with the implant in the expanded configuration along a target zone that extends at least between the brachiocephalic artery takeoff and the left subclavian artery takeoff, wherein the implant has a non-circular cross-section when expanded thereby inducing wall tension along the target zone in the aortic arch; and exposing a majority of the arterial wall along the target zone to pulsatile blood flow side openings of the implant so as to sustain the baroreflex response induced by the implant long-term.

BRIEF DESCRIPTION OF THE DRAWINGS

FIGS. 10A-10D show an exemplary implant having two expandable structures interconnected by flexible connectors, the structures defined by four frames and having a square cross section, in accordance with some embodiments.

FIGS. 11A-11B shows an alternative embodiment of the implant, where the expandable structures are defined by three frames and having a triangular cross-section.

FIGS. 12A-12B shows an alternative embodiment of the implant, where the expandable structures are defined by five frames and having a hexagonal cross-section.

FIG. 15A-15D show the mechanism of action by which an appropriately sized structure engages and stretches a substantially round (e.g., 25 mm diameter) aortic arterial wall to achieve sufficient stretch and reshaping to induce baroreflex, in accordance with embodiments of the invention.

Figure 16:
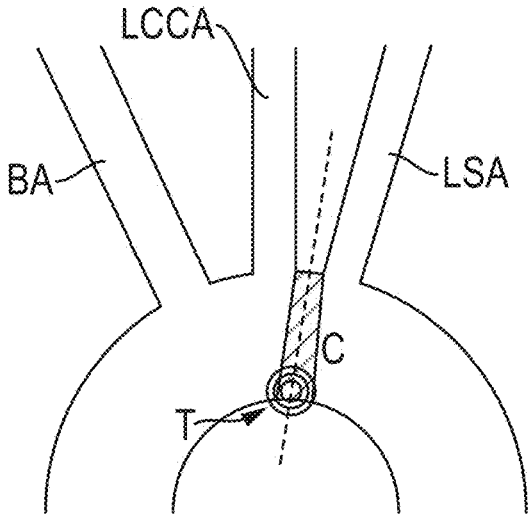

FIG. 16 illustrates a portion of the target region of the aorta, which is the entire aortic segment between the LCCA and LSA, in accordance with some embodiments.

Figure 17:
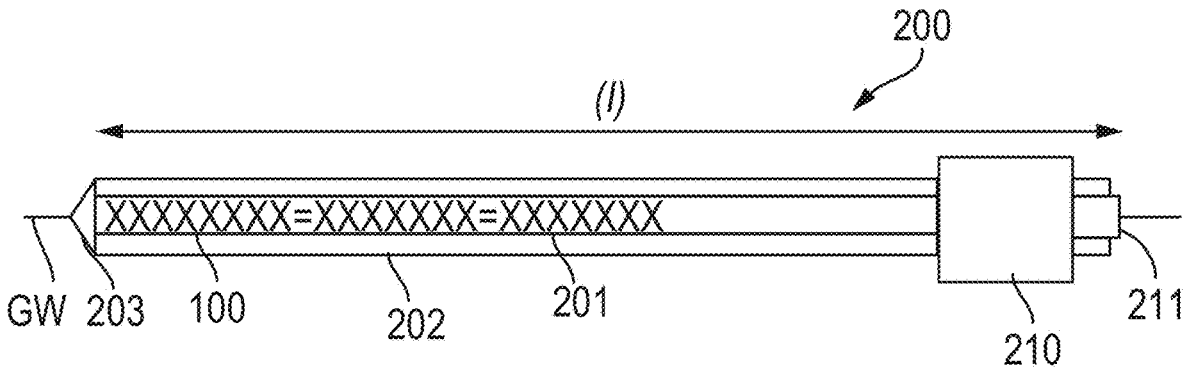

FIG. 17 illustrates a delivery catheter configured to deliver and deploy the implant in the aortic arch, in accordance with some embodiments.

FIGS. 18A-18D illustrate delivery of an exemplary implant to the aortic arch along the target region with the delivery catheter, in accordance with some embodiments.

FIGS. 19-20 illustrates methods of treating hypertension with an implant, in accordance with some embodiments.

FIGS. 21A-1 through 21C-3 illustrate alternative designs of expandable structures for aortic arch baroreceptor implants, in accordance with some embodiments.

Figure 22:
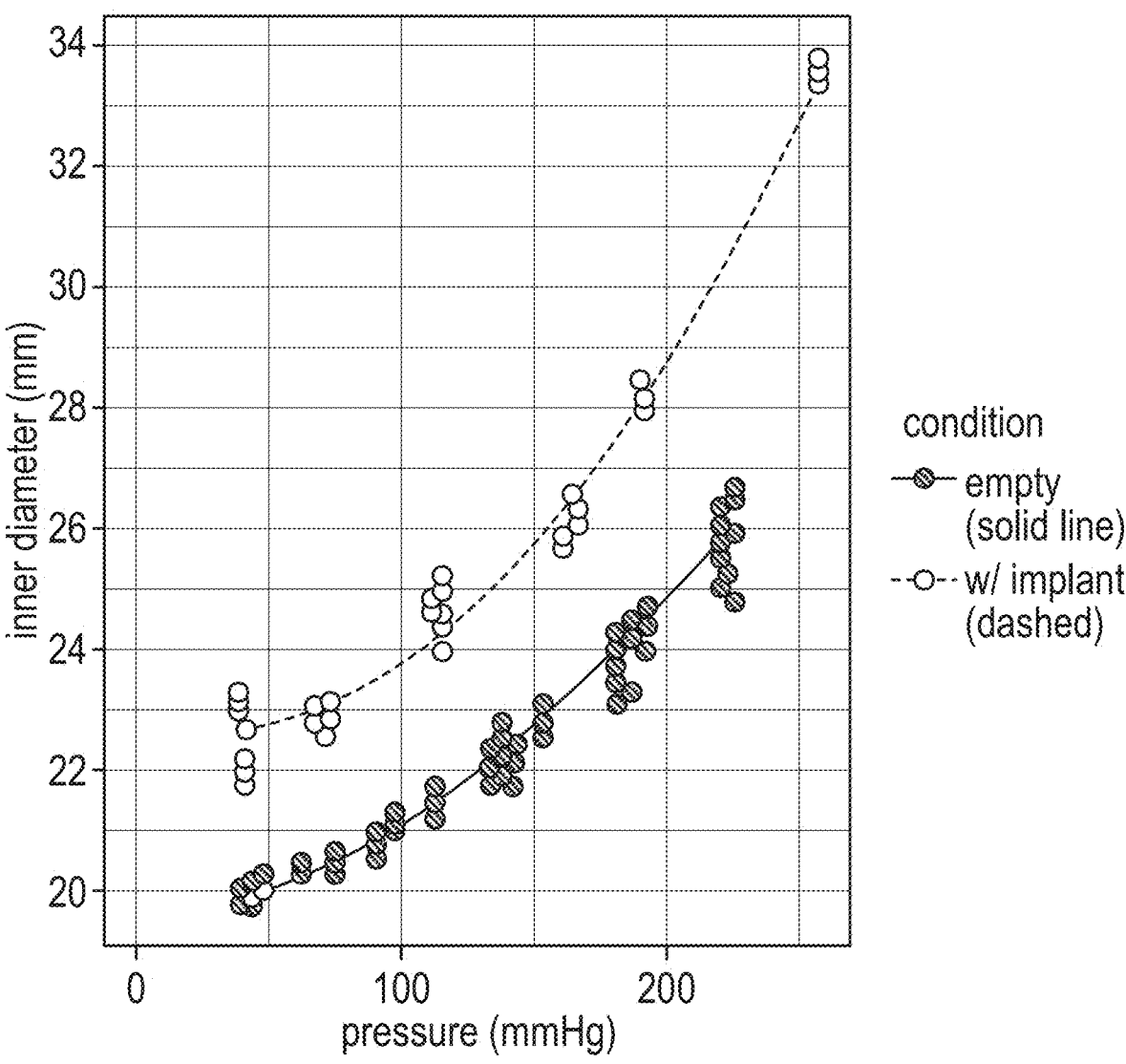

FIG. 22 illustrates a relationship between compliance of a simulated aortic arch vessel before and after placement of an implant, in accordance with some embodiments.

Figure 23A:
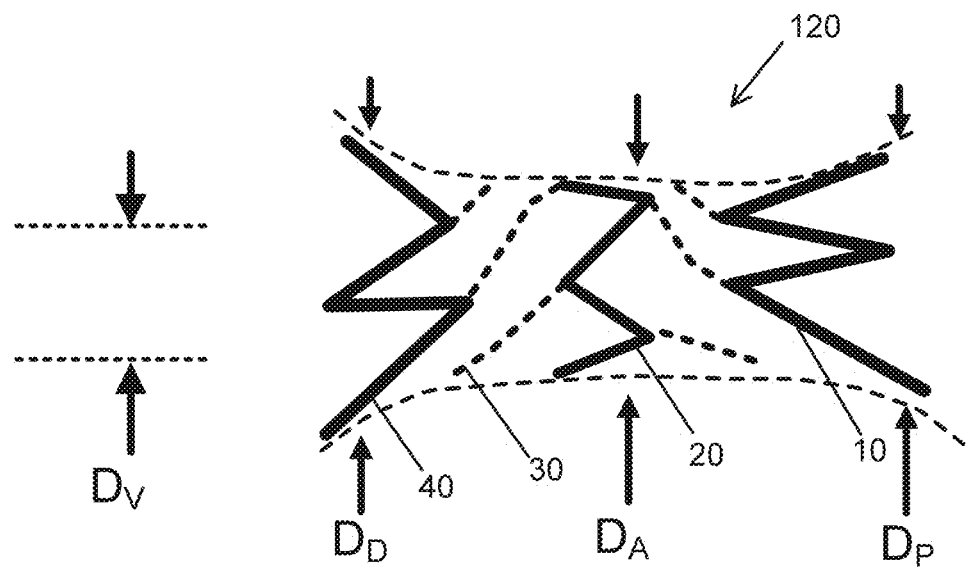
Figure 23B:
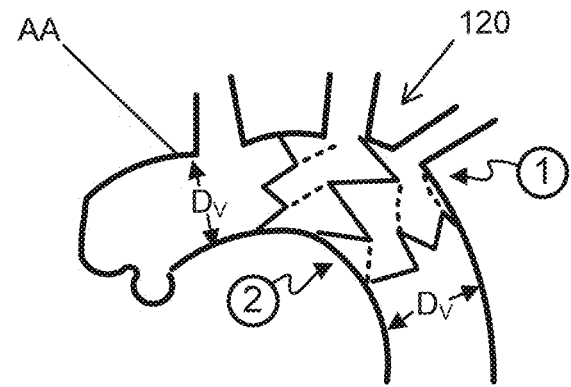
Figure 24A:
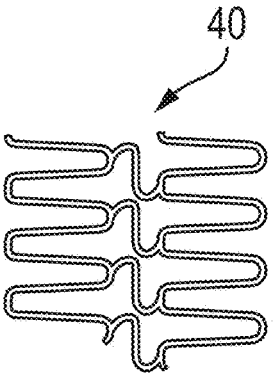
Figure 24B:
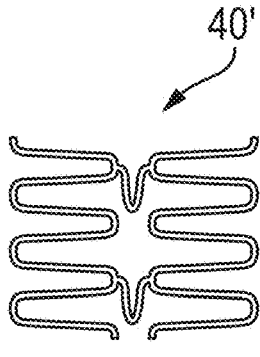
Figure 24C:
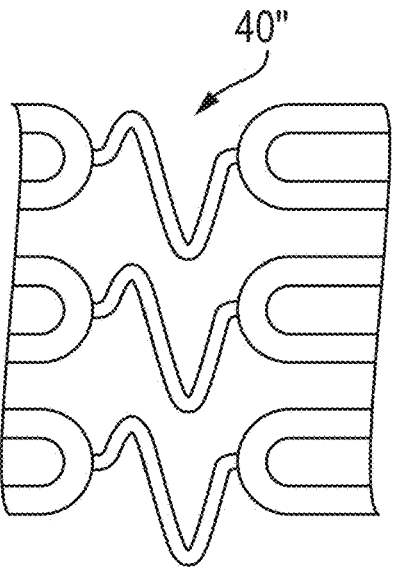
Figure 24D:
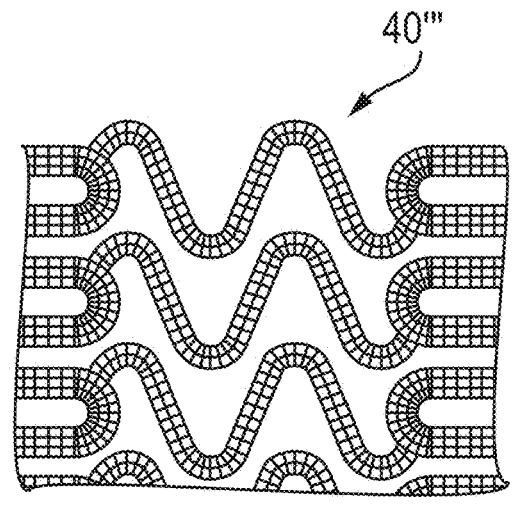
Figure 24E:
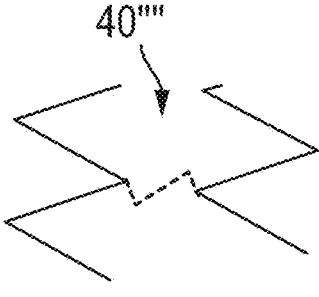
Figure 24F:
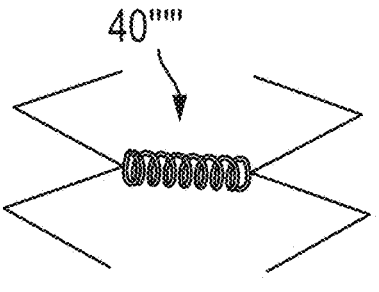

FIGS. 23A-23B illustrates an exemplary implant utilizing multiple expandable structures, similar to those in FIGS. 21A-1 through 21C-3, interconnected by flexible connectors and deployed in the aortic arch, in accordance with some embodiments.

FIGS. 24A-24F illustrates alternative flexible connectors designs between adjacent expendable structures for use in aortic arch baroreceptor implants, in accordance with some embodiments.

Figure 25:
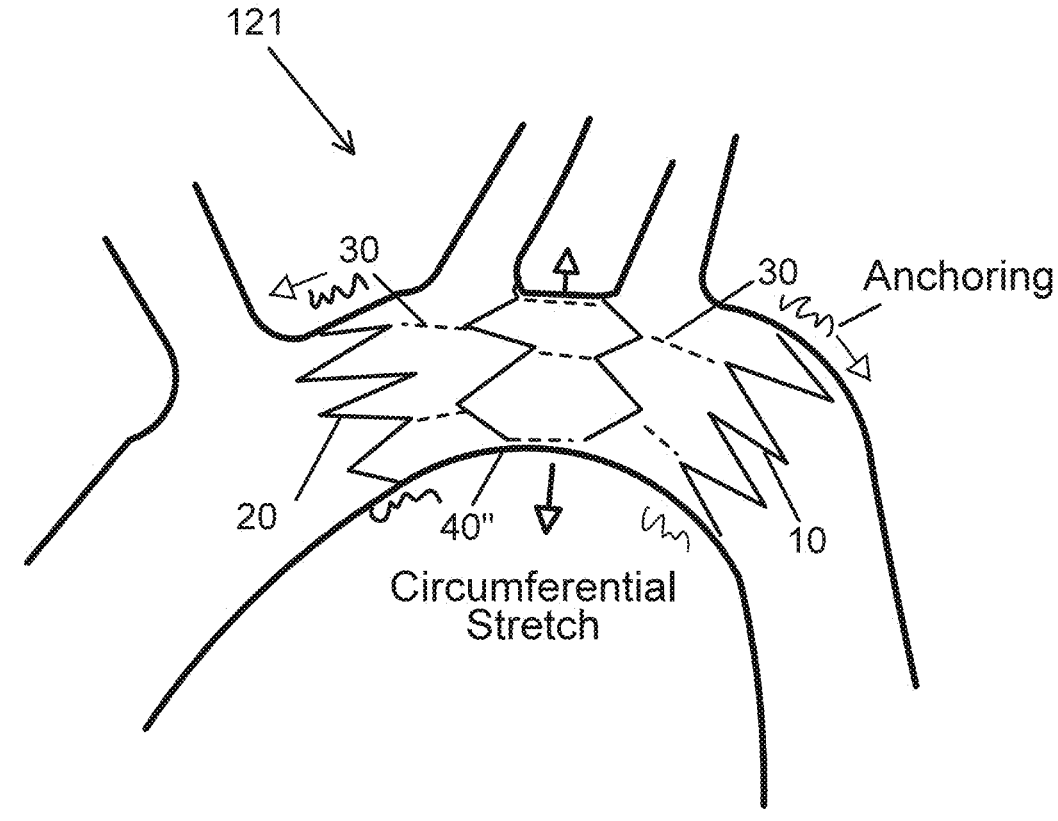

FIG. 25 illustrates another exemplary implant for treating hypertension configured to stretch the arterial walls both circumferentially and axially, in accordance with some embodiments.

FIG. 26 illustrates steps of deploying the implant of FIG. 25 in the aortic arch, in accordance with some embodiments.

FIG. 27 depicts another exemplary implant that can be used for hypertension treatment in a deployed configuration, in accordance with some embodiments.

FIG. 28 depicts the exemplary implant of FIG. 27 in a constrained configuration, in accordance with some embodiments.

FIG. 29 depicts the exemplary implant of FIG. 27 in a constrained unrolled configuration, in accordance with some embodiments.

Figure 30A:
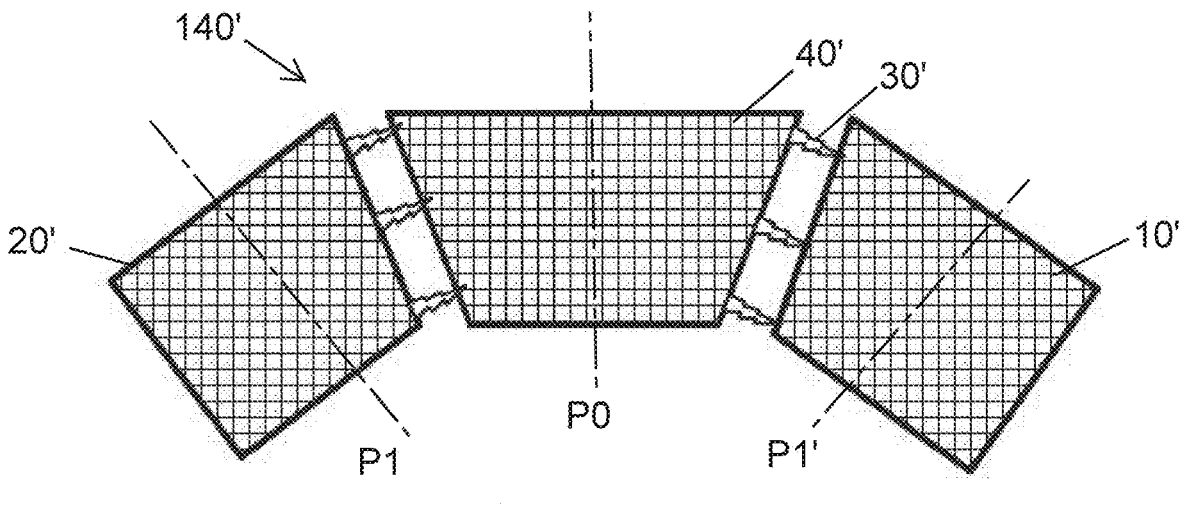
Figure 30B:
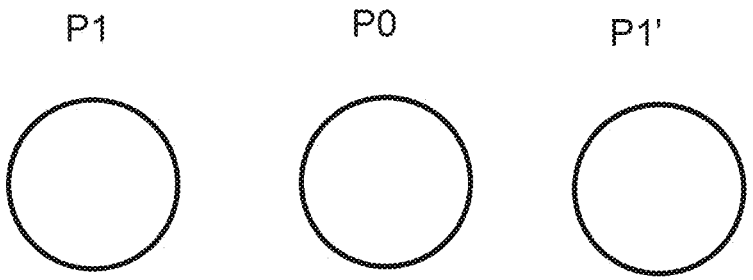

FIG. 30A depicts the implant of FIG. 27 in a deployed configuration and associated cross-sectional views are shown in FIG. 30B, in accordance with some embodiments.

Figures 31A, 31B:
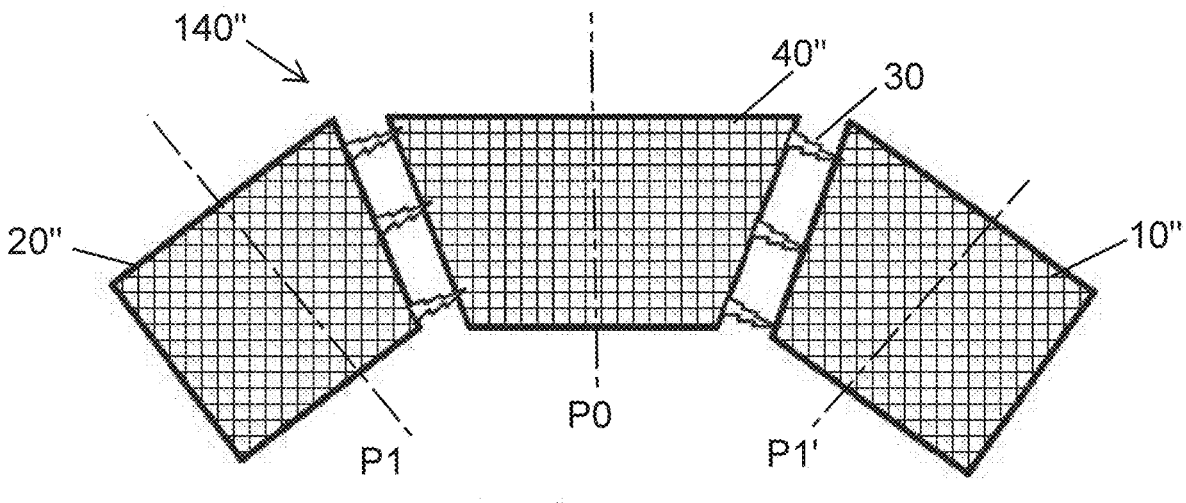

FIG. 31A depicts the implant of FIG. 27 in a deployed configuration and associated cross-sectional views are shown in FIG. 31B, in accordance with some embodiments.

Figure 32:
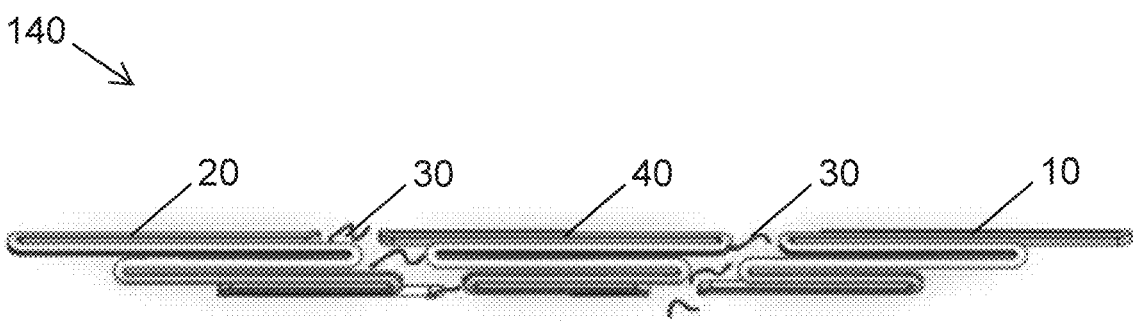
Figure 33:
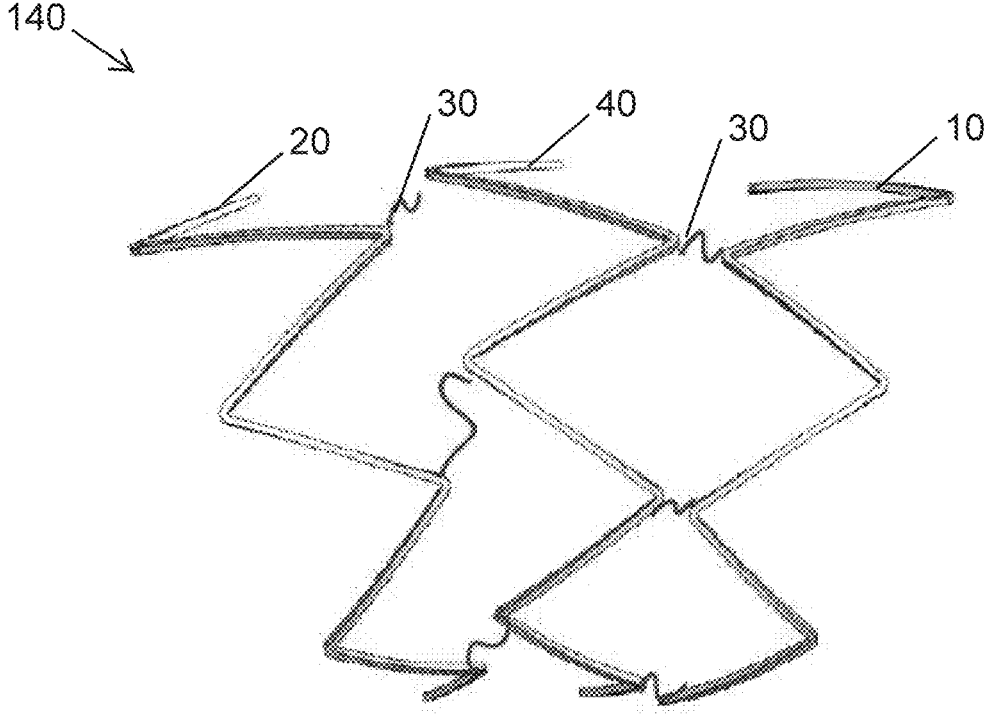

FIG. 32 depicts an exemplary implant in a constrained configuration for delivery and FIG. 33 illustrates the implant in a deployed configuration, in accordance with some embodiments.

Figure 34:
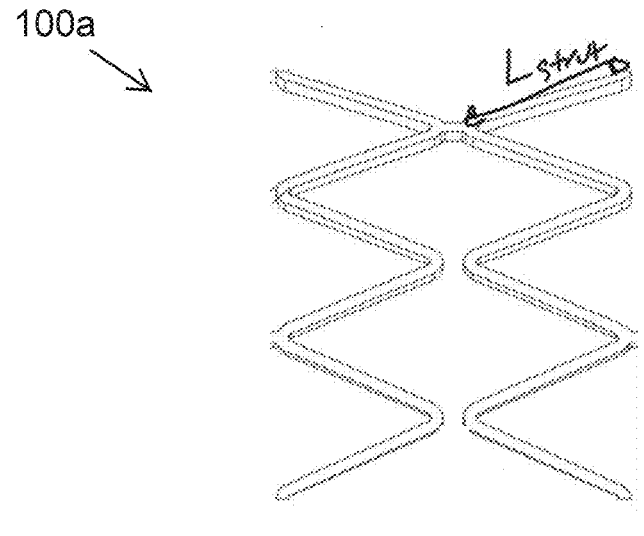

FIG. 34 depicts a strut configuration where struts are of equal length, in accordance with some embodiments.

Figure 35:
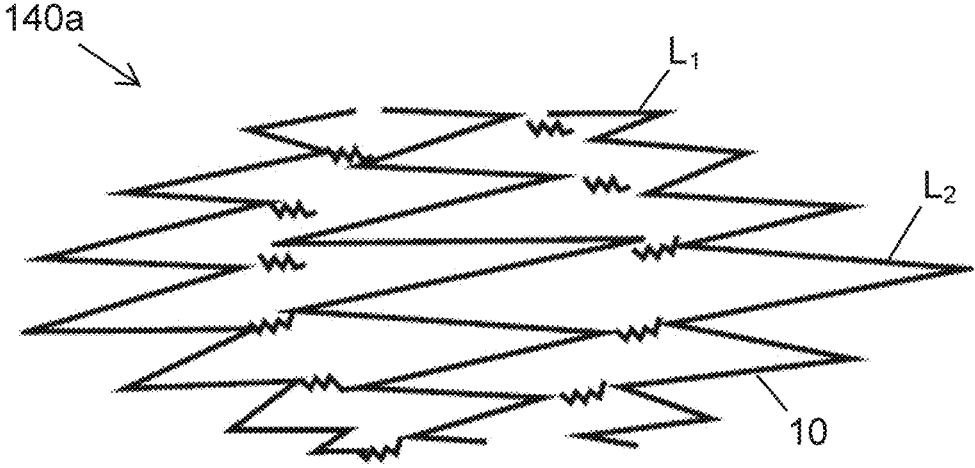

FIG. 35 depicts a strut configuration where struts are of variable length, in accordance with some embodiments.

Figure 36A:
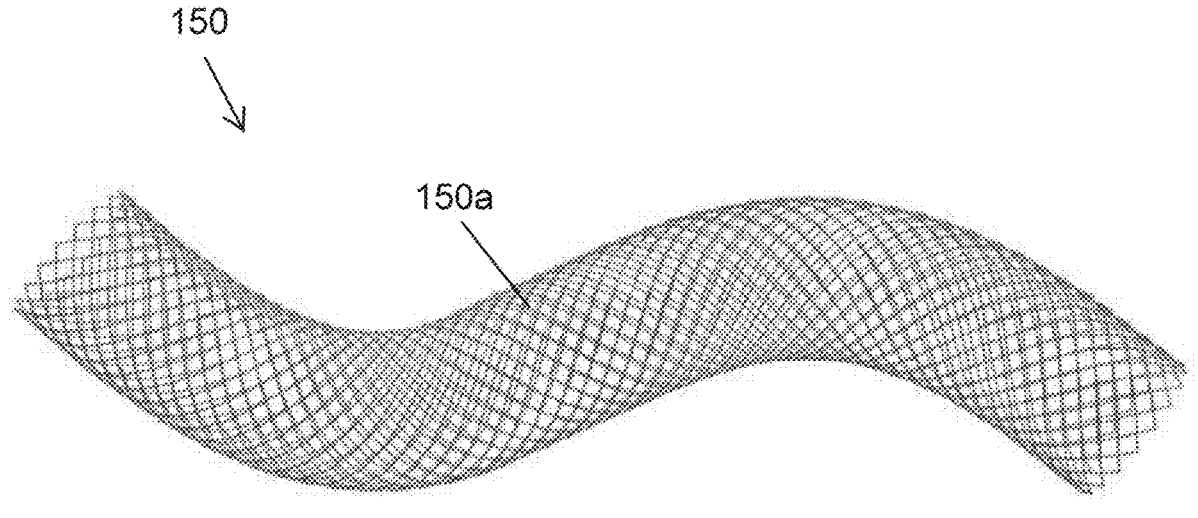
Figure 36B:
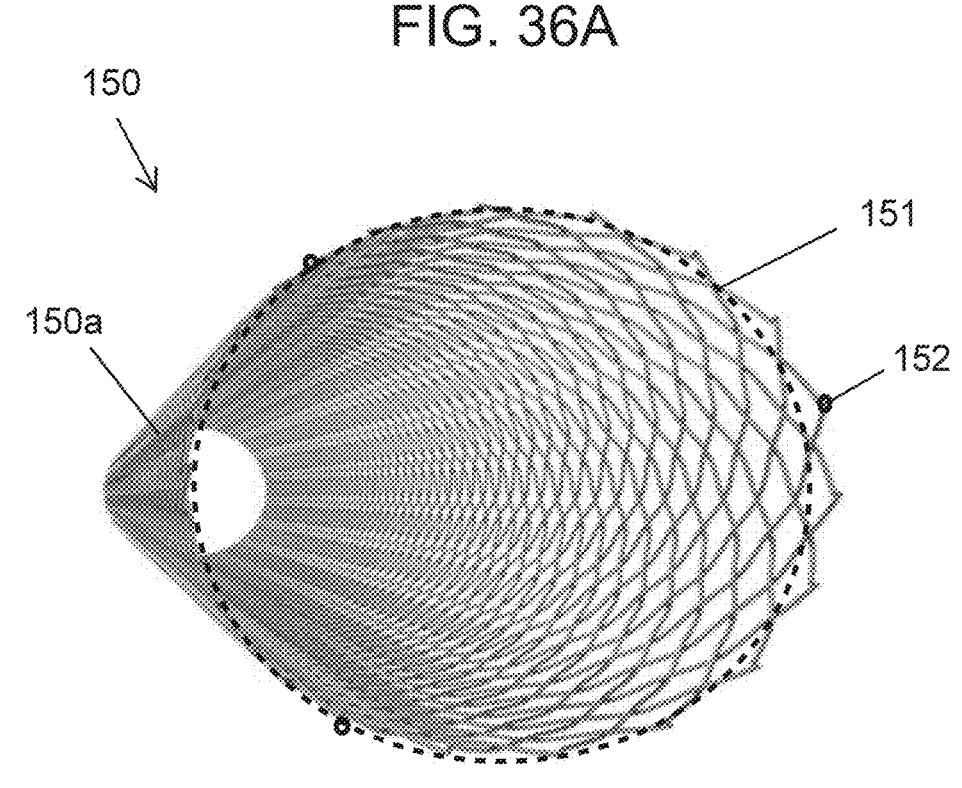

FIGS. 36A-36B shows an exemplary implant structure that is formed of braided wire and has a non-circular cross-sectional shape to tension the artery in which it is deployed by reshaping the artery, in accordance with some embodiments.

Figure 36C:
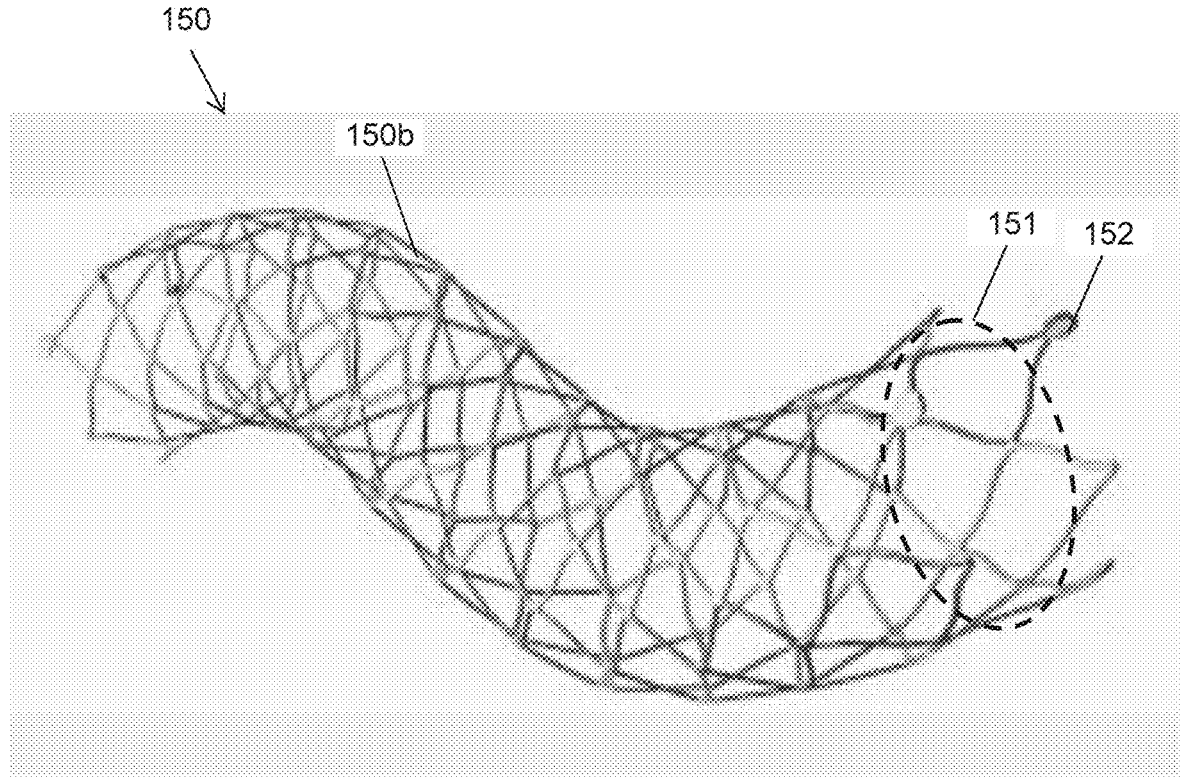

FIG. 36C shows an exemplary implant structure that is laser cut and has a non-circular cross-sectional shape to tension the artery in which it is deployed by reshaping, in accordance with some embodiments.

Figure 37:
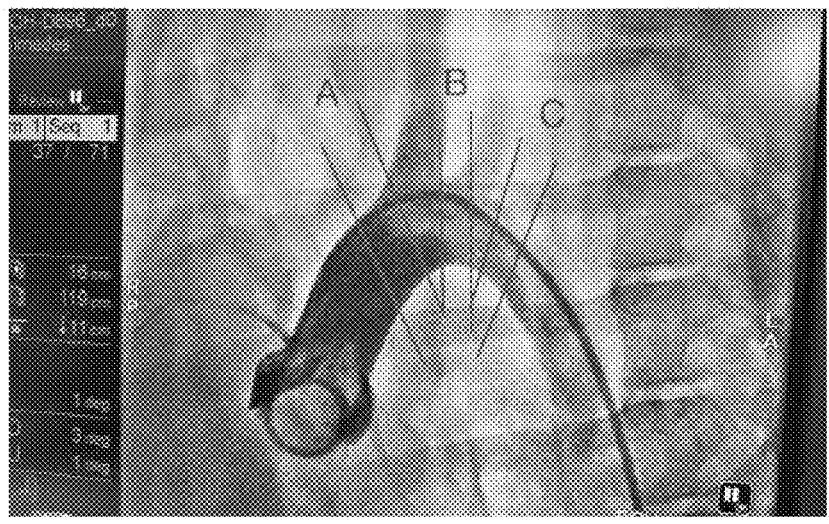
Figure 38A:
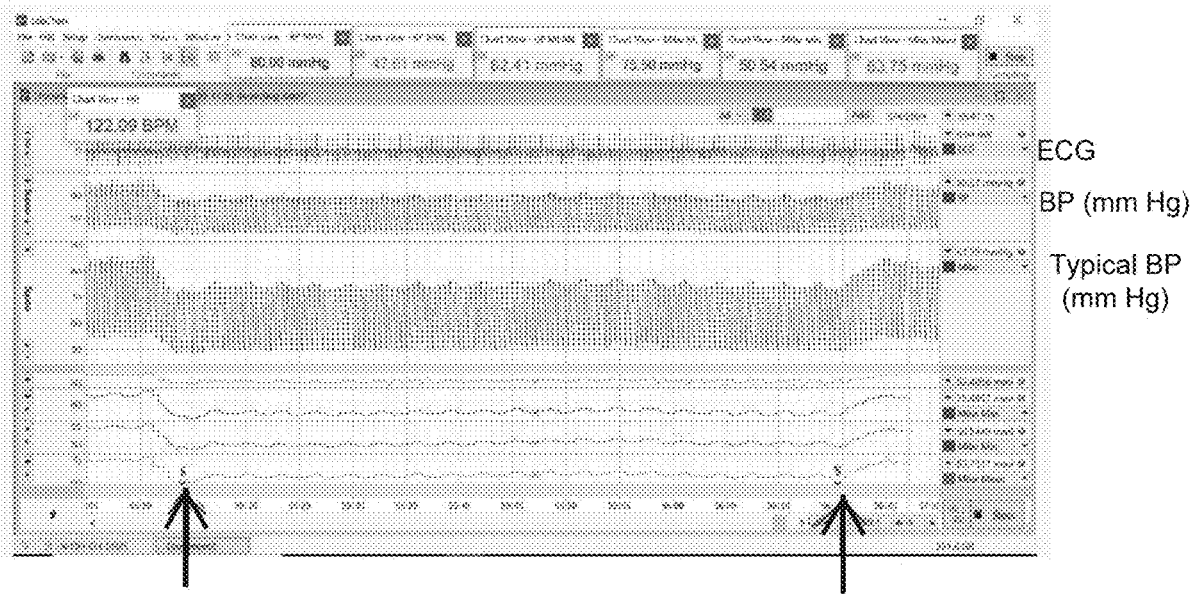
Figures 38B, 38C:
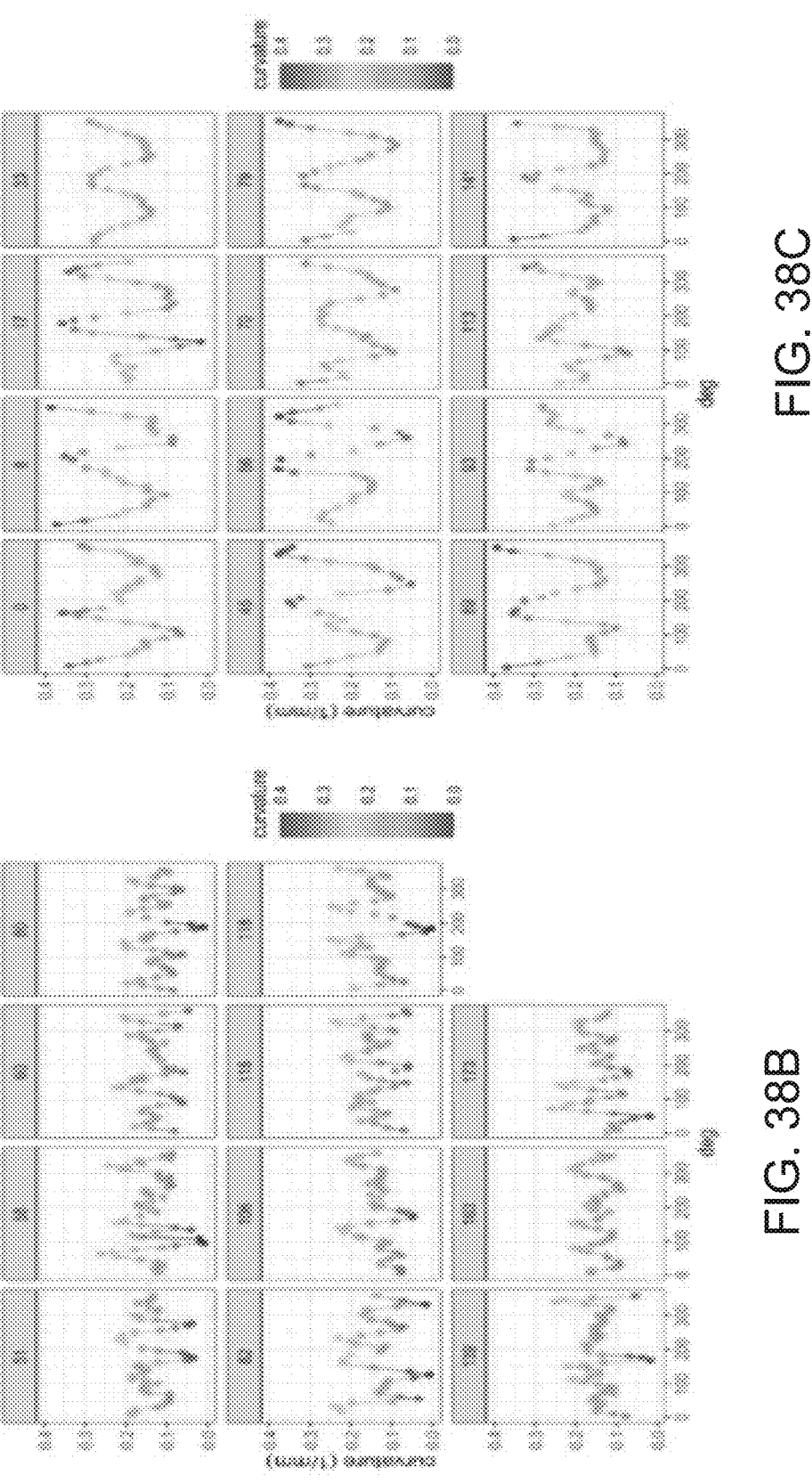

FIGS. 37 and 38A shows images and blood pressure recording from animal testing of the pinch maneuver at differing locations of the aorta to assess a baroreflex response and FIGS. 38B-38C show corresponding curvature by position from ultrasound.

Figure 39:
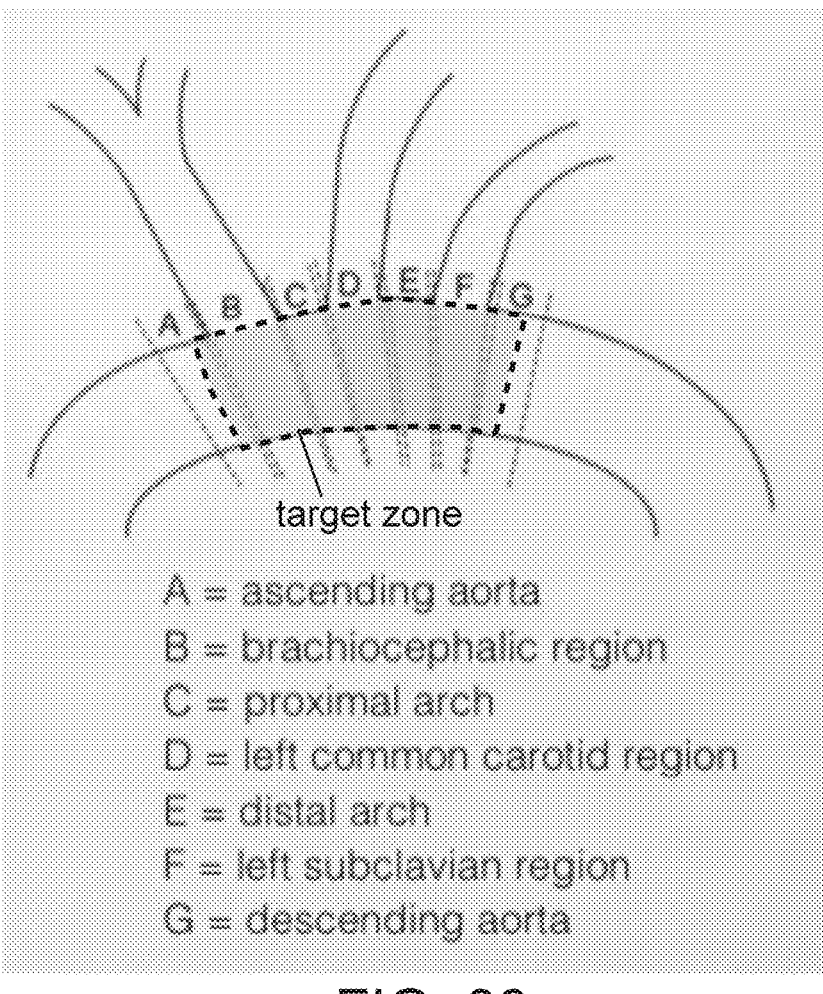
Figure 40:
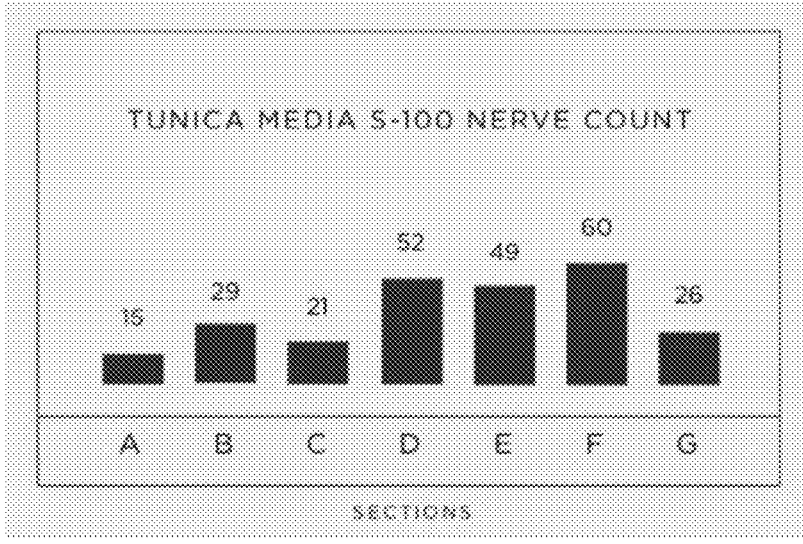

FIGS. 39-40 shows the distribution of aortic arch baroreceptors at differing locations of the aorta as determined from human histology studies.

Figure 41A:
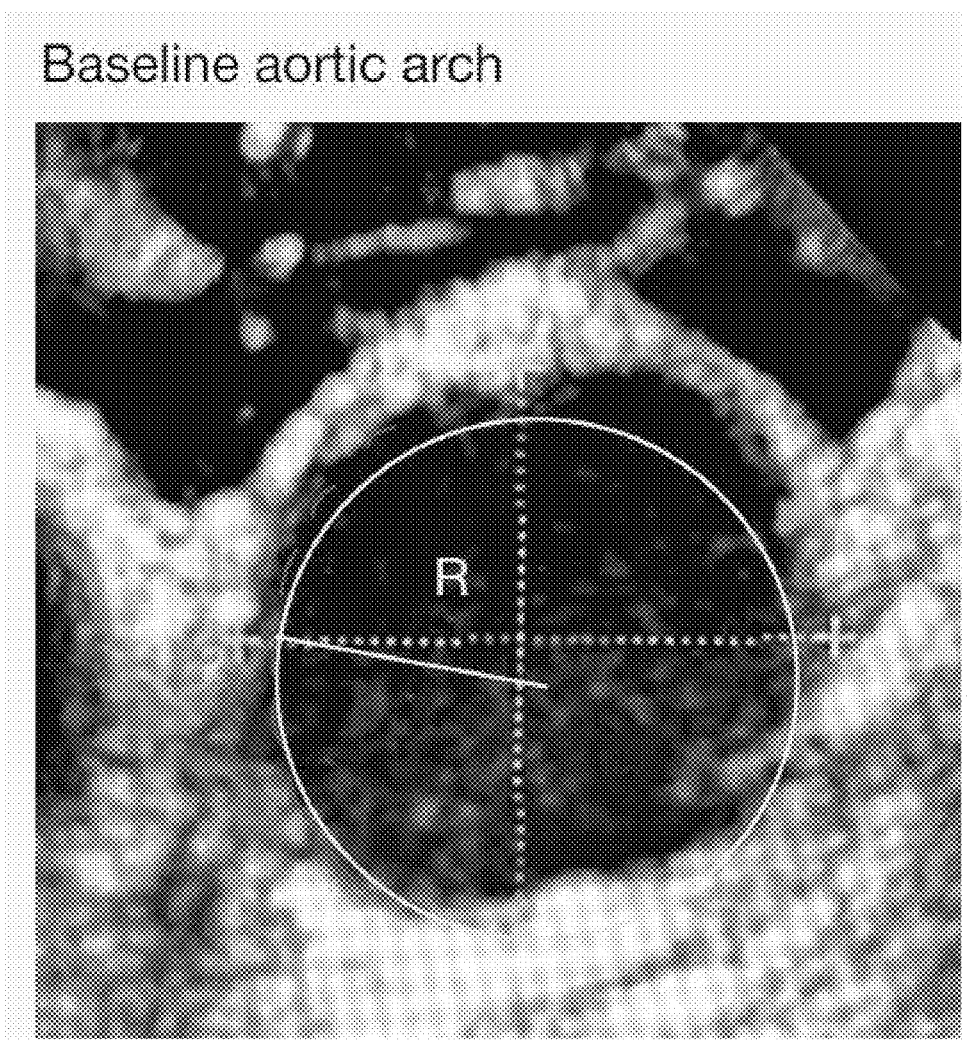
Figure 41B:
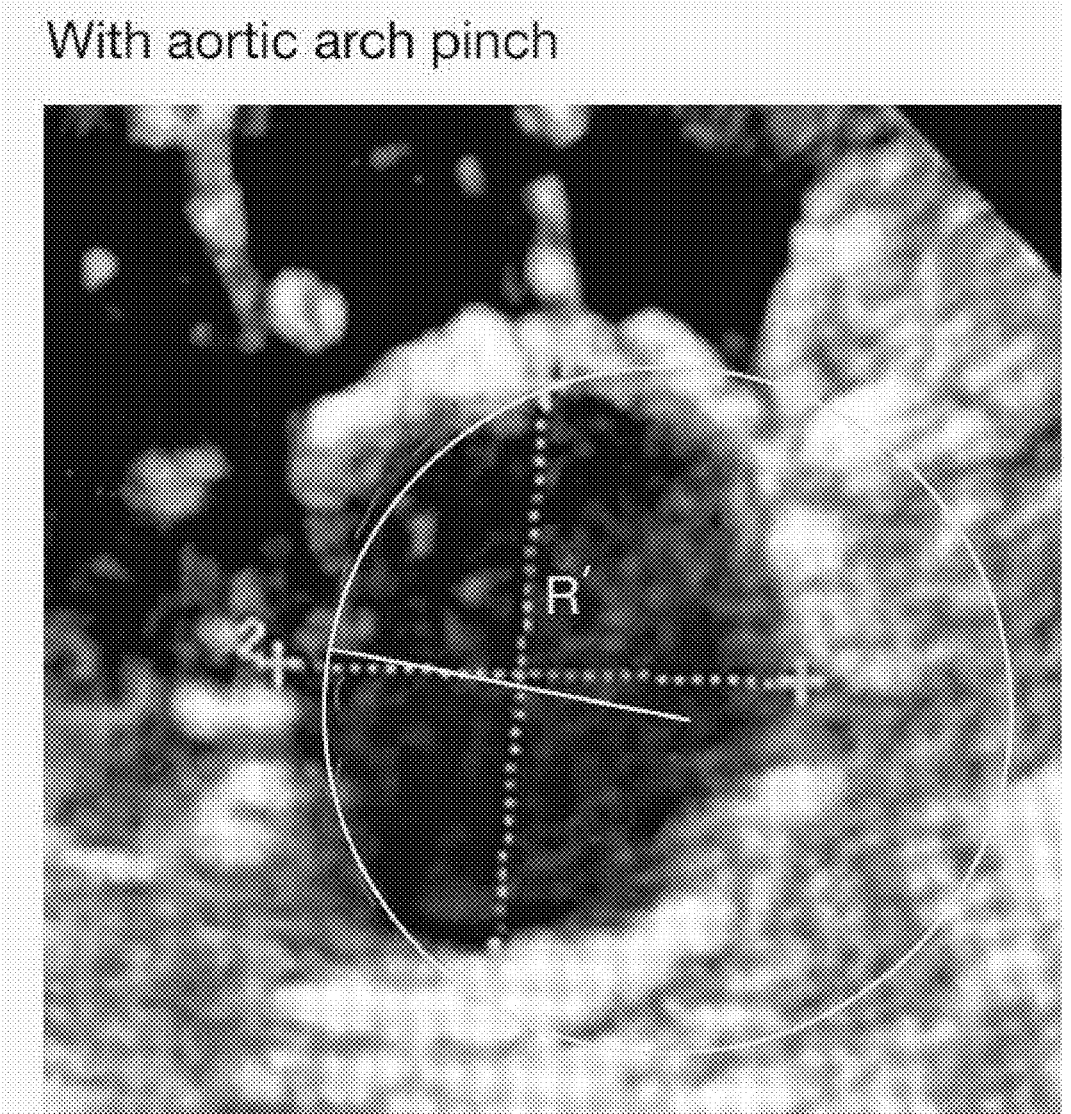

FIGS. 41A-41B show ultrasound images of the aortic arch in animal studies before and after manual pinching of the outside of the artery.

Figure 42A:
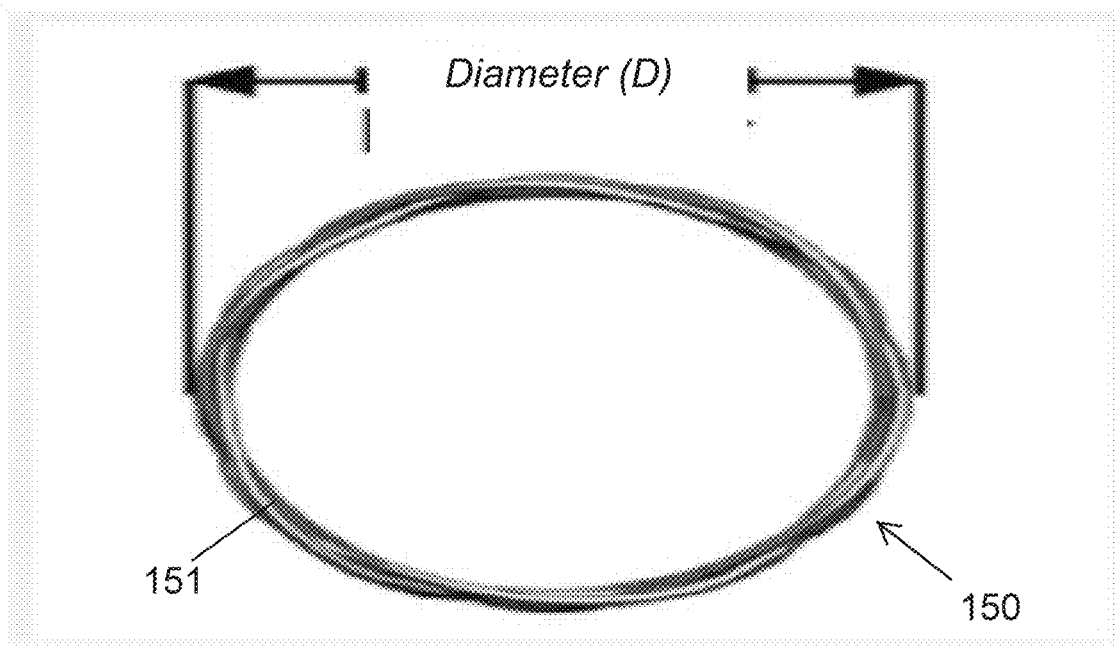
Figure 42B:
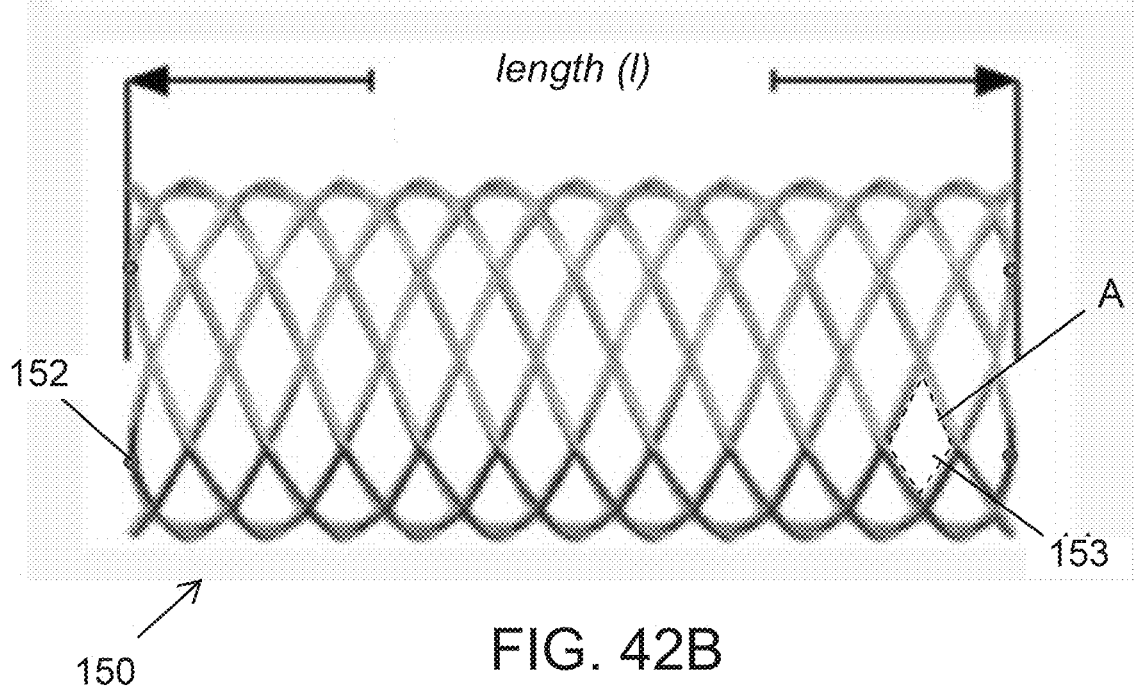

FIGS. 42A-42B illustrate a cross-sectional view and side view of a braided implant having an elliptical cross-sectional shape, in accordance with some embodiments.

Figure 43A:
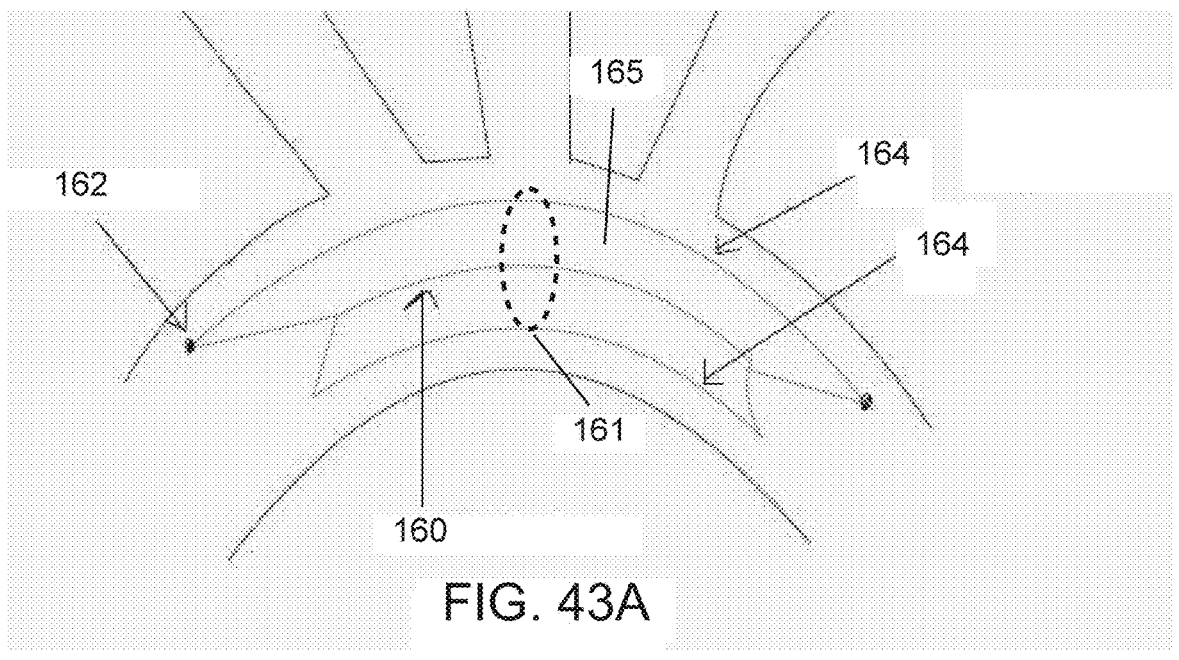
Figure 43B:
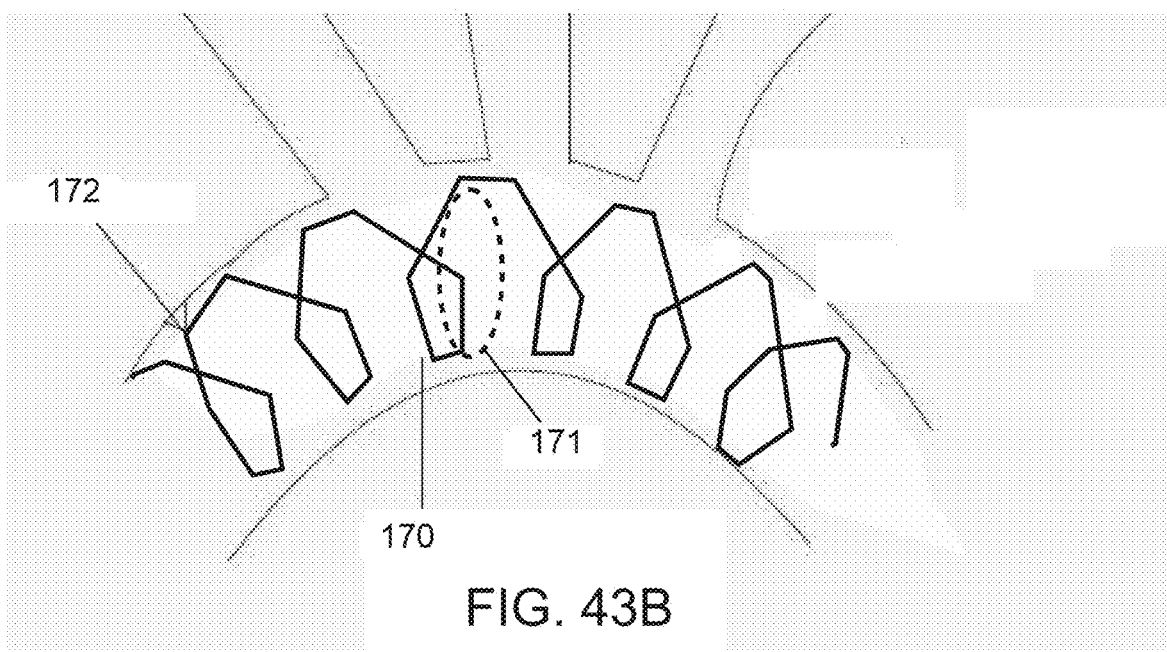

FIGS. 43A-43B illustrate alternative implant designs, in accordance with some embodiments.

FIGS. 44A-44B shows the distribution of the baroreceptors in the aorta.

Figure 45:
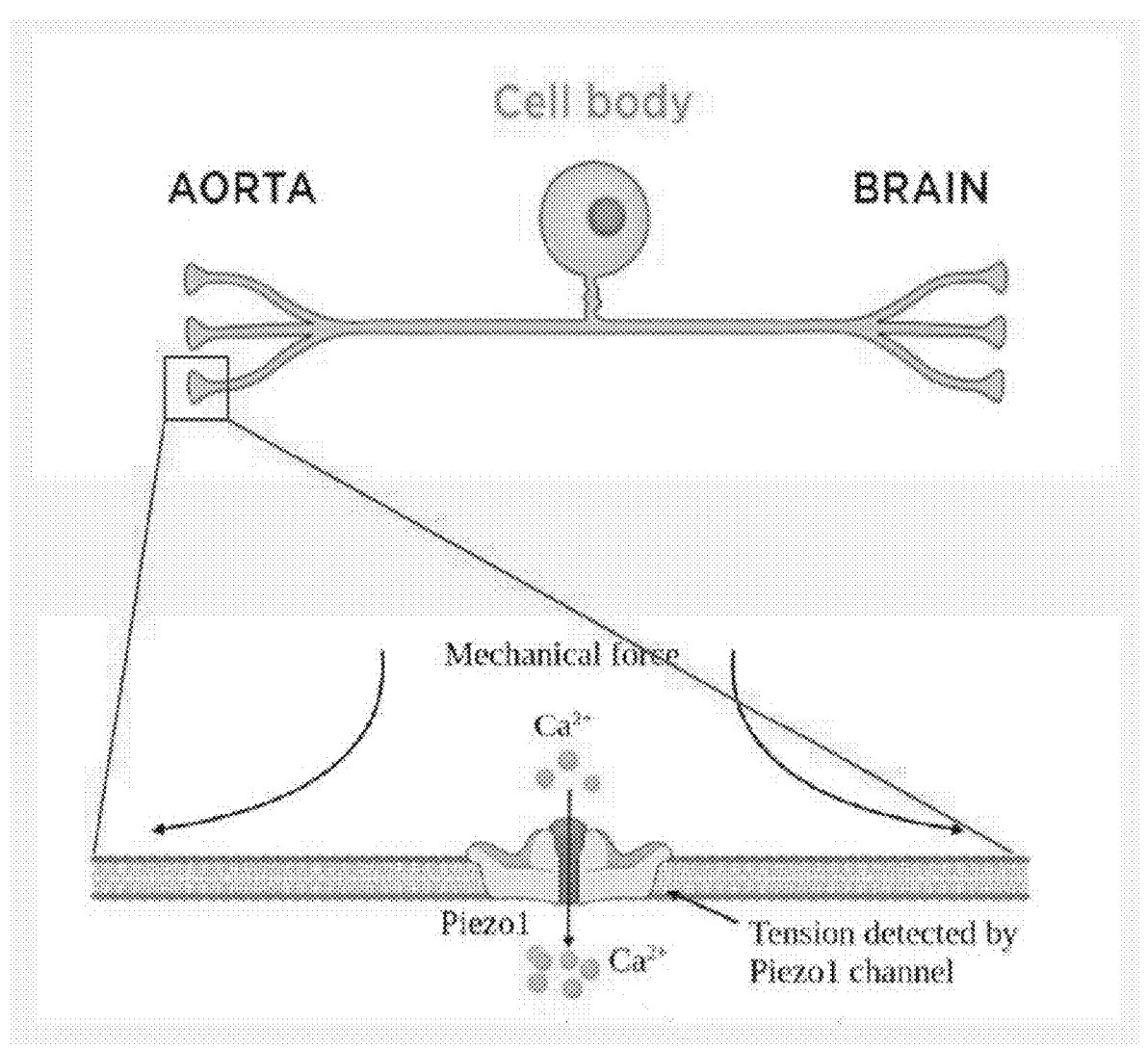

FIG. 45 illustrates the mechanism of action of the baroreceptor response in the aorta.

Figure 46:
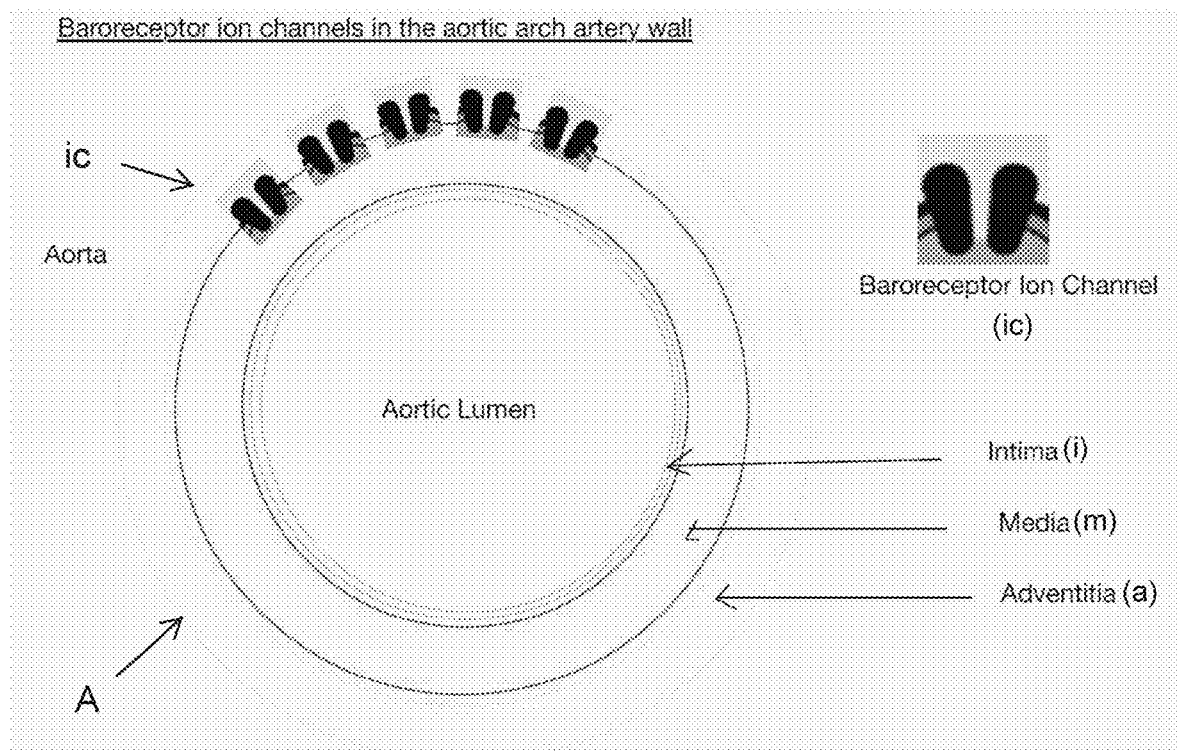

FIG. 46 depicts the baroreceptor ion channels in the aortic arch artery wall.

Figure 47:
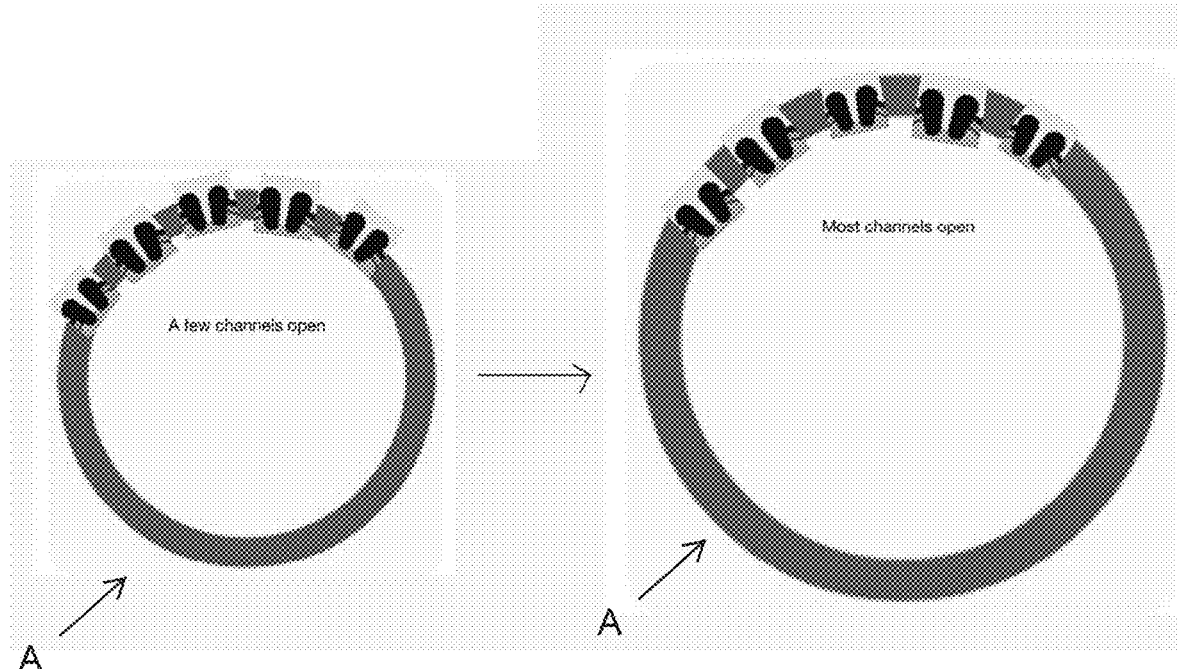

FIG. 47 depicts the theory behind stretch of the arterial wall to activate the baroreflex response in the conventional approach.

Figure 48A:
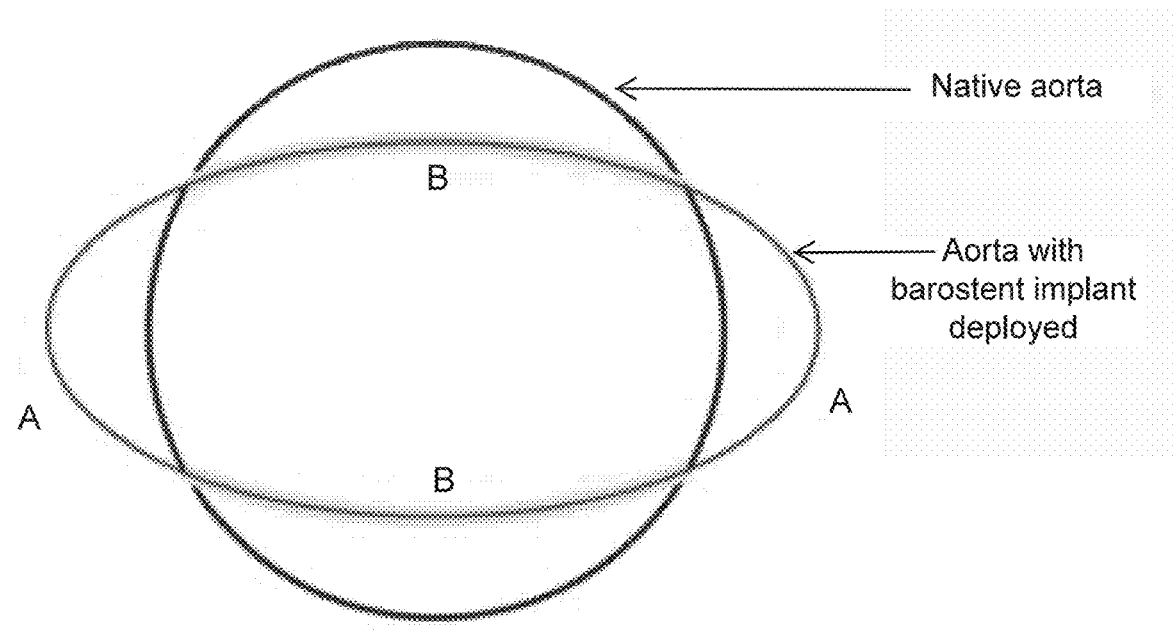
Figures 48B, 48C:
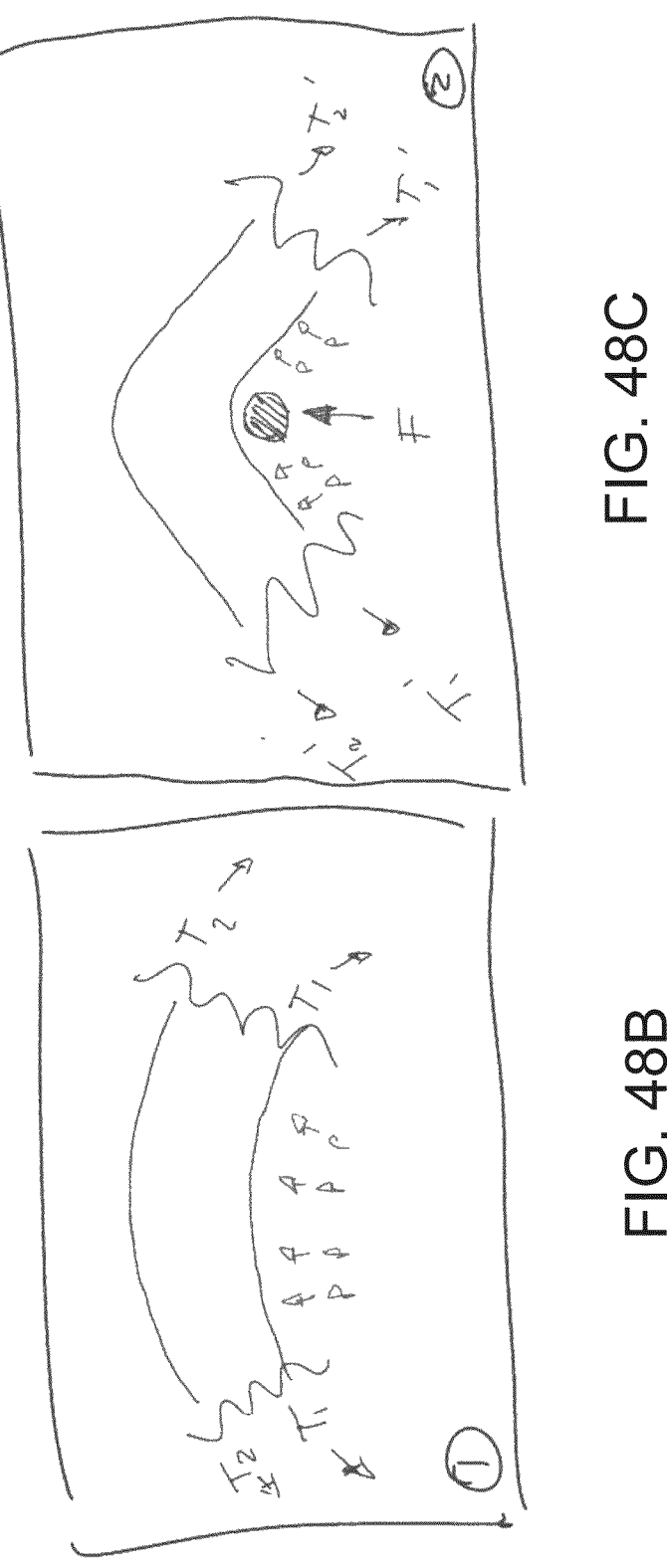

FIG. 48A illustrates the native aorta and the aorta with the barostent implant deployed, demonstrating that tension of the walls result in greater activation of the baroreceptors and FIGS. 48B-48C illustrate the arterial wall before and after tensioning with an element of the implant.

Figure 49:
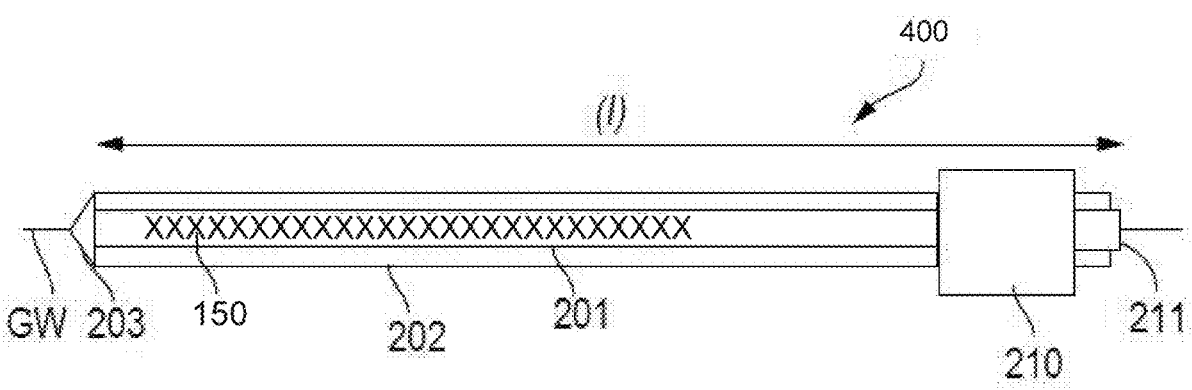

FIG. 49 illustrates a delivery catheter configured to deliver and deploy the implant in the aortic arch, in accordance with some embodiments.

FIG. 50 depicts a method of delivering an implant for treatment of hypertension, in accordance with some embodiments.

DETAILED DESCRIPTION OF THE INVENTION

In one aspect, the invention pertains to an implantable device for treatment of hypertension that is configured for implantation at a target region within the aortic arch to induce a baroreflex response, thereby reducing blood pressure.

I. Physiological Baroreflex Response

Figure 2:
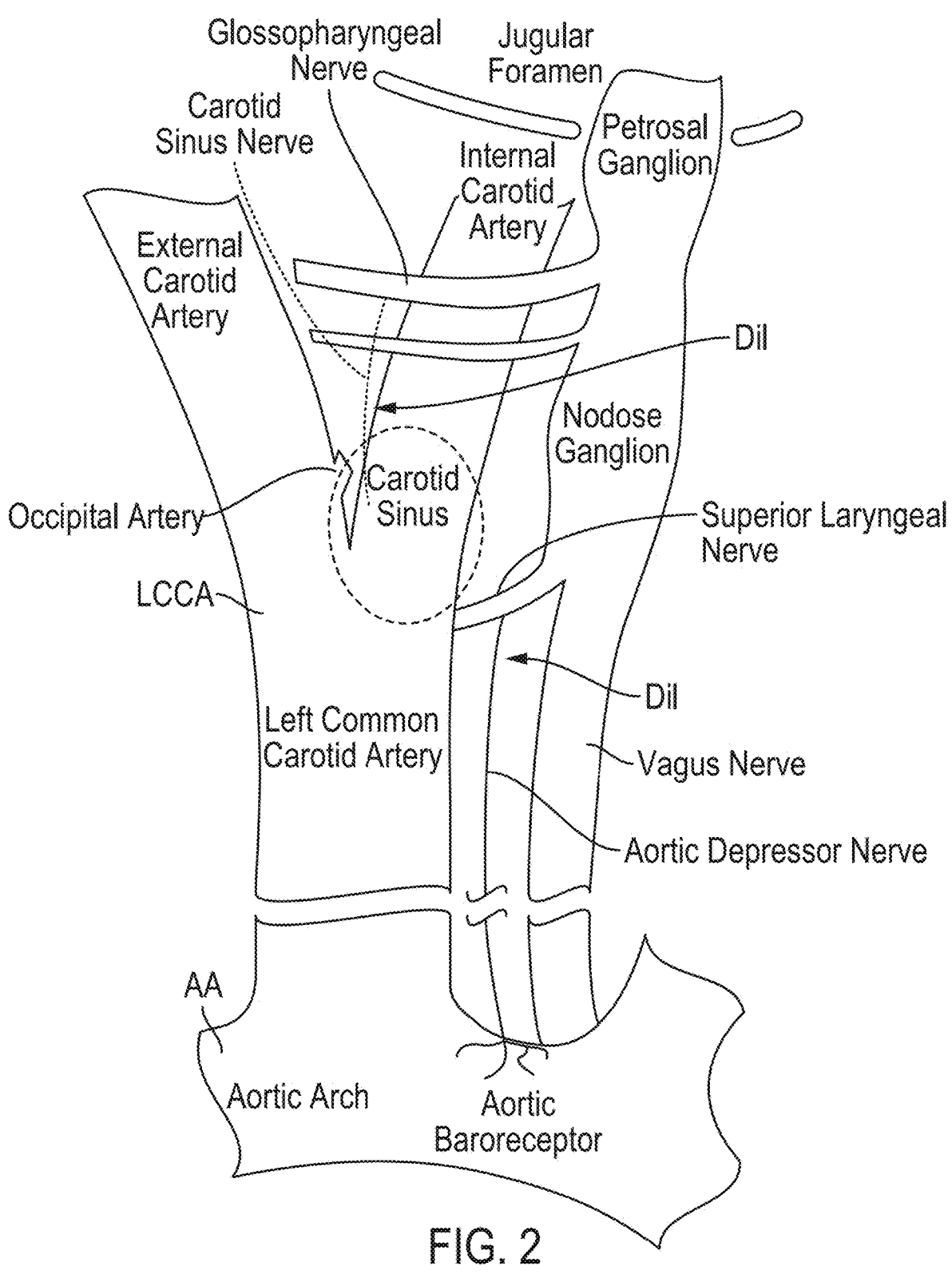
FIG. 2 shows an illustration of a conventional view of the anatomy of the vasculature and baroreceptors and the carotid baroreceptor location targeted by conventional devices.
Figure 3A:
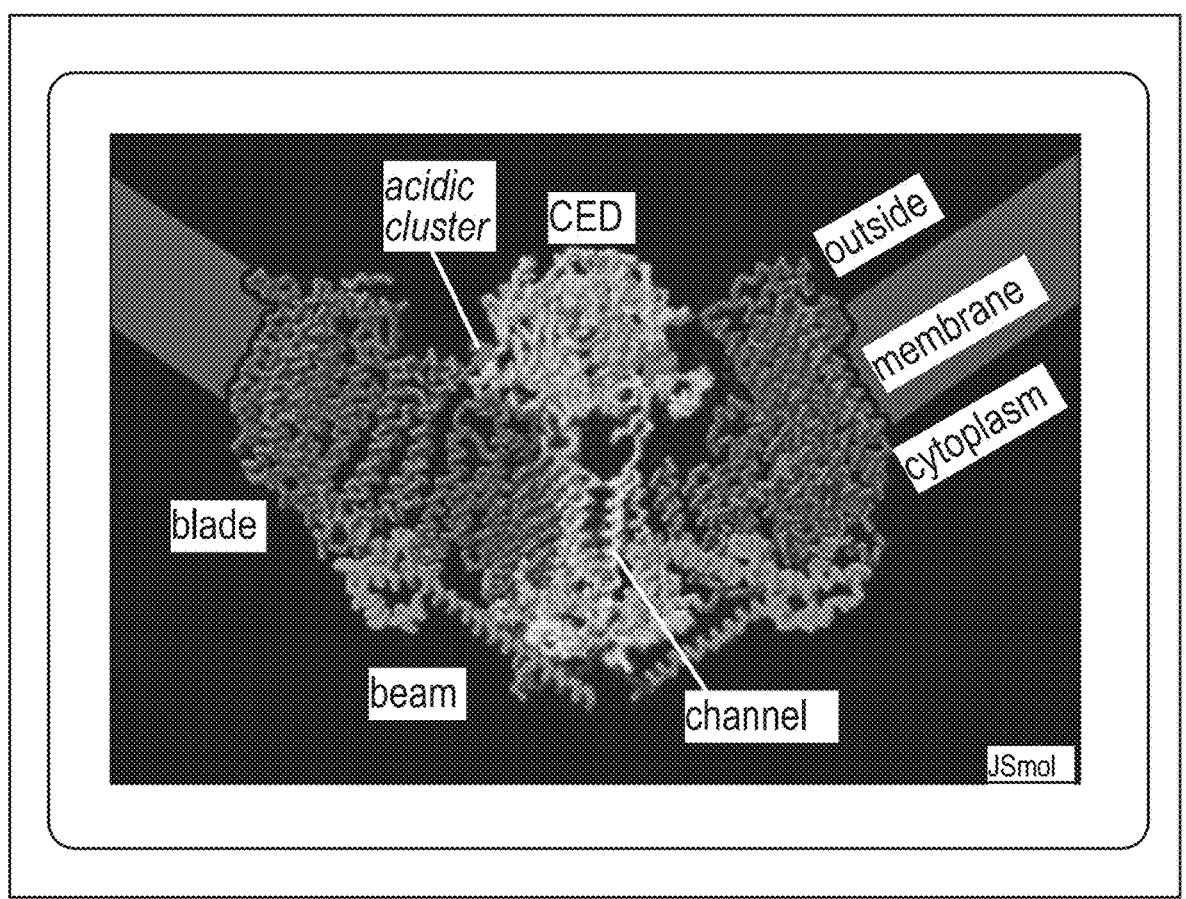
FIG. 3A shows details of an exemplary type of barore-ceptor called PEIZO1.
Figure 3B:
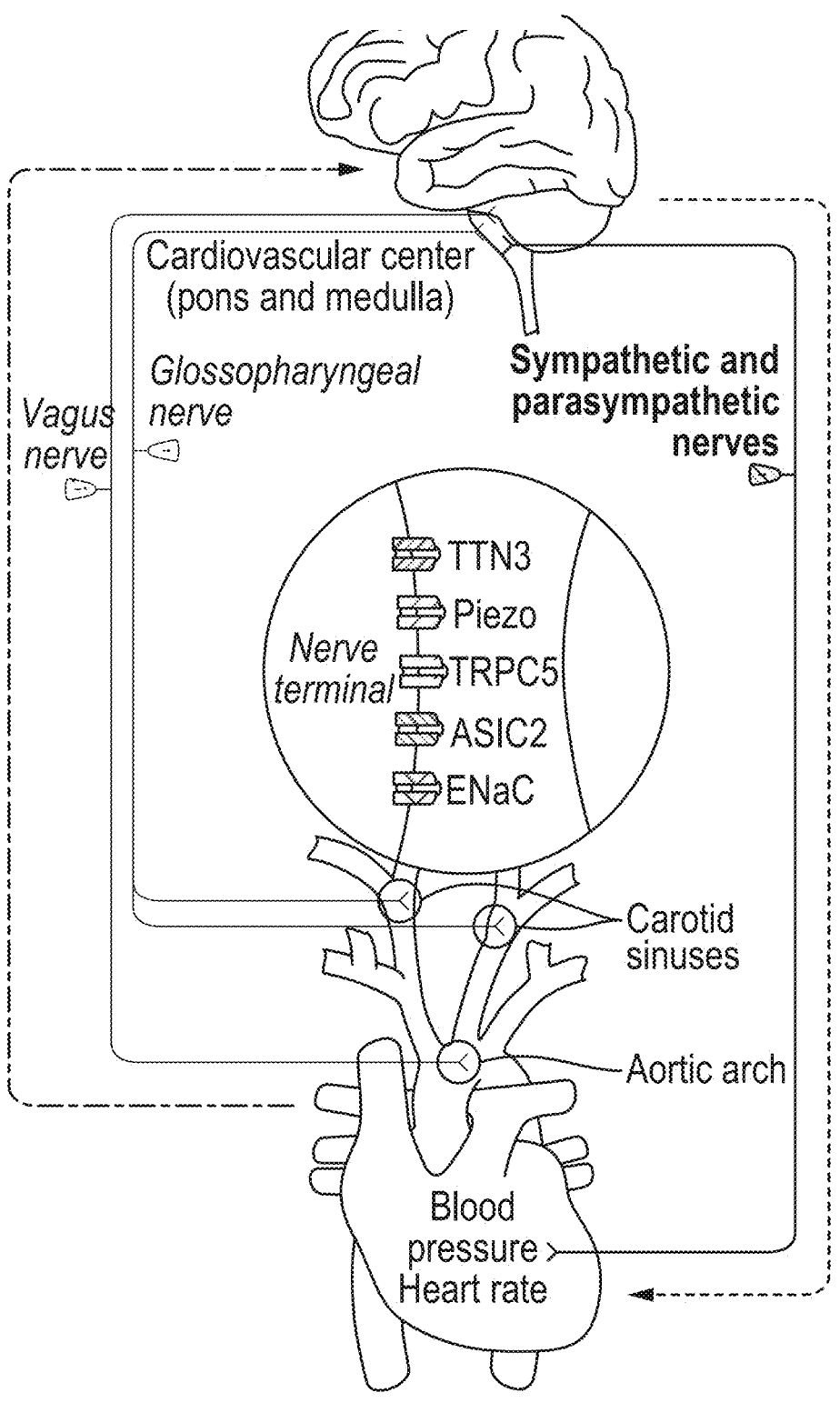
FIG. 3B shows the central nervous system response to baroreflex stimulation in regulating blood pressure.
Figure 3C:
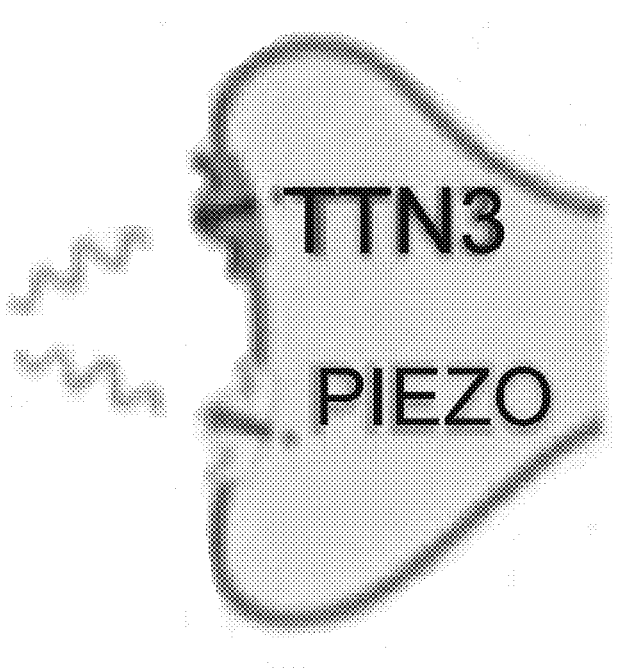
FIG. 3C shows details of an exemplary type of barore-ceptor called PEIZO1.
Figures 1, 2, 3, 21A, 21B, 21C:
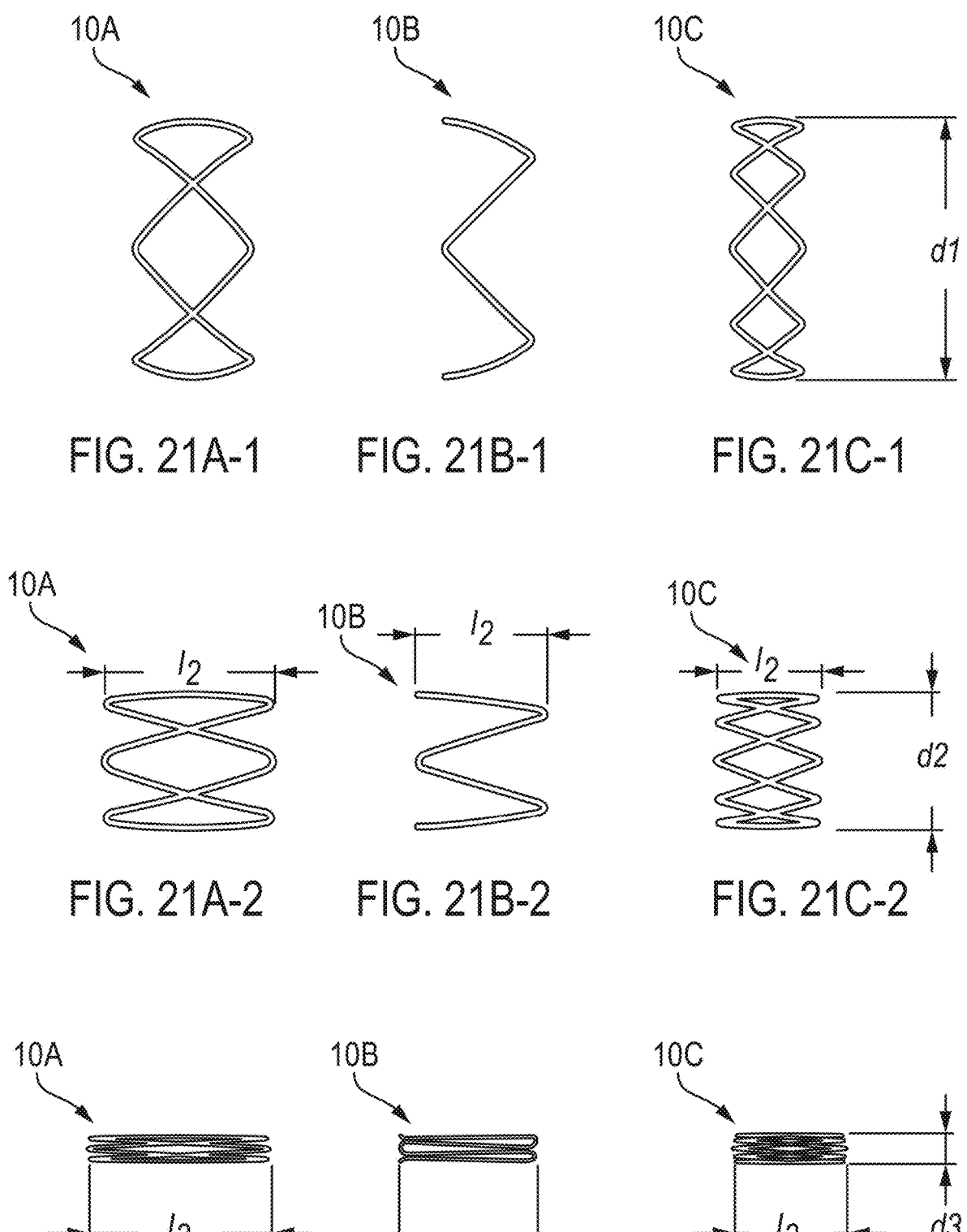

In order to understand the physiological responses of the baroreflex response, it is helpful to understand the interplay between the nervous system within the patient's anatomy. Aspects of the baroreceptor locations with the vasculature, the baroreceptor cells, and the interplay of the baroreceptors with the central nervous system, as shown in FIGS. 2-3B.

Blood pressure sensation occurs at several hotspots within the vascular system. Afferents of the vagus nerve (i.e., cranial nerve 10) and glossopharyngeal nerve (i.e., cranial nerve 9) target the aortic arch and carotid sinus, respectively. Vagal sensory neurons access the aorta through a fine nerve branch termed the aortic depressor nerve, while glossopharyngeal neurons access the carotid sinus through the carotid sinus nerve (see FIG. 2). The aortic depressor and carotid sinus nerves consist of co-fasciculating fibers, including both mechanosensory and chemosensory afferents. The mechanosensory nerve fibers mediate the baroreflex. The terminals of these mechanosensory nerve fibers have specialized nerve endings called baroreceptors that penetrate the artery wall. Baroreceptors are stretch receptors, which do not measure pressure directly, but rather sense stretch of the artery. Blood pressure pulses with each heartbeat radially stretch the artery wall, and this arterial distention in turn activates mechanosensitive neurons. Baroreceptor neurons are long aorta-to-brain sensory neurons that transmit inputs directly to the brainstem. Activation of these baroreceptor neurons decreases sympathetic and increases parasympathetic output from the brainstem ultimately lowering blood pressure and heart rate (termed the baroreflex).

At a molecular level, baroreceptors are actually complex protein structures that form ion channels at the sensory terminals of baroreceptor nerve fibers (see FIGS. 3A-3C and 61-63). Stimulation of the ion channel results in cation influx into the neuron and depolarization with signal transmission along the nerve cell. The baroreceptor nerve terminals are located in the outer wall of the artery between the media and adventitia (see FIGS. 8B and 62).

Baroreceptor neurons are long artery-to-brain sensory neurons that transmit inputs directly to the brainstem. The aortic arch baroreceptor nerve signal emanates from the artery wall, travels through the aortic depressor nerve, then via the superior laryngeal nerve to the vagus nerve, and from there, to the brainstem (see FIGS. 2 and 3B). The brainstem modulates this signal reflexively decreasing sympathetic and increasing parasympathetic nerve output to the circulation. Blood pressure and heart rate fall. This cascade of events is termed the baroreflex.

Early animal studies demonstrated that this response was associated with stretching of the arterial walls, which occurs naturally at high blood pressures. Later animal studies demonstrated that the baroreflex response could be transitory or persistent depending upon whether the arterial receptor site stimulation was static or pulsatile, respectively. Static stimulus resulted in a systemic blood pressure drop but then normalized a few minutes later, whereas a nonstatic, pulsatile stimulus (e.g., similar to natural pulsatile blood flow) showed that the systemic blood pressure drop was sustained.

Since the 1960s, modulation of the baroreflex-specifically the carotid baroreflex—has been the primary target of device-based therapy for difficult to control hypertension. The first efforts involved pacemaker-type devices: electrodes placed around the carotid sinus nerve connected via wires to an implantable stimulator. Stimulation of this nerve-which innervates the carotid baroreceptor-circumvents the stimulus within the artery and can lower blood pressure through the carotid baroreflex arc. This technology continues in human clinical trials. A similar type device for the aortic arch baroreceptor—or more precisely, the aortic depressor nerve—has been used successfully in a goat experimental model to lower blood pressure. Still, pacemaker-type implants are unlikely to be the device-based solution for resistant hypertension due to their obvious drawbacks—for one, patients would prefer not to have a generator surgically inserted into their chest. To overcome this limitation, Vascular Dynamics developed a stent-like endovascular implant that stretched the carotid artery wall from the inside which was though to amplify the carotid baroreflex signal. This device had a non-articulated, monomorphic design configured for a straight segment of the proximal internal carotid artery. In early clinical trials, the device was successful at lowering blood pressure in a resistant hypertension population but at the risk of a small number of cerebral transient ischemic attacks (TIA). There are various drawbacks associated with this approach that may contribute to the increased risk of stroke and TIAs.

The present invention seeks to avoid the above-noted drawbacks associated with the conventional approach by providing an endovascular implant that induces an improved baroreflex response within the aortic arch. In an exemplary embodiment, the invention pertains to an implant having one or more expandable structures configured that engage and reshape the arterial walls along a target region of the aorta, in particular the aortic arch, to generate tension in the arterial walls to induce the baroreflex response. In some embodiments, the invention is configured to engage a target region of the aortic arch, including an inner curvature, opposite the left subclavian artery. This target region can be defined as a cylindrical segment of the aortic arch between the LCCA and the LSA. It is theorized that this portion of the aortic arch is particularly rich in baroreflex receptors and that these receptors have increased sensitivity, as compared to barore-ceptors in various other regions, such as the carotid sinus. Since this region of the aortic arch is believed to provide a heightened response, the implant can achieve more consistent, reliable reductions in blood pressure. Further, implantation in this area avoids the drawbacks associated with delivering and implanting at the sensitive area of the carotid sinus, which may increase the risk of TIAs and strokes. Thus, the implant described herein provides a more robust baroreflex response to reduce blood pressure, improves case of delivery and implantation, and is believed to reduce the risk of adverse events.

Figure 4:
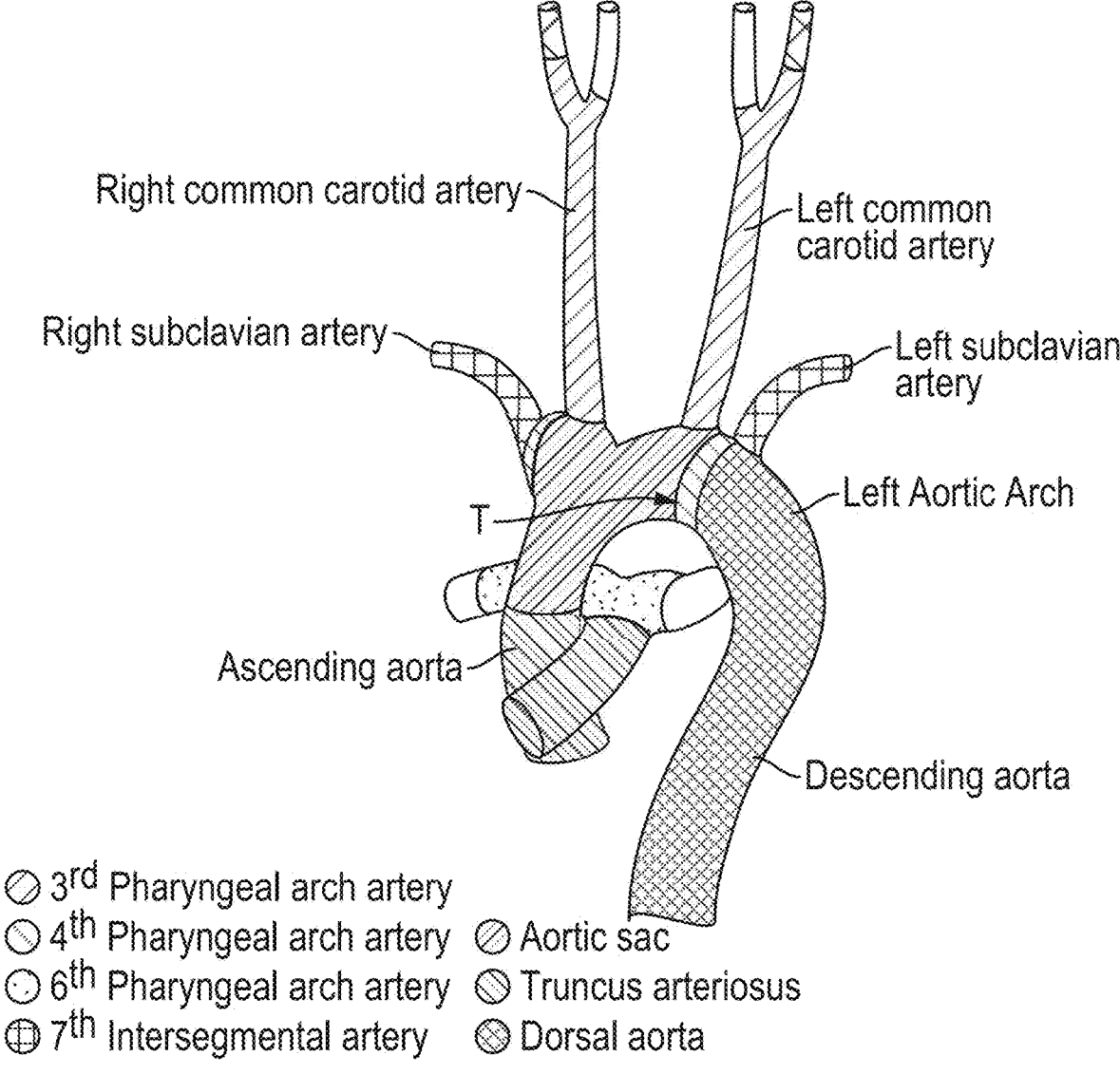
FIG. 4 shows the anatomy of the vasculature of the aortic arch.

Early animal studies of differing baroreceptor responses have identified anatomic "hotspots" of baroreceptors at various locations in the vasculature, including a narrow cylindrical strip that extends circumferentially around the aortic arch between the takeoffs of the left common carotid and left subclavian arteries (the 4th pharyngeal arch artery in FIG. 4). This region is shown in the fluorescence staining image of FIG. 8A, which shows the baroreceptors stained in red. This area rich in baroreceptors can be defined as a cylindrical segment of the aortic arch between the LCCA and the LSA, shown as target T in FIG. 4.

Figure 5:
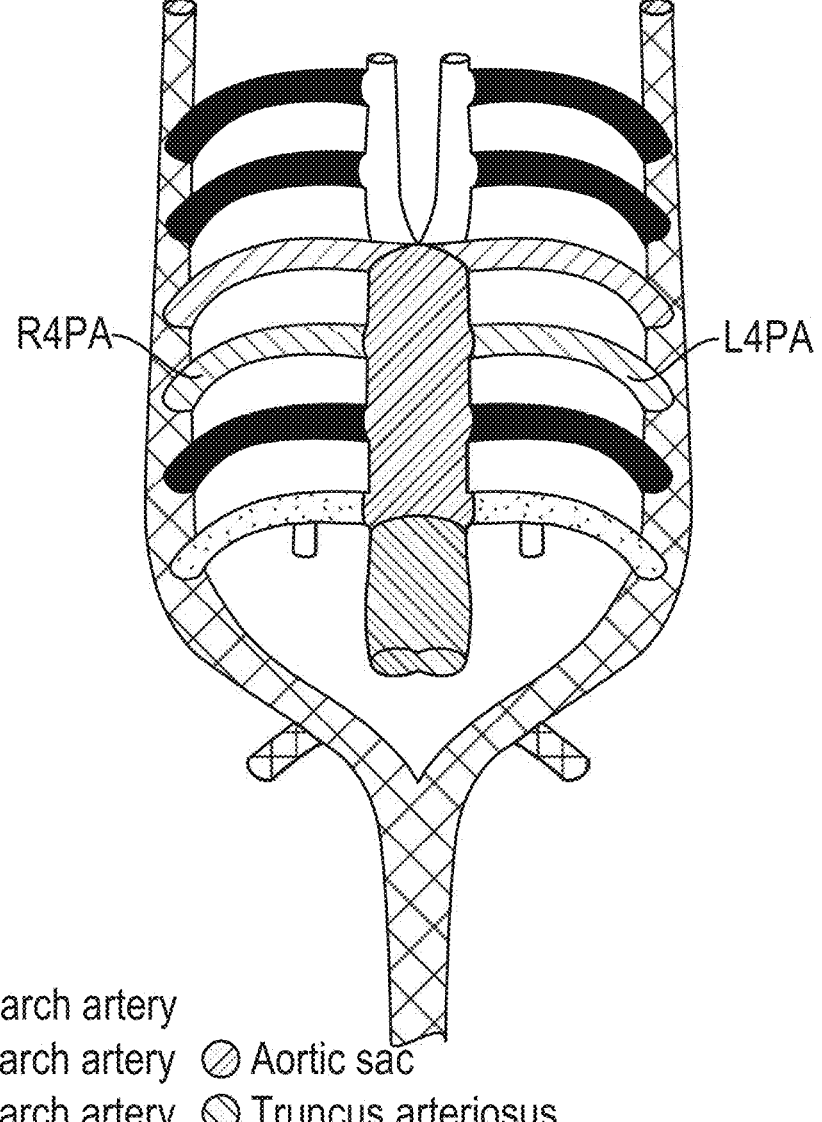
FIG. 5 shows the embryonic anatomy that later develops into the aortic arch.

These "hotspots" of baroreceptors originate from the embryonic pharyngeal arch arteries, shown in FIG. 5. The third pharyngeal arch arteries develop into symmetric structures, the right and left carotid arteries. By contrast, the fourth pharyngeal arch artery on the right (R4PA) becomes the proximal right subclavian artery while the left fourth pharyngeal arch artery (L4PA) develops into the relatively narrow cylindrical strip B of the aortic arch noted in FIG. 6. This strip has distinct features as compared to other regions in the aortic arch.

Figure 6:
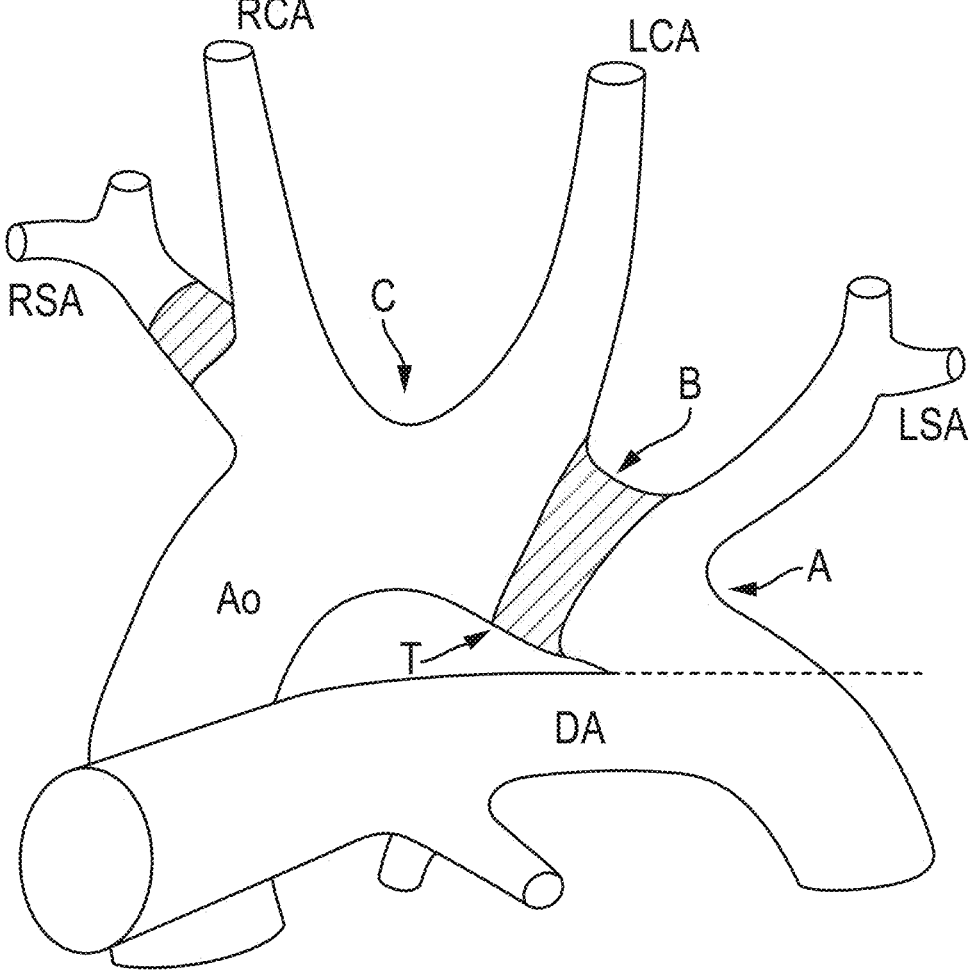
FIG. 6 shows the anatomy of the aortic arch illustrating additional details as to a target region, in accordance with aspects of the invention.
Figure 7:
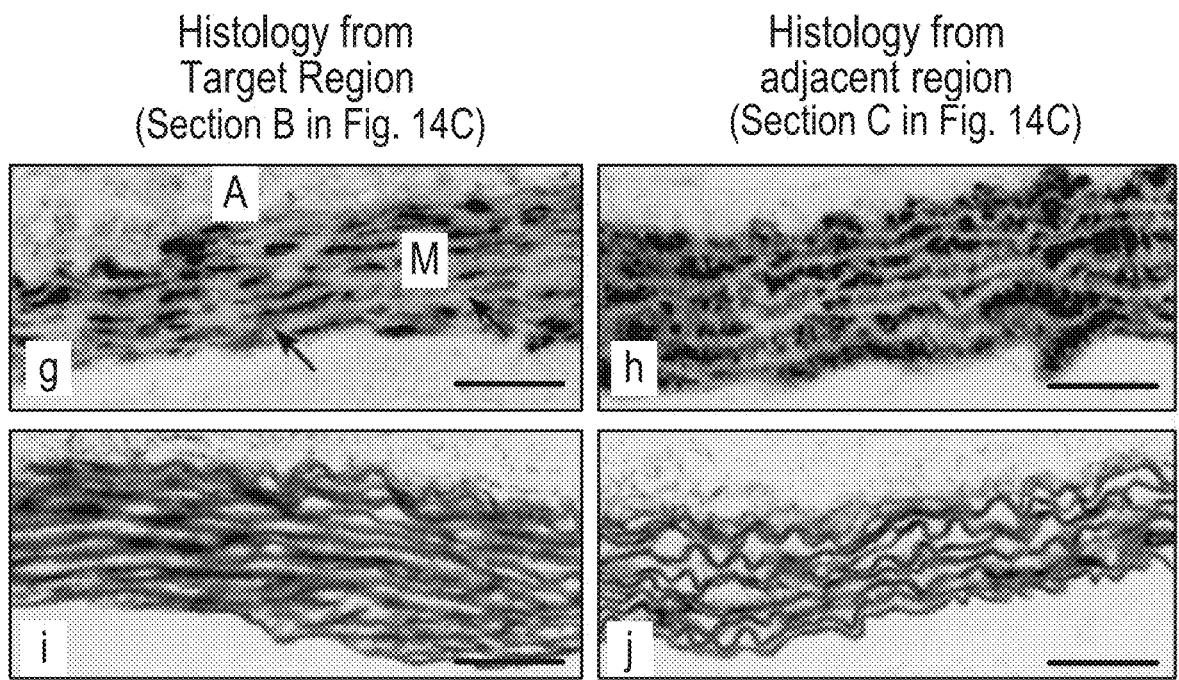
FIG. 7 shows histology of the arterial tissue within the targeted region.
Figure 8A:
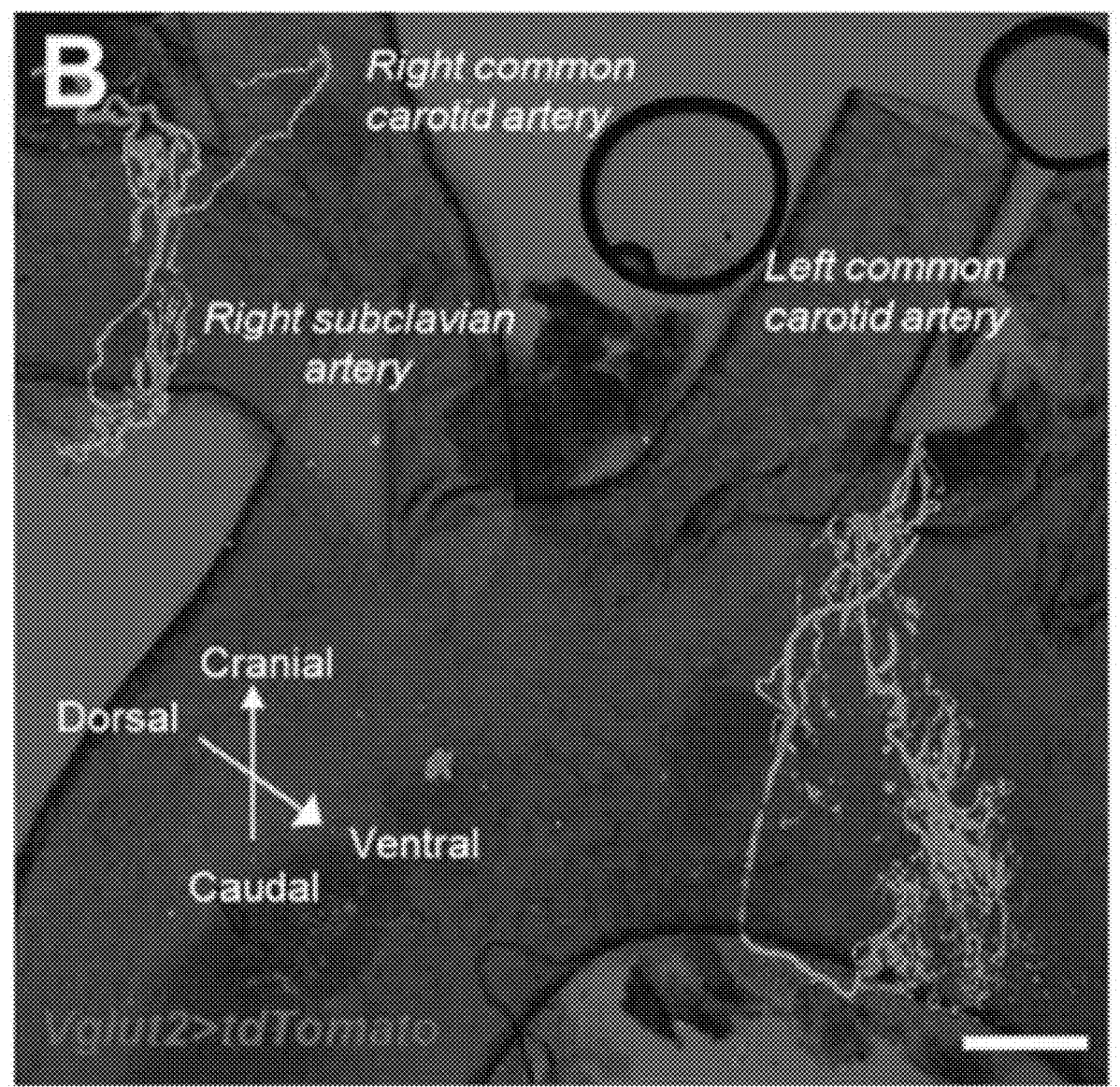
FIG. 8A shows a fluorescence staining image from an animal study illustrating the distribution of baroreceptors in the target region.
Figure 8B:
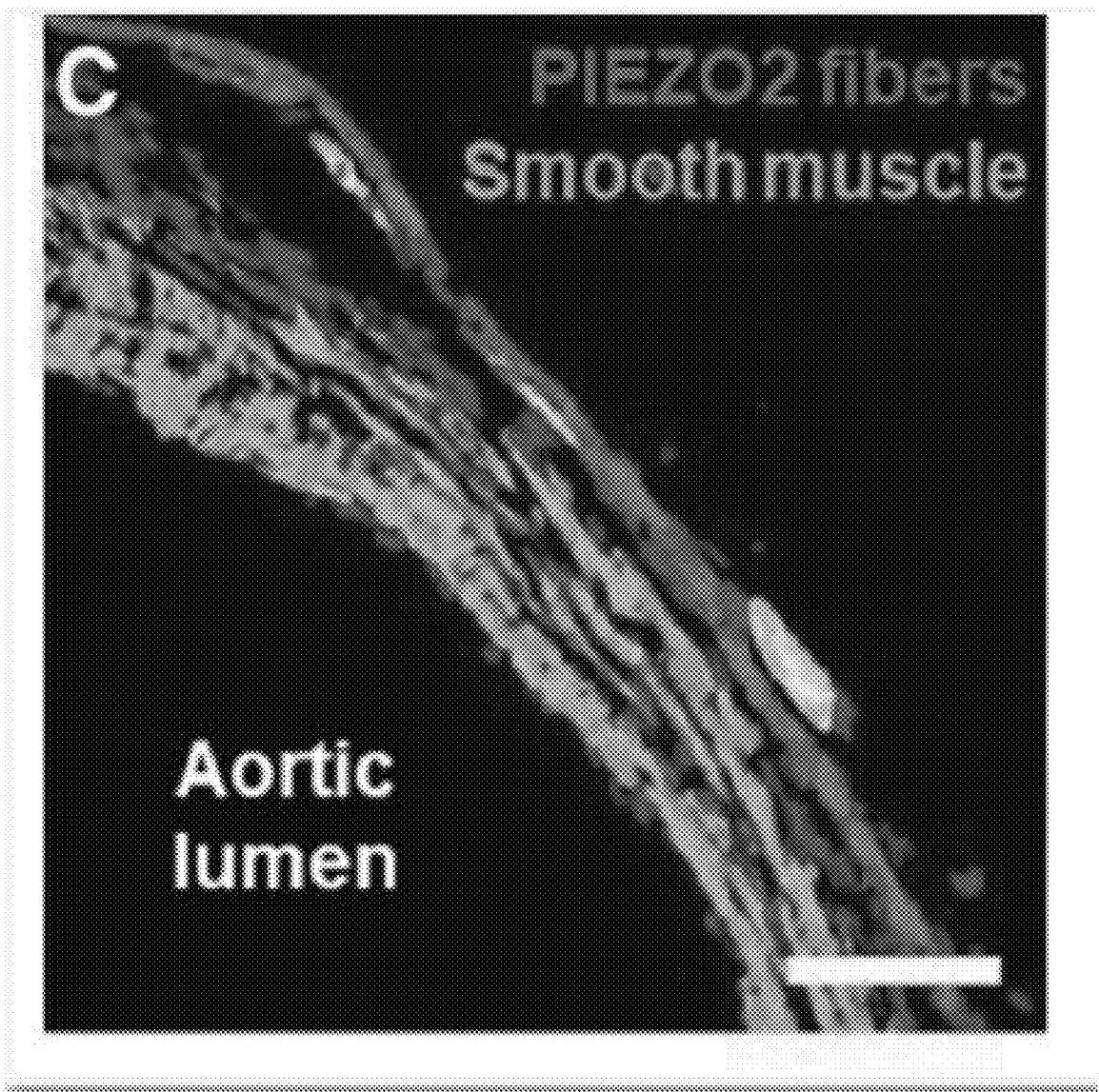
FIG. 8B shows a fluorescence staining image illustrating the location of baroreceptors within the arterial wall of the aortic lumen.

This strip of the aortic arch is histologically distinct from other areas as it has fewer smooth muscle cells and increased elastic lamellae. FIG. 7 shows in the left column, histologic sections through aortic arch segment B, indicating fewer smooth muscle cells and increased clastic lamella as compared to aortic section C in FIG. 6, shown in the right column. It is in this region B that the more commonly known aortic arch baroreceptors are located (as indicated in FIG. 2). However, various animal and human studies have shown there is actually a unique localized distribution of barore-ceptors in this region that extends along the band B that wraps the aortic arch, as shown in FIG. 8A. Additionally, the baroreceptors of the aortic lumen are located on an outer layer of the arterial wall within the aorta, as shown in the fluorescence image of FIG. 8B, which shows the barorecep-tors nerve fibers stained in pink.

Figure 9A:
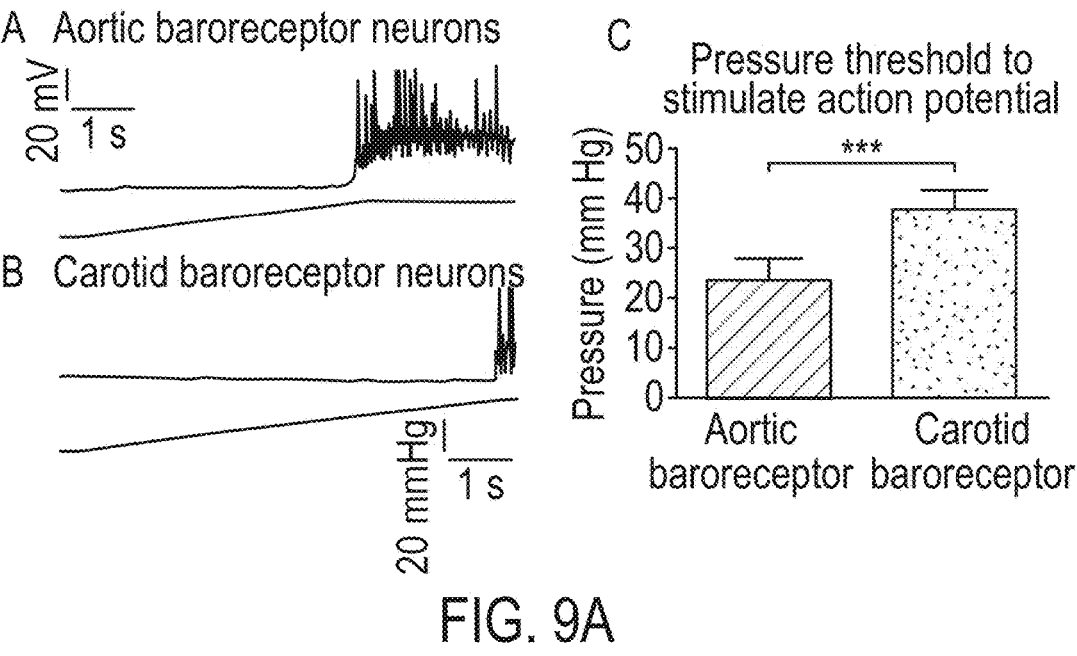
FIGS. 9A-9B illustrate results from an animal study showing heightened sensitivity of the baroreceptors in the aorta as compared to baroreceptors in the carotid.
Figure 9B:
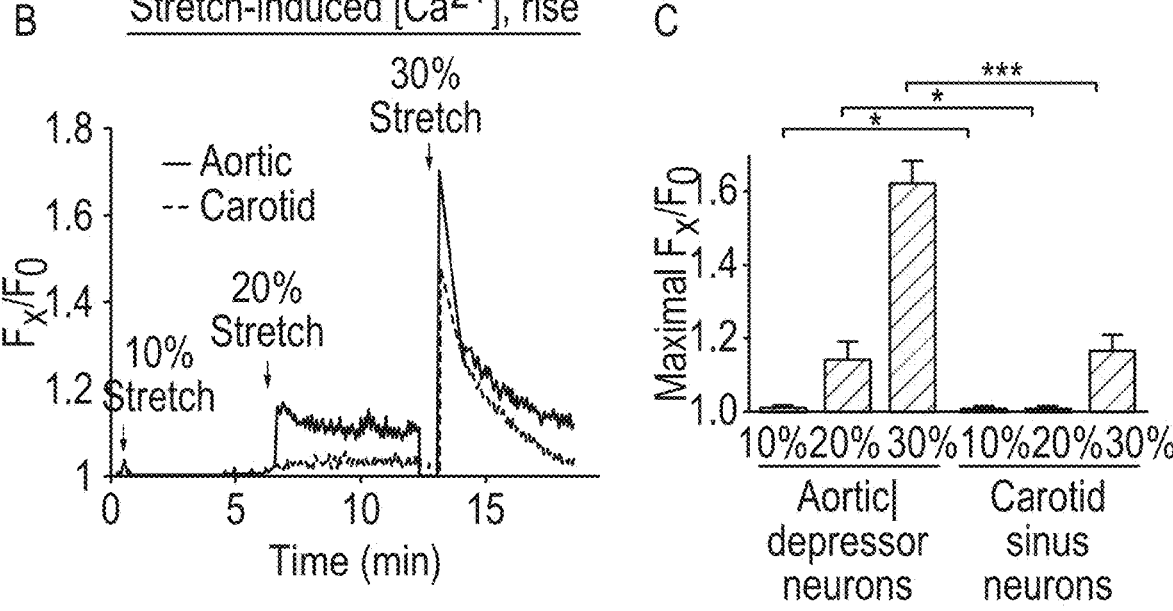

There are very few human reports localizing the aortic arch baroreceptors. One early investigational study indicated baroreceptor nerves wrap the aorta at the original of the left subclavian artery, and the same author later indicated they may extend about the aorta from the brachiocephalic artery to the ligamentum arteriosum. Some early studies have shown that the baroreceptors are found along this region of the aortic arch extending 40% of the circumference. Due in part to the histology of this region noted above, it is believed that the baroreceptors behave differently than baroreceptors in other regions, including the carotid artery. At least one animal study demonstrated that the pressure threshold to stimulate action potential was lower in aortic baroreceptors than carotid baroreceptors, see FIG. 9A. The animal study further suggested that a uniaxial stretch of 20% induced a marked increase in cytosolic calcium fluorescence in the aortic arch baroreceptor neurons but not in the carotid baroreceptor neurons, as shown in FIG. 9B. Thus, it is believed that the aortic baroreceptors in the human aorta are more sensitive than baroreceptors in the carotid arteries. Hence, utilizing an implant specifically configured for deployment within the aortic region to engage and tension the arterial wall in this target region allows for a more consistent pronounced baroreflex response than conventional carotid artery implants. Further, in order to induce a robust and consistent response across the diverse patient population, it is believed advantageous to engage and tension a target zone along a majority of the aorta so as to tension multiple locations along an elongated region to account for potential differences in baroreceptor distributions or activation responses between differing patients.

It is noted that the literature has described the presence of baroreceptors at various locations in the body, including the carotid artery and the aorta, and that some publications describing passive baroreflex implants have mentioned a list of various possible implantations sites in passing, including generally the aorta; however, none have taught any particular target region of the aortic arch. Moreover, none have addressed the unique challenges of implanting in the aortic arch region, challenges which have led the conventional approaches to focus primarily on the carotid artery, which has been commonly accessed to perform certain other procedures, such as placement of carotid stents to address stenosis in this region.

Thus, the present invention seeks not only to provide an improved baroreflex response by implanting at a particular target region in the aortic arch, but also to allow for implantation at this unique site, while improving case of implantation. Importantly, this claimed implant and approach avoids the drawbacks associated with procedures and implantation within the carotid artery, which can undesirably lead to increases in adverse events due to complications in deployment in this area. Additionally, some embodiments seek to tension the arterial walls along an elongate region in the aortic arch, thereby providing a more consistent robust baroreflex response.

While there are marked advantages to delivering the implant in the aortic arch, namely the ability to target the aortic arch baroreceptors in a target region that includes the narrow band that wrap the aorta, there are also certain challenges associated with deployment in this area. Since the aortic arch is considerably larger in diameter than the carotid, the implant diameter must be made to correspond to the diameter in the aortic arch in order to sufficiently engage tissues to achieve the stretching of the arterial walls (e.g., a stretch of 20% or more, 20-50%, or even 20-100%). In one aspect, this stretching can include tension in the arterial walls. In other embodiments, this tensioning can be provided by a controlled reshaping of the arterial walls. Further, to prevent flipping or rotation of the implant, the implant should preferably have a length substantially greater than its largest lateral dimension (e.g., diameter), for example about 25, 30, 40 mm or greater, typically between 30-40 mm. In some embodiments, the implant has a length, such as 60 mm or greater, to engage an elongated target region to provide a more consistent robust baroreflex response. In some embodiments, the length of the entire implant is 70 mm or greater (e.g., about 70-90, 70-80 mm, or about 85 mm).

Another challenge is that the aorta is a main artery within the body such that there is a high volume of blood flow that is carried through the aortic arch as well as into secondary arteries that branch off from the aorta (e.g., BA, LCC, LSA). Therefore, in order to provide consistent engagement and stretching at the target region long term, the implant must be configured to withstand the forces from the pulsatile blood flow through the aortic arch as well as the lateral forces from blood flow directed into the secondary arteries without dislodging. Further, the implant should be configured to expose a majority of the arterial walls in the target region to pulsatile blood flow, so as to provide the sustained blood pressure drop noted above, rather than a transitory response if the arterial walls were isolated from blood flow. In some embodiments, the implant provides sufficient stretch to induce a baroreflex response that drops blood pressure in hypertensive patients by at least 10 mm Hg, 20 mm Hg, 30 mm Hg, 40 mm Hg, 50 mm Hg, or 60 mm Hg or greater. Yet another challenge is that the implant must allow blood flow freely in a lateral direction into the secondary branch arteries. Thus, the implant itself has been configured with major openings in the expandable structures that both allow exposure of the arterial walls and allow lateral blood flow to feed any adjacent secondary arteries.

II. Exemplary Implant Devices

Figure 1A:
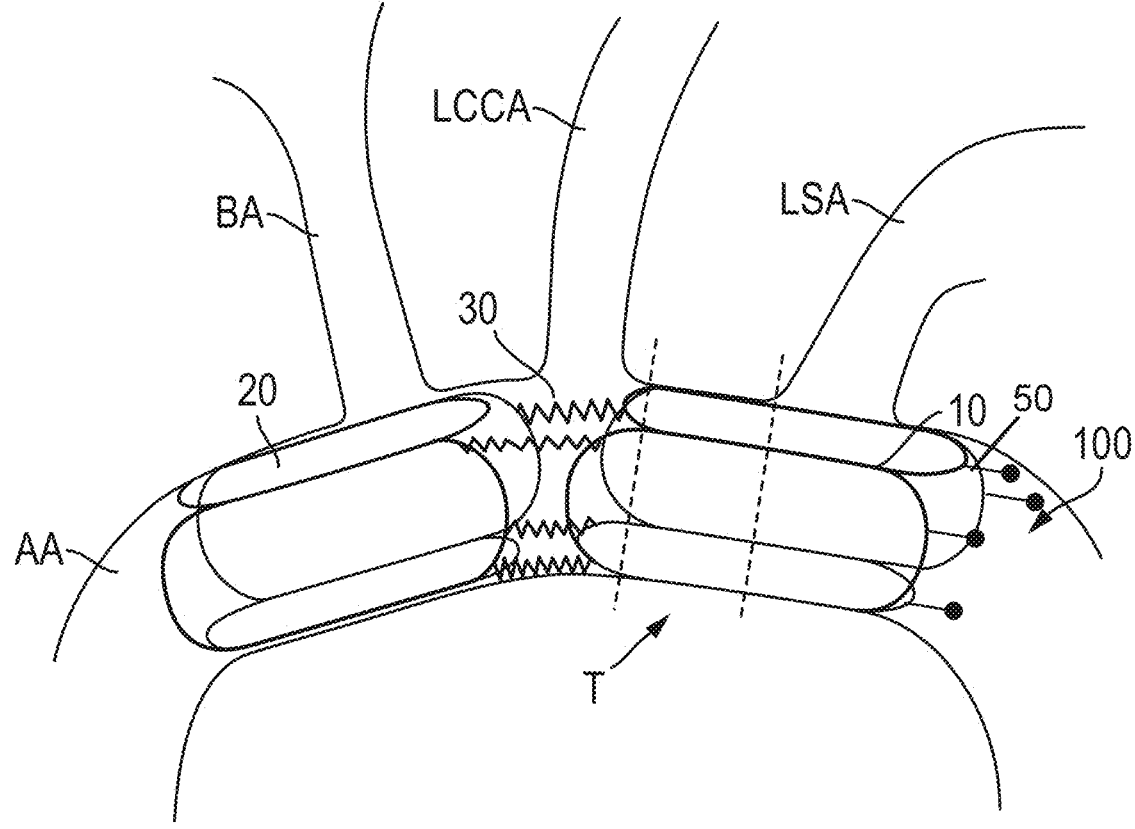
FIG. 1A shows an exemplary implant device deployed along the target region in the aortic arch of a patient, in accordance with some embodiments.

FIG. 1A shows an exemplary implant device 100 for treatment of drug-resistant hypertension that is implanted within the aortic arch AA. The implant is an expandable device inserted into the aortic arch and lowers blood pressure by stretching the aortic arch artery wall from the inside and augmenting the aortic arch baroreflex. Branching from the top of the AA are the secondary branch vessel, the brachiocephalic artery (BA), the left common carotid artery (LCCA) and the left subclavian artery (LSA).

As shown, the implant 100 includes two expandable structures 10, 20 interconnected serially by axially expandable connectors 30. The expandable structures are arranged longitudinally along the aorta, which helps anchor and stabilize placement of the implant within the curved aortic arch. Given the relatively large size of the aorta, the high blood flow rate, as well as the curved morphology, anchoring of a single expandable structure in this region can prove challenging. By utilizing two or more structures disposed along differing portions of the aorta, the implant accommodates the curvature and complex geometry of the aorta to help anchor the implant at the target location. Moreover, by relying on engagement of two or more structures along the aorta, the anchoring forces of the implant are distributed over a larger area, thereby minimizing trauma to the arterial walls, which can reduce inflammation and formation of thrombus that can contribute to formation of atherosclerotic plaques. While shown deployed with the first expandable structure 10 deployed off-center, it is appreciated that the structure could be centered on the target area T. The implant can further include proximally extending tethers 50 to facilitate retraction of a partially deployed implant for removal or repositioning of the implant. As shown, the expandable structures have a non-circular (i.e. square) shape when expanded that reshapes the arterial walls, thereby tensioning the arterial walls along a target region of the aorta. In some embodiments, the implant is sized such that the flattened part of the expandable structures does not touch the arterial walls, thereby promoting a long-term baroreflex response.

Figure 1B:
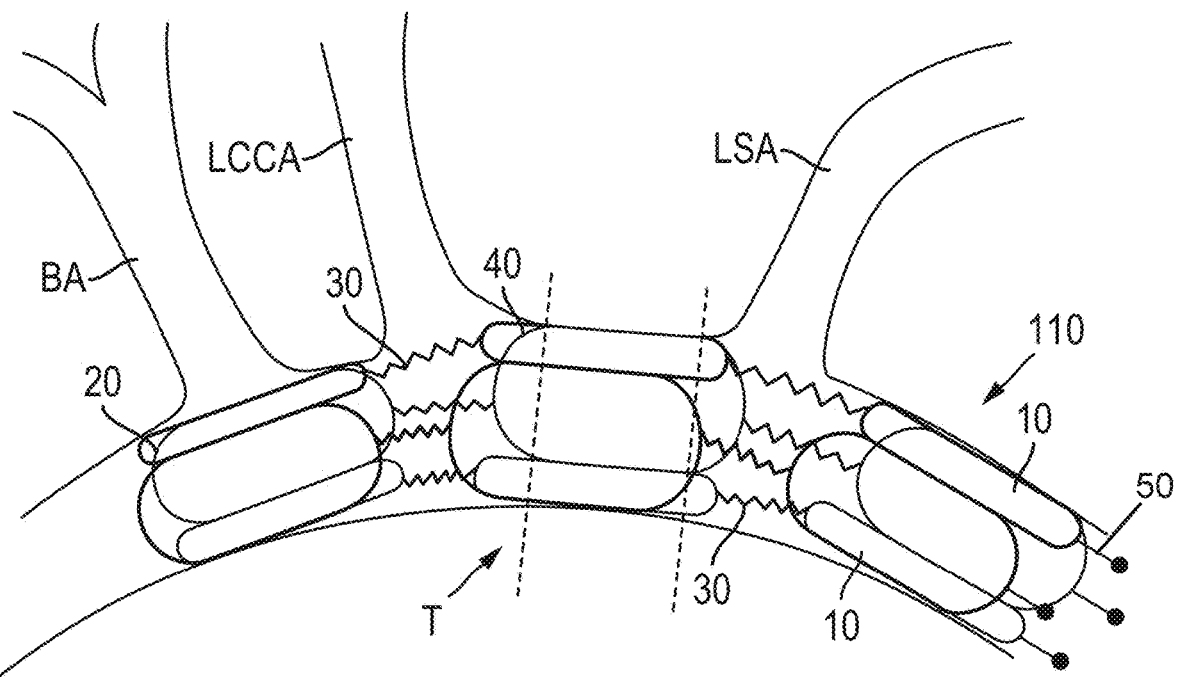
FIG. 1B shows another exemplary implant device deployed along the target region in the aortic arch of a patient, in accordance with some embodiments.

FIG. 1B shows another exemplary implant device 110 for treatment of drug-resistant hypertension that is implanted within the aortic arch AA. This embodiment includes three expandable structures 10, 20, 40 that are interconnected serially by multiple flexible connectors 30. This implant is configured so that the middle expandable structure 40 is deployed at the target region T to active the baroreceptors in this region, while the proximal and distal structures 10, 20 act as anchors providing additional stability and also help transition the arterial wall to the middle expandable structure. As shown, the middle expandable structure 40 can have a lateral dimension that is larger than that of the proximal and distal expandable structures. Typically, the middle structure has a lateral dimension that is larger by 1.2-2 times, preferably about 1.3-1.5 times, that of the proximal and distal structures. This configuration allows for further stretching and reshaping of the arterial wall at the target region since the proximal and distal structures stretch the arterial wall to a lesser degree, thereby helping transition the arterial wall to the increased stretch in the target region. This reduces the risk of dissection along the target region from the increased stretch as the proximal and distal structures distribute some of the forces from stretching at the central region. Further, this configuration provides greater stability of the middle structure at the target region. The implant can further include proximally extending tethers 50 to facilitate retraction of a partially deployed implant for removal or repositioning of the implant. Various other aspects of this implant can be similar or the same as those described in FIG. 1A.

As shown in FIGS. 1A-1B, the expandable structures can be formed by multiple open wire frames formed by spaced apart struts defining each lateral side. The lateral sides of adjacent frames are interconnected along lateral struts so that the frames form a regular polygonal shape, which is axisymmetrical along a longitudinal axis of the expandable structure. It is appreciated that various other expandable structures or connecting bridges could be used, such as those shown in FIGS. 32A and 33A. The expandable structures have a collapsed configuration for advancement through the vasculature (e.g., within a delivery catheter) and an expanded configuration (as shown) in which the lateral struts engage the arterial walls of the aorta, thereby stretching the arterial walls between each pair of struts in a frame sufficiently to induce the baroreflex response. The flexible connectors 30 are axially expandable (e.g., zig zag connectors) to allow the two expandable structures to extend along differing longitudinal axes so as to accommodate varying degrees of curvature and the complex three-dimensional geometry of the aortic arch. By this configuration, distortion of the aorta or the adjacent great vessels is minimized, and compressive injury to surrounding anatomic structures such as the left recurrent laryngeal nerve is avoided. Additional details regarding the expandable structures can be understood by referring to FIGS. 10A-12B. While these embodiments depict implants defined by interconnected frame, it is appreciated that these aspects are applicable to various other types of expandable structures, for example, expandable structures formed by one or more wires or laser cut design formed from a tube.

Figure 1C:
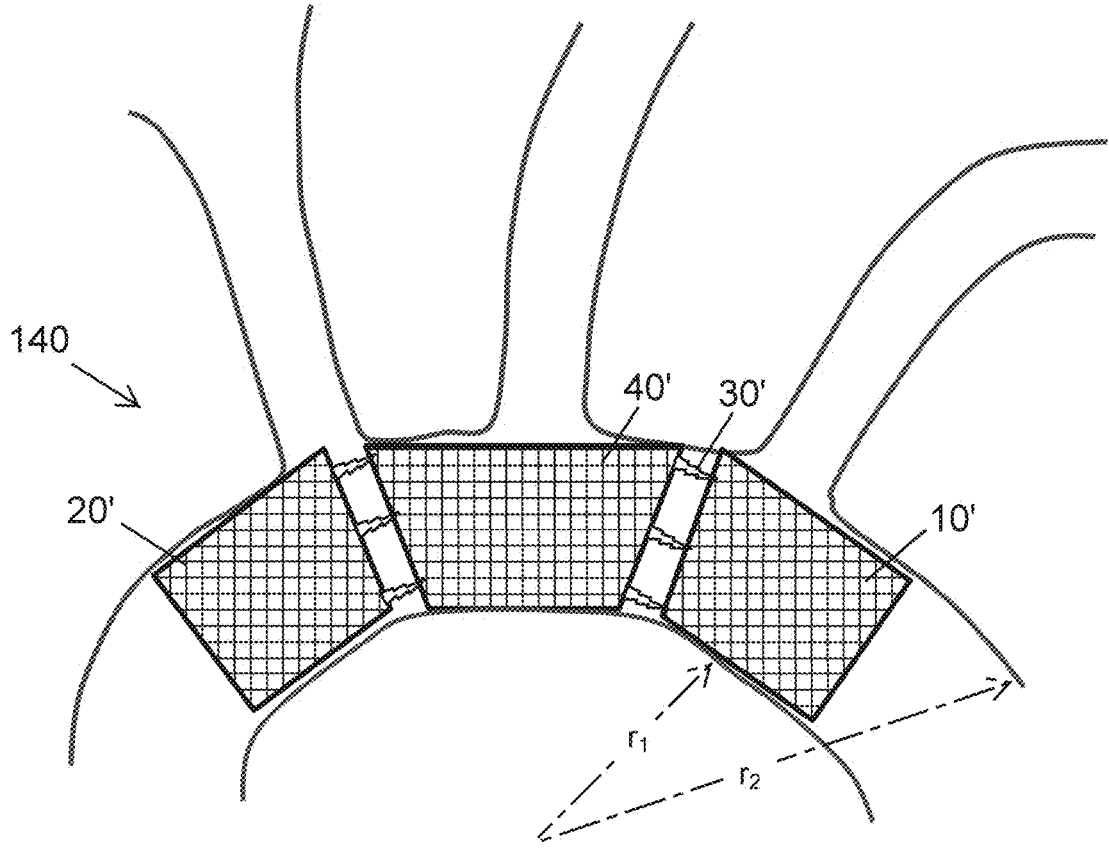
FIG. 1C shows another exemplary implant device deployed along the target region in the aortic arch of a patient, in accordance with some embodiments.

FIG. 1C shows another exemplary embodiment for an implant 140, which has asymmetrical structures that better conform to the curvature of the aortic arch and promote more uniform engagement and tensioning of arterial walls along an elongated target region. As used herein "asymmetrical" refers to the expandable structures non-symmetrical from a lateral side view, for example, a trapezoidal in shape with one side being longer than the other as shown in FIG. 1C. As can be seen, the aortic arch has a substantial curvature, the inside curvature having a radius $r_1$ that is considerably less than a radius $r_2$ of the outer curvature. In prior embodiments, this curvature led to variable gaps between expandable structures and requires more flexible connectors to accommodate these variations. In this embodiment, the implant 140 includes three asymmetrical expandable structures 10', 20', 40' having a greater length on a side positioned along the outside curvature of the aortic arch and a shorter side positioned along an inside curvature of the aortic arch. These asymmetrical expandable structures allow for a smaller, more uniform gap between structures such that connectors 30' can be more uniform in length, which allows use of more robust connector designs than prior embodiments.

Figure 1D:
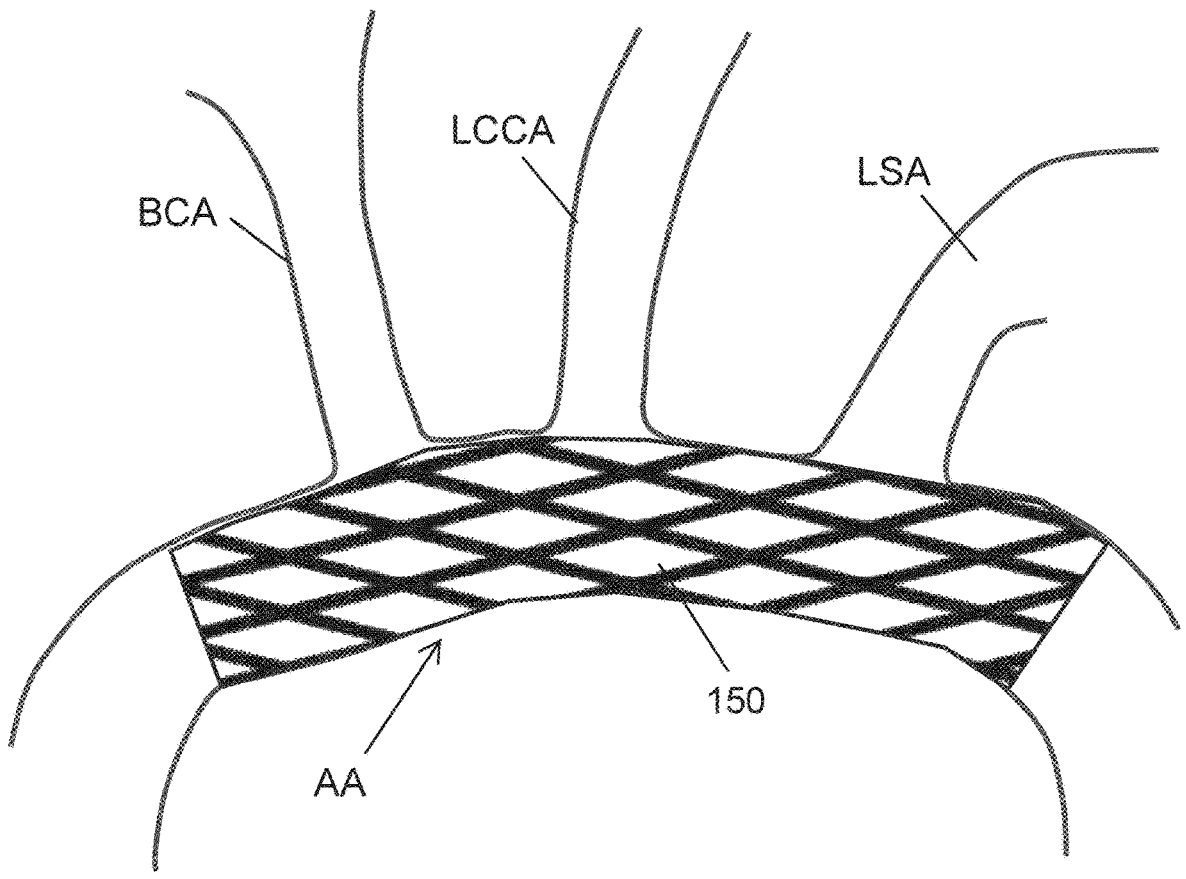
FIG. 1D shows an exemplary implant device deployed along an elongated target region of the aortic arch of a patient, in accordance with some embodiments.

FIG. 1D shows an exemplary implant device 150 for treatment of drug-resistant hypertension that is implanted within the aortic arch AA. In this embodiment, the implant is an expandable device inserted into the aortic arch and lowers blood pressure by tensioning the aortic arch artery walls from the inside with a non-circular (e.g. elliptical, oval) cross-sectional shape, thereby augmenting the aortic arch baroreflex. Branching from the top of the AA are the secondary branch vessels, the brachiocephalic artery (BCA), the left common carotid artery (LCCA) and the left subclavian artery (LSA). As shown, the implant 150 is dimensioned to engage the walls of the aorta sufficiently to reshape the curvature of the walls and is of suitable length to extend along a majority of the aortic arch, at least along a target zone from proximal the brachiocephalic take off to distal of the left subclavian take off. In one aspect, the implant is formed of woven or braided wire to form larger interstitial spaces than in conventional stents, so as to avoid impeding blood flow into lateral arteries and to expose the arterial walls to pulsatile blood flow to maintain a long-term response. In some embodiments, the implant can be laser cut from a tube. In some embodiments, the implant is sized such that the more flattened part of the implant does not touch the arterial walls, at least during a portion of the cardiac cycle, thereby promoting a long-term baroreflex response.

Figure 10E:
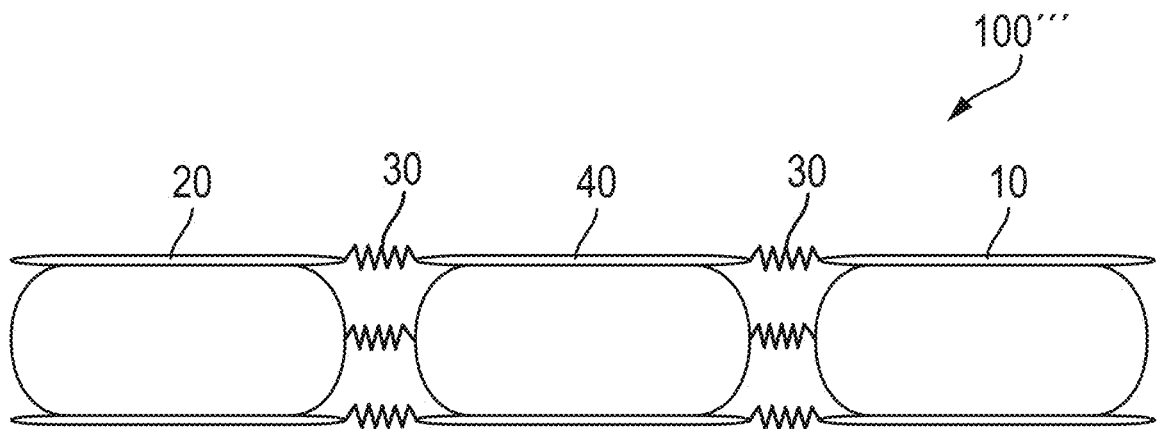
FIG. 10E shows an exemplary implant having three expand-able structures in accordance with some embodiments.
Figure 13B:
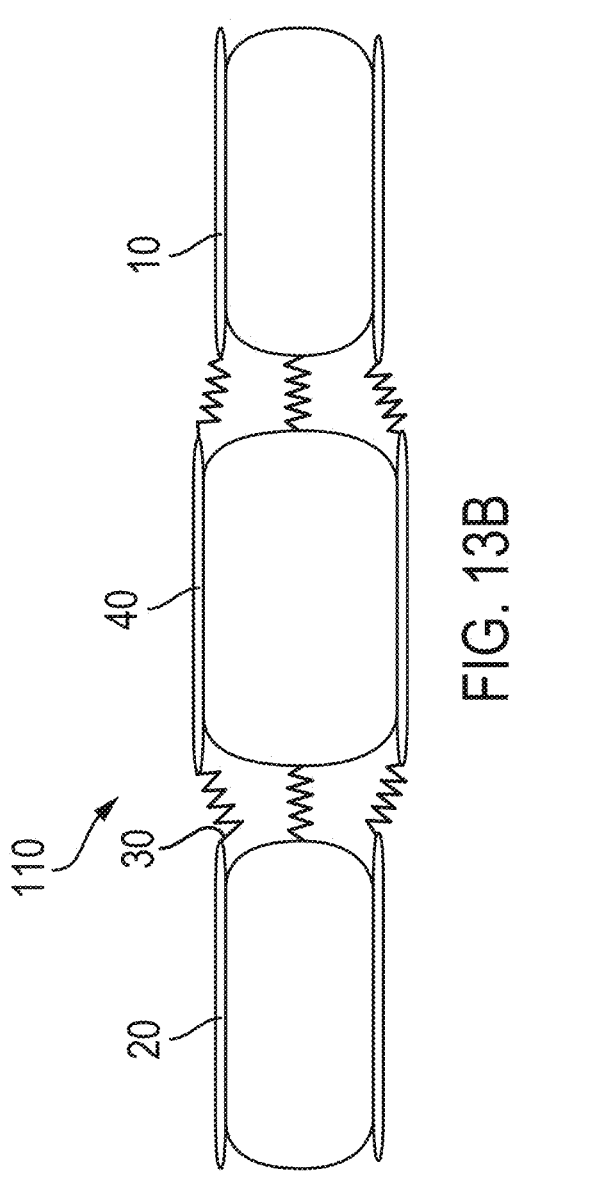
FIGS. 13A-13D show an alternative embodiment of the implant having three expandable structures where the middle structure has an increased lateral dimension, in accordance with some embodiments.
Figure 13D:
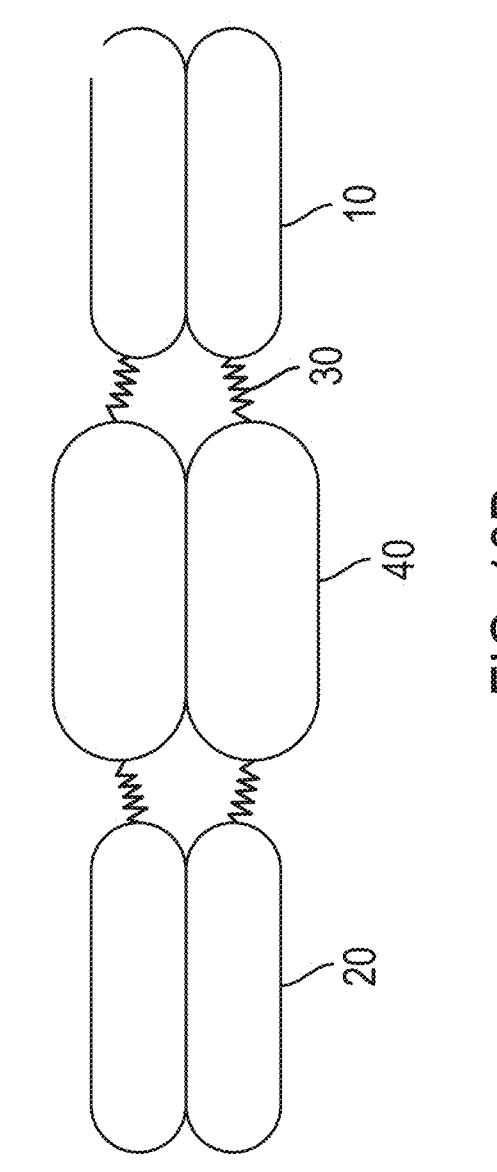
Figure 13A:
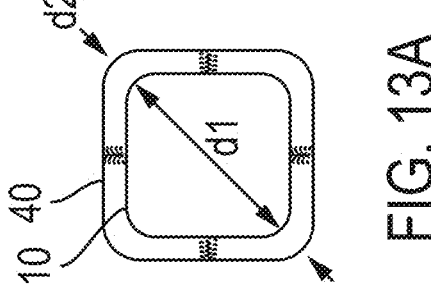
Figure 13C:
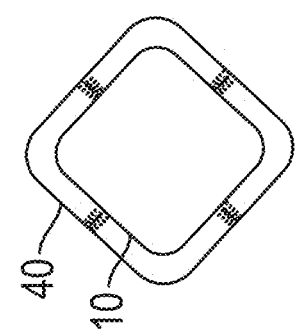

FIGS. 10A-10D shows the exemplary implant device 100 having two laterally expandable structures 10, 20 that are interconnected serially by multiple flexible connectors 30. FIG. 10A shows the cross-sectional view, while FIG. 10B shows a lateral side view. FIGS. 10C-10D show the same views but with the device rotated by 45 degrees along a longitudinal axis. The implant device can further include one or more visualization markers 31 thereon, for example a coating on the flexible connectors 30 or gold or platinum spots, to aid in positioning during implantation. In this embodiment, the flexible connectors are axially expandable (e.g., zig-zag connectors) and there are four connectors in total extending between the apex of adjacent crown portions of the first and second expandable structures. FIG. 10E shows exemplary implant device 100''' having three laterally expandable structures 10, 20, 40 that are interconnected by flexible connectors 30. It is appreciated that some embodiments can further include additional such structures (e.g., 4, 5, 6, etc.) connected in the same or different manner.

In this embodiment, each expandable structure 10, 20 includes four elongated frames (10a/10b/10c/10d) joined along adjacent lateral sides to form a square cross section, as shown in FIG. 10A. Each frame includes at least two linear strut sections 11, 12 defining opposing lateral sides and curved atraumatic crowns 13,14 connecting the proximal and distal ends, respectively. Accordingly, the overall shape of the frame is oblong or pill-shaped. As shown, the atraumatic crowns 13, 14 are gently curved forming an arc of a half-circle or less so that engagement of the proximal or distal ends against tissues does not cause trauma to the arterial wall. The struts and crowns define the overall frame, which leaves a major opening 15 through which the arterial wall is exposed to pulsatile blood flow and which allows lateral blood flow into secondary branch arteries. In some embodiments, the struts of adjacent frames are defined as a single strut, such that a square-cross sectional implant would have only four total struts, one strut on each corner. It is further noted that the entire frame can be formed as a single continuous wire such that the crowns and struts are differing portions of the same wire. In some embodiments, the frames are designed to avoid any sharp corners or angled features of less than 100 degrees, which ensure the proximal and distal ends of the frame remain atraumatic and helps avoid formation of thrombus or plaques within the frame along the major openings through which lateral blood flow is maintained. This design is advantageous as the square cross-section provides sufficient engagement of the arterial walls between the opposite side struts of each frame to stretch or reshape the artery walls without overstretching any one portion of the arterial wall, yet still retains normal function and blood flow of the aorta. Although this embodiment includes two expandable structures interconnected by four flexible connectors, the implant could include additional expandable structures connected serially in the same fashion and could include more or fewer flexible connectors.

It is understood that these concepts can be utilized in various other shapes/designs, for example triangular or any regular polygonal cross-section, such as those shown in FIGS. 11A-13D. FIGS. 11A-11B show an implant 100' with first and second expandable structures 10'/20', each having similar frames as those in FIG. 10A, except each component is formed by three frames such that the cross-section is triangular (e.g., an equilateral triangle). In this embodiment, the largest lateral dimension of the component would be the length of each side of the triangle, which stretches three portions of the arterial wall. FIGS. 12A-12B show yet another implant 100'' having first and second expandable structures 10''/20'', each formed by similar frames as those in FIG. 10A expect each component is formed by five frames to form a hexagon, which stretches five portions of the arterial wall. In this embodiment, the largest lateral dimension would be a distance between an apex and a midpoint of an opposite side. FIGS. 13A-13D show implant 110 (see FIG. 1B) having three expandable structures 10, 20, 40, where the middle expandable structure 40 has a lateral dimension d2 that is larger than the lateral dimension d1 of the proximal and distal expandable structures 10, 20. Dimension d2 can be larger than d1 by 1.2 to 2 times, preferably about 1.3-1.5 times larger. In this embodiment, dimension d2 is 1.3 times larger than d1. As discussed previously, this configuration further improves stability of the implant device in the aortic arch and advantageously allows for further stretching or reshaping of the arterial walls of the target region than would otherwise be safely performed. This is made feasible by utilizing the proximal and distal expandable structures to transition the arterial walls and reduce the risk of dissection or tearing beyond the target region.

In another aspect, the implant is sized specifically for the dimensions of the human aortic arch so as to engage the arterial walls with the lateral struts of the expandable structure so as to anchor the implant within the aortic arch and sufficiently stretch or reshape the arterial walls within the target region. In the embodiment shown in FIG. 1, the implant is positioned so that the first expandable structure 10 is positioned opposite the LSA along the target region of the cylindrical band wrapping the aorta, as noted previously. Thus, engagement of a pair of lateral struts in this region stretches the arterial wall and stimulates the highly sensitive baroreceptors in this region. In some embodiments, the implant is sized to achieve a 2:1 implant-to-aorta diameter ratio at the baroreceptor target zone.

III. Sizing of Implant for Aortic Arch

The baroreceptor amplification device is an endovascular implant designed to amplify the baroreflex response by stimulation of highly sensitive baroreceptors in a precise location within the aorta. This is accomplished by appropriately sizing the implant as described herein to achieve sufficient stretch (e.g., at least 15%, typically 20% or more) of the arterial wall within the target region. The implant is dimensioned based on the unique morphology of the aortic arch in humans. In some embodiments, the applicable dimension suitable for such an implant have been determined by a computed tomography angiographic (CTA) study of human aortas. Measurements of the aortic arch CTA were obtained from 50 patients, including both men and women between the ages of 53 and 88. The measurements were tabulated and the means and range were determined per Tables 1 and 2 below.

Figure 14A:
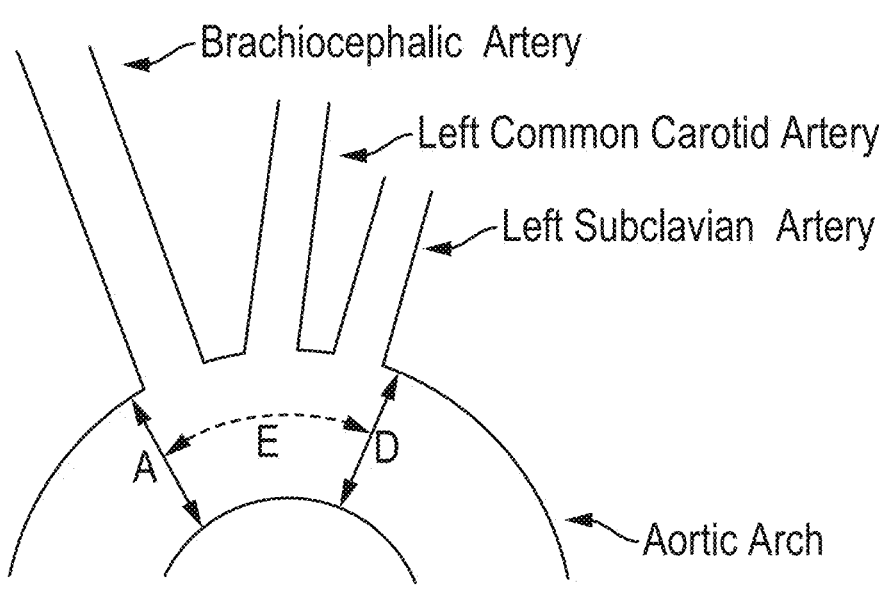
FIG. 14A-14C show various dimensions and features of the aorta that were examined in a patient study to determine appropriate sizing of the implant structure for deployment in the aorta.
Figure 14B:
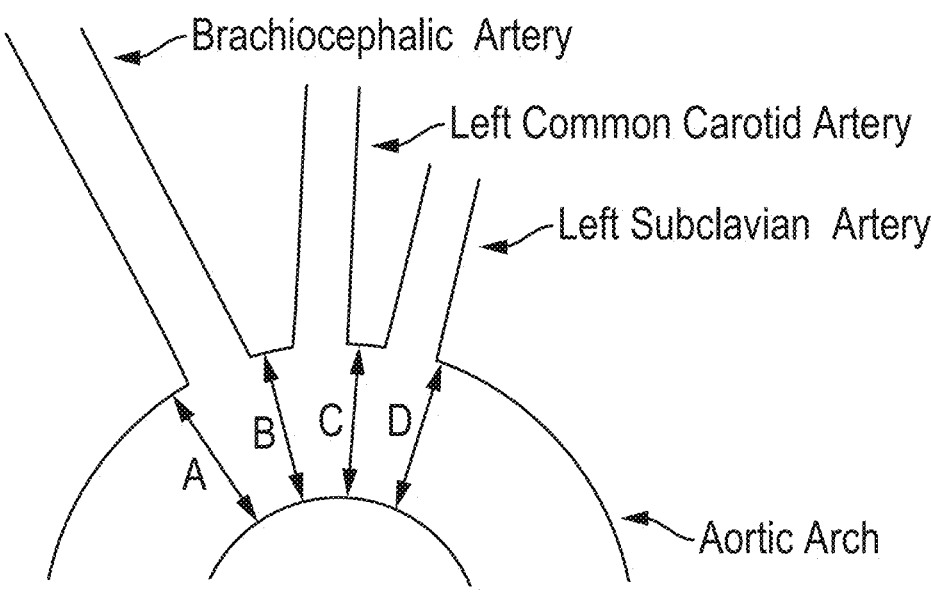

Table 1 shows the mean of various aortic arch measurements, including the aortic arch diameters along regions A, B, C, D (see FIG. 14B) and length E extending between sections A and section D (see FIG. 14A).

TABLE 1

| | | Mean Aortic Arch Measurements<br>Mean ± Standard Deviation (cm) | | |
|---|---|---|---|---|
| A | B | C | D | E |
| 3.08 ± 0.32 | 2.73 ± 0.29 | 2.44 ± 0.28 | 2.33 ± 0.29 | 3.57 ± 0.64 |

Table 2 shows the range of various aortic arch measurements, including the aortic arch diameters along regions A, B, C, D and length E noted above.

TABLE 2

| | | Ranges of Aortic Arch Measurements<br>Range (cm) | | |
|---|---|---|---|---|
| A | B | C | D | E |
| 2.54-3.79 | 2.08-3.52 | 1.85-3.03 | 1.87-2.89 | 2.38-5.14 |

Figure 14C:
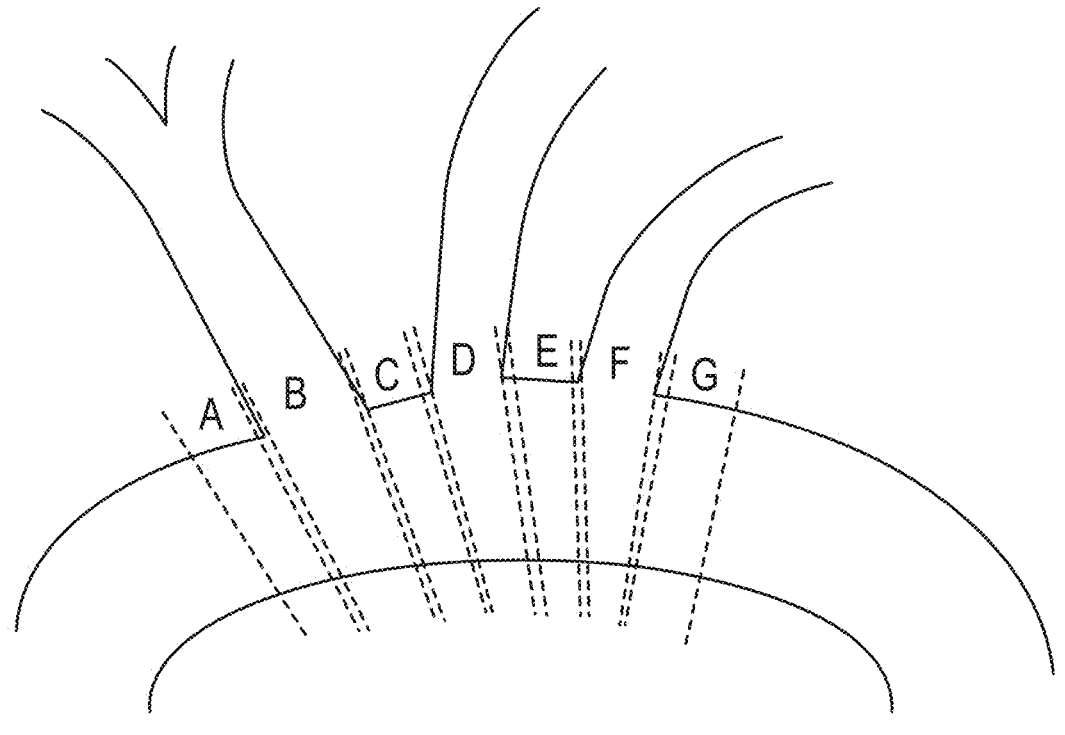

In one aspect, the diameter and length dimensions could be considered to display relatively little variation as demonstrated by the small standard deviations and narrow ranges. As shown in FIG. 14C, the aortic arch region has multiple distinct regions where portions of an implant device may potentially be implanted or anchored by one or more portions of the implantable device. Thus, the implant device design should accommodate not only the target region (e.g., typically region E), but may include proximal and distal expandable structures configured to engage the inside diameters along more proximal regions (e.g., region F or G) and more distal regions (e.g., regions A-D) as well. Thus, it is considered that an appropriately sized implant could be made to fit most patients within the above noted ranges. It is noted that arterial walls may be safely stretched up to 50%, potentially up to 100% in healthy patients, such that variability of stretch due to differences in aortic dimensions may be acceptable, so long as the target region is sufficiently stretched (e.g., by at least 20%). In the alternative, it could be considered that these means and ranges of dimension warrant differing sizes of implants. In some embodiments, a set of differently sized implants (e.g., 3-10 different sizes) could be provided and a size could be readily selected based on the particular measurements of the aortic arch of a given patient (see Table 3 below). In another alternative, an implant could be custom-made according to the unique measurement of a patient. The latter two options may be well suited for patients with highly variable morphology or particularly complex geometry of the aortic arch.

In accordance with the above noted means and ranges of the human aorta, the two or more expandable structures can be suitably dimensioned for placement in the aorta. In an exemplary embodiment, each of the expandable structures are between 30 and 60 mm in length, typically about 40 mm in length, and the greatest lateral dimension (e.g., diameter) is greater than 25 mm, such as between 30 and 55 mm, typically between 30 and 46 mm. These dimensions accommodate a majority of aortas in the average adult human while providing the requisite reshaping along the target region to induce the baroreflex response. The expandable structures can be of the same length or of differing lengths and can be the same or differing diameters.

Table 3 below shows a set of differing sizes of implants and associated diameters based on a tabulation of the relevant dimensions of aortic arches of over 50 patients per the CTA study. Component A refers to the more distal expandable structure (20 in FIG. 1), and component B refers to the more proximal expandable structure (10 in FIG. 1A) disposed at the target region. As described above, the size of implant can be selected for the unique morphology of a patient based on a CT scan of the patient's aortic arch. It is appreciated that a set of sizes could include any of the sizes noted, or any combination thereof, as well as various additional combinations not listed.

TABLE 3

| | Size of Implant Configurations (Diameters) | |
|---|---|---|
| Size | Component A | Component B |
| 1 | 30 mm | 30 mm |
| 2 | 30 mm | 34 mm |
| 3 | 30 mm | 38 mm |
| 4 | 34 mm | 34 mm |
| 5 | 34 mm | 38 mm |
| 6 | 34 mm | 42 mm |
| 7 | 38 mm | 38 mm |
| 8 | 38 mm | 42 mm |
| 9 | 38 mm | 46 mm |
| 10 | 42 mm | 42 mm |
| 11 | 42 mm | 46 mm |
| 12 | 42 mm | 50 mm |

In another aspect, the two or more expandable structures are connected serially by multiple flexible connectors. Preferably, the connectors are axially expandable (e.g., zig-zag design) to optimize conformity to the outer and inner curvatures of the aortic arch. In some embodiments, the connectors are axially expandable by 5-20 mm, typically about 5-10 mm. In some embodiments, the connectors are between 5 mm unexpanded and up to about 10 mm or more fully expanded so that the connectors on the outer curvature of the aortic arch can be expanded while the connectors on the inner curvature of the aortic arch can remain unexpanded, as shown in FIGS. 1A-1B.

In another aspect, the length of each expandable structure is typically between 30 and 50 mm, preferably about 40 mm, such that the overall length of the entire implant including the flexible connectors is between 65 and 110 mm, typically between 70-90 mm depending on the axial extension of the connectors. These lengths allow the implant to extend a minimum of 10 mm beyond both the lateral aspects of the brachiocephalic artery and the lateral aspect of the left subclavian artery to ensure a safe and stable loading zone for the device. Based upon the CTA study, implant is about 85 mm when the connectors are unexpanded and approximately 10 mm or greater (e.g., 10-20 mm) when the connectors are fully expanded.

Based on previous animal studies, it was believed that human aortic arch baroreceptors need to be stretched a minimum of about 20% to achieve a significant increase in baroreceptor nerve signaling. Stretching of the artery walls is often associated with reshaping that is believed to impart tension in the arterial walls that induce a baroreflex response. It is understood, that in some embodiments, tension may be induced by sufficient reshaping, even when stretching is less than 20%. Notably, tension of 20% or greater may be achieved by sufficient reshaping considering the gradient in tension through the wall thickness of the aorta, related to localized shape change or deformation. See for example, the discussion further below in regard to FIGS. 48B-48C. Consequently, the implant is dimensioned with a greatest lateral dimension or diameter that is a minimum of 20% greater than the natural diameter of the target region (e.g., measurement C from the CT angiographic study) and configured in a manner to reshape the walls to impart sufficient tension in the arterial walls to induce the baroreflex response. In some embodiments, the greatest lateral dimension is about 25 mm or greater, since the minimum human aorta diameter is about 25 mm. In some embodiments, the greater lateral dimension is within a range of about 30-60 mm. In some embodiments, the lateral dimension is constant along a length of the implant. In some embodiments, the lateral dimension is variable (e.g. greater along a middle portion for improved transition, or tapering to match the variation in aorta diameter along the arch). The diameter of the implant should be sufficient to ensure adequate aortic arch wall apposition at the terminal landing zones just beyond the lateral take-offs of the brachiocephalic and left subclavian arteries (e.g., locations A and D in FIG. 13) to ensure sufficient tensioning of the arterial walls. For sizing purposes, the diameter of the implant is measured as the largest lateral dimension (e.g., for a square cross-section, the diagonal shown in FIG. 10A). Based upon the CTA study, the implant can be sized in various differing diameters, for example, 30, 34, 38, 42, 46, and 50 mm. The implant can be constructed with components A and B of differing diameters, for example as shown in Table 4.

IV. Mechanism of Action

To further understand the sizing of the implant, the mechanism of action by which the implant reduces blood pressure should be understood. It is helpful to consider the aortic arch as a circle in cross-section and to consider the arterial wall in discrete arc lengths, as determined by the figure and the arc length formula shown in FIG. 15A. In the case of an implant having a square cross-section (as in FIG. 10A), the aorta diameter is considered to be a circle divided into equal parts (e.g., four equal parts). If the aortic arch diameter is 25 mm then the radius would be 12.5 mm and each arc length would be 19.6 mm, as shown in FIG. 15B. Following insertion of a 30 mm diameter implant with this same example, the aortic arch radius would be 15 mm and each arc length would be 23.6 mm, but only if the aortic arch remained circular, as show in FIG. 15C.

Accordingly, the change in arc length from baseline (FIG. 15B) to post-implant (FIG. 15D) would be an increase of 20% since the radius increases 20% while the other variable stays the same. In other words, each arc of the aorta would be stretched by 20%. However following insertion of the implant, the aortic arch does not remain circular. It is considered that stretching and reshaping of the arterial walls in this manner imparts sufficient tension in the arterial walls to induce a robust baroreflex response. The radius of curvature of each arc increases, while at the same time the central angle corresponding to that arc decreases (see FIG. 23C). The change of these two variables in opposite directions confounds an exact estimate of the resultant arc length and the extent of the aortic arch stretch, however, this approach provides a reasonable enough estimate of the stretch obtained to appropriately size the implant to achieve at least 20% stretch. It is noted that the analysis above assumes the square cross-section of the implant in FIG. 10A, but this analysis could be modified to account for the implant in FIG. 11A that would divide the cross-section into three equal parts or the implant in FIG. 12A which divides the cross-section into five equal parts.

Thus, by the above approach, the implant can be dimensioned to provide at least a 20% stretch and/or reshaping of the target arterial wall. In some embodiments, the implant may be slightly oversized to ensure at least a 20% stretch or to accommodate variations in aorta sizes while still ensuring at least a 20% stretch and/or reshaping in all cases. In some embodiments, the implant can be configured to provide additional stretch, for example, 20-30%, 50% stretch, even a 100% stretch and/or reshaping may be safely performed in many patients.

As noted previously, this design allows the device to be deployed and stabilized at a prime anatomic target within the vasculature. Preferably, this target location is within the aortic arch to stretch and/or reshape the aortic arch baroreceptors located along an elongated target region that includes a cylindrical segment of the aortic arch that wraps the aorta between the take-offs of the left common carotid and the left subclavian arteries (including along the inner curvature) from the human aortic arch CT angiographic study. The aortic arch baroreceptors extend along the inner curvature of the aortic arch and extend circumferentially around the arch to the outer curvature or saddle region of the arch, but the greatest concentration of these baroreceptors is located on a segment adjacent the left subclavian artery on the aortic arch that wraps the aorta along diameter C, which is shown as target T in FIG. 16. The implant configuration described herein is specifically configured to target this location but also to stretch or tension adjacent baroreceptors as much as is safe and possible.

V. Delivery and Placement at Target Region

In yet another aspect, the implant device is especially suited for intravascular delivery and deployment since the implant has a collapsed configuration for advancement through the vasculature and an expanded configuration for engaging the arterial walls, as shown in FIGS. 1A-1D. In the collapsed configuration, the implant is disposed in a delivery catheter to facilitate intravascular delivery to the target site at the aortic arch and subsequent deployment.

In an exemplary embodiment, the implant is a self-expandable structure that is preloaded into a sheathed delivery catheter, as shown in FIG. 17. As shown, the intravascular delivery catheter is designed to deliver the implant in the collapsed configuration, and to position and deploy the implant at the target location, such as that shown in FIG. 16. The delivery catheter includes an internal guidewire lumen so that it can be advanced along a guidewire GW positioned in the aortic arch. In the embodiment shown, the delivery catheter 200 includes a catheter shaft 201 on which the implant 100 is collapsed, and over which is disposed a retractable sheath 202 that constrains the implant in the collapsed configuration until the implant is positioned at the desired target location, for example by visualization of a marker (e.g., radiopaque or ultrasound marker). It is appreciated that the catheter could include any other implant described herein, such implants 110, 120, 130, 140. The marker can be a coating or marker attached to the connectors, and/or either or both of the expandable structures. In some embodiments, the connectors may be made from a differing material than the frames so that the connectors themselves are distinctly visible through visualization techniques. The marker can also aid in identifying and controlling the rotational orientation of the implant during delivery and deployment. The delivery catheter can further include a distal tip 203 to guide advancement over the GW and a flush port 211 for flushing before, during or after delivery. The delivery catheter includes a handle 210 by which the clinician can retract the sheath to deploy the self-expanding implant. Typically, the overall length (I) of the delivery catheter is between 100-150 cm (e.g., about 135 cm) so as to readily access the aortic arch by insertion of the catheter through the femoral artery. The shaft 201 can be rotationally controlled to aid in orienting the implant, such as the implant of FIG. 1C utilizing asymmetric expandable structures.

In some embodiments, the delivery catheter can be configured to deliver the entire implant upon retraction of the sheath, deploying both the first and second expandable structures in rapid succession. The length of the expandable structure is sufficient such that the expandable structure 10 is deployed at the target location despite any minor axial movement upon deployment. Although structure 20 is deployed first, the positioning and deployment is targeting the deployment of structure 10 at the target location. In other embodiments, the delivery catheter can be configured to allow incremental retraction of the sheath by specified distance so as to deliver the expandable structures sequentially, first placing the second, more distal structure, then positioning the first expandable structure precisely at the target location, the axially expandable connectors provide some leeway as to the positioning of the last deployed expandable structure. In still other embodiments, the implant may be balloon expandable and disposed in a collapsed configuration on a balloon of the delivery catheter, the balloon suitably dimensioned for expansion in the aorta to expand and deploy the implant in the target region.

Upon deployment, the implant forms an open lattice with the struts of the frames designed to stretch and/or reshape the aortic arch and stimulate the aortic arch baroreceptors, thereby lowering blood pressure, while the arterial wall is exposed to each aortic pulsation through the major openings of the frames, as shown in the example embodiments in FIGS. 10A-12B.

Figure 18A:
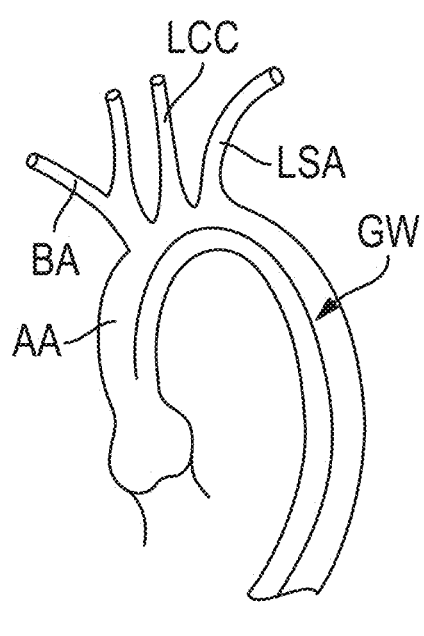
Figure 18B:
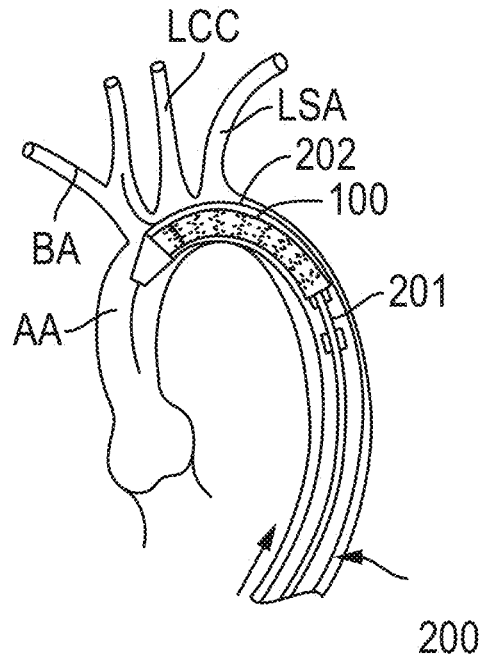
Figure 18C:
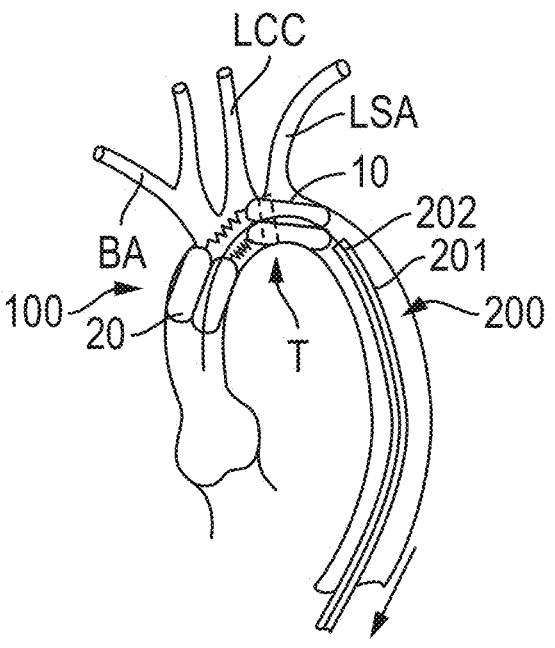
Figure 18D:
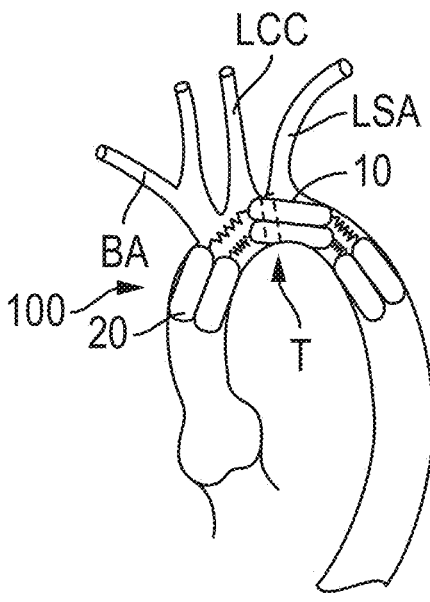

FIGS. 18A-18D illustrate sequential steps of an exemplary method of treating hypertension by deploying the implant device described herein. As shown in FIG. 18A, a guidewire GW is advanced through an entry point (e.g., the femoral artery) and advanced through the vasculature and into the aortic arch. Visualization techniques, such as fluoroscopy, can verify placement of the GW in the target region. As shown in FIG. 18B, the delivery catheter 200 is advanced along the GW, the catheter having an implant 100 disposed in a collapsed configuration on a catheter shaft 201 and constrained within a retractable outer sheath 202. Once the implant is positioned at the desired target location within the aortic arch, the outer sheath 202 is retracted, thereby allowing the self-expandable implant 100 to resilient deploy into its expanded configuration with the two expandable structures 10, 20 engaging the arterial walls, as shown in FIG. 18C. The guidewire GW and delivery catheter 201 are then withdrawn, leaving the implant anchored at the target location in the aortic arch with at least one expandable structure 100 engaged against and stretching the arterial walls at the target region for long-term reduction in blood pressure, as shown in FIG. 18D.

FIG. 19 shows an exemplary method of treating hypertension with an implant device. The method includes steps of: deploying an implant comprising one or more expandable structures, along a target region in the aortic arch defined as a narrow band wrapping the aorta between the LCCA and the LSA; stretching, with struts of the implants, an arterial wall along the target region by at least 20%, thereby inducing a baroreflex response; and exposing a majority of the target region being stretched to pulsatile blood flow through a major opening between the struts of the implant, thereby providing long term reduction in blood pressure. In some embodiments, the implant is configured to reshape the arterial wall, thereby inducing tension in the arterial walls to induce the baroreflex response.

FIG. 20 shows another exemplary method of treating hypertension by deploying an implant to the aortic arch. The method includes steps of: deploying an implant comprising two or more expandable structures, along a target region in the aortic arch, where at least one expandable structure engages the target region; stretching, with struts of the implants, an arterial wall along the aortic arch by at least 15%, typically by about 20%, thereby inducing a baroreflex response to reduce blood pressure; exposing a majority of the target region being stretched to pulsatile blood flow through a major opening between the struts of the implant, thereby providing long term reduction in blood pressure; and anchoring the implant in the target region long term with the two or more expandable structures, where the expandable structures are serially interconnected by axially expandable connectors to accommodate the curvature and complex geometry of the aortic arch, thereby providing long-term fixation. In some embodiments, the implant is configured to reshape the arterial wall, thereby inducing tension in the arterial walls to induce the baroreflex response.

FIGS. 21A-1 through 21C-3 show alternative designs of expandable structures each defined by one or more wires. Rather than pre-defined frames joined along lateral sides, such as those depicted in FIGS. 10A-13D, each expandable structure can be defined by one or more wires that define a design according to the required dimensions and properties of the implant. In some embodiments, the expandable structure can be formed of a single continuous wire that extends in a meandering, sinusoidal or zig-zag pattern to form a circumferential ring or band of the requisite dimensions to span the target region and exert sufficient outward force when expanded to stretch the arterial wall by the desired amount (e.g., about 20% or more). In some embodiments, the expandable structure is formed by two more wires defined in such a pattern to form a circumferential ring or band of the requisite dimensions and exert the required force. Typically, the wire is Nitinol and is set in a formed diameter that is sufficiently larger than the artery diameter so as to stretch the artery to a target diameter to ensure sufficient stretch of the baroreceptors. The gauge of the wire can be selected to ensure the force requirements are met and ensure longevity of the implant. It is noted that, in many such embodiments, the cross-sectional shape of these expandable structures is substantially circular such that the expandable structure uniformly increases the radius of the vessel wall, while the design still sufficiently exposes the arterial wall to pulsatile forces after deployment.

Three different designs (10A, 10B and 10C) of an expandable structure formed of a wire (e.g., Nitinol wire) are shown in FIGS. 21A-1 through 21C-3. FIGS. 21A-1 through 21C-1 show the structures at the formed diameter. FIGS. 21A-2 through 21C-2 show the structures at the vessel diameter. FIGS. 21A-3 through 21C-3 show the structures in a constrained configuration for delivery to the target location in the aorta. In the embodiments shown, the designs are configured and sized for deployment in the aortic arch. In some embodiments, where the aorta has a vessel diameter in the range of 20-25 mm the expandable structure can be configured such that the formed diameter is between 35-40 mm, typically about 38 mm, which studies have shown exerts sufficient force on simulated vessels of these diameters to effect a suitable stretch of the arterial wall (e.g., typically 20% or more). In these embodiments, the length 12 at the vessel diameter can range between 10-30 mm, typically 10-25 mm. In some embodiments, 10A has a length of about 23 mm, 10B has a length of about 17 mm and 10C has a length of about 14 mm at the vessel diameter. In the constrained configuration, the lengths are slightly longer due to foreshortening effects (e.g., 24 mm, 18 mm and 15 mm, respectively). In some embodiments, the wire diameter is between 0.2 to 1.5 mm, typically between 0.5 mm to 1 mm, more typically about 0.6 mm. In some embodiments, the expandable structures are designed to have a non-circular cross-section to facilitate reshaping of the arterial wall, thereby inducing tension in the arterial walls to induce the baroreflex response.

Studies were performed using the wire structure embodiments similar to those in FIGS. 21A-1 through 21C-3 to demonstrate viability of the implants in providing suitable stretch by increasing the diameter of the artery and/or reshaping the artery while still allowing sufficient compliance to maintain long term effect. These studies were done in a compliant 0.45 mm resin tube fabricated to mimic the compliance and structure of the arterial wall in the aortic arch. The results of the study are shown in FIG. 22. The compliance of the 0.45 mm resin tube was measured and documented. An exemplary expandable structure was placed into the same 0.45 mm resin tube, and the resulting compliance (dashed line) was plotted together with that of the empty tube (solid line). Both data sets were well fit by linear regression with a second order polynomial.

FIG. 22 demonstrates that the implant ring consistently stretches the resin tube, while preserving compliance. For example, at 50 mmHg pressure, the implant ring increases the diameter from 20 mm to about 23 mm, or 15% stretch. Similarly, at 200 mm Hg pressure, the implant ring increases the diameter from 25 mm to about 29 mm, or 16% stretch. The effects of the implant ring can also be interpreted in terms of pressure. For example, at 100 mmHg pressure, the empty tube (representing the native hypertensive vessel) has a diameter of about 21 mm. Placing the implant ring into this tube increases the diameter to about 24 mm, which corresponds to a pressure of 180 mmHg in the empty tube. In this scenario, the outward force of the implant ring is equivalent to +80 mmHg static pressure. In this example, the baroreceptor is stimulated by a stretch of 15%, or an equivalent pressure elevation of +80 mmHg. Therefore, it is hypothesized that the implant ring will trigger a baroreceptor response consistent with such an elevation in pressure, and consequently will decrease systemic pressure.

While it has been shown that acute stimulation of the baroreceptor reflex causes an immediate drop in systemic blood pressure, it has also been shown that a sustained response requires preservation of pulsatility. FIG. 22 also demonstrates that the pulsatility of the empty tube (native vessel analog) is preserved with the implant ring in place (implant ring treated vessel analog). This is evident because slopes of the compliance curves for the empty tube and implant ring tube are substantially parallel. For example, between 100 and 200 mmHg, the empty tube pulses between 21 and 25 mm (19%), while the same tube with an implant ring in place pulses between 24 and 29 mm (21%).

FIGS. 23A-23B illustrate another embodiment 120 that utilizes multiple expandable structures, 10, 20, 40, each of a wire design such as those in FIGS. 21A-21C, and which are interconnected by flexible connectors 30. In this embodiment, $D_V$ denotes the nominal vessel diameter. $D_A$ is the active segment diameter, which is greater than the $D_V$ so as to apply a desired stretch while the expandable structure design preserves pulsatility. $D_D$ and $D_P$ denote the expanded diameters of the distal and proximal expandable structures, respectively. Each of the $D_D$ maximum diameters and $D_P$ can be greater than or equal to $D_A$ to sufficiently engage the vasculature and prevent migration. In some embodiments, the proximal and distal expandable structure can have a flared design to provide resistance to migration. In some embodiments, the expandable structures can include barbs or gripping coatings for resisting migration. In some embodiments, the implant may be configured to affix after deployment (e.g., such as by adhesives or coatings) so as to allow repositioning during deployment. The flexible connectors or bridges connect the three expandable structures, each being able to axially elongated or compressed, thereby allowing flexibility to curve match the shape of the arch. For example, the flexible connectors allow more stretching/elongation at the outer radius and less stretching or even compression along the inner radius of the arch, as shown in FIG. 23B.

It is appreciated that these wire design expandable structures can also be utilized as the expandable structure of the implants in FIGS. 10-13 and can be similarly dimensioned. For example, the center structure can be dimensioned with a greater diameter than the proximal and distal structures, for example 1.2-1.5 times greater in diameter or largest lateral dimension than the proximal and distal structures. It is further appreciated that various flexible connector designs can be used. FIGS. 24A-24F depict various flexible connector designs that include one or more sinusoidal curves (as in FIG. 24A), V-shaped portions (FIGS. 24B-24D), zig-zag regions (FIG. 24E) or coiled structures (as in FIG. 24F) so as to allow axial expansion between adjacent rings or structures. While particular flexible connectors or bridges are depicted here, it is appreciated that any suitable flexible connectors could be used and that the bridge designs shown could be further extended to provide increased axial elongation to better accommodate the aortic arch.

VI. Alternative Implant Design and Deployment

As described in the previous embodiments, it has been assumed that the implant device utilizes a stimulus of circumferential stretch to activate the aortic baroreceptor nerves. However, it is appreciated that axial stretch may also be relevant and can be utilized to provide additional activation of baroreceptors. In some embodiments, the implant can be configured to stretch the arterial walls in an axial direction in addition to or instead of a lateral direction.

FIGS. 25-26 depict an implant device that is configured to stretch the arterial walls circumferentially/laterally and axially, thereby providing additional activation of the baroreceptors to further enhance the baroreflex response.

As shown in FIG. 25, the implant 121 can include differently configured expandable structures where the middle expandable structure 40 provides the circumferential (e.g., lateral) stretch described throughout the application, and the connectors 30 to the proximal and distal expandable structures 10, 20 are configured to provide axial stretch along the arterial walls. As in some previous embodiments, this design can be a three structure design with proximal and distal anchoring structures and a middle active structure deployed at the target region. In this design, the flexible connectors (i.e., bridges) connecting the proximal and distal structures 10, 20 to the middle active structure 40 are configured as axial springs, which are compressible so as to provide axially directed forces when deployed.

FIG. 26 shows sequential steps of deploying the implant of FIG. 25. In the first step, the distal structure 20 is deployed at a location distal of the target region. In the second step, the middle active structure 40 is deployed at the target region. However, as the middle structure 40 is deployed, the delivery catheter 200 is advanced distally to compress the axial springs between the distal structure 20 and middle structure 40, which axially loads the flexible connectors so as to provide an axially directed stretching force to the arterial wall between the distal structure and the middle structure 40. In the third step, as the proximal structure 10 is deployed the connectors 30 between the middle structure 40 and the proximal structure 10 are compressed by pushing the delivery catheter again during deployment, such that the compressed bridge connectors provide an additional axially directed stretching force from the middle structure 40 to the proximal structure 10. Accordingly, this approach can provide not only circumferential stretch at the target region by the deployed middle active structure, but also provides axial stretch from the target region in both proximal and distal directions, thereby providing enhanced baroreceptor activation or potentially equivalent baroreceptor activation at a reduced implant diameter. While a particular design is described here, it is appreciated that various other designs of the connectors and/or the proximal and distal expandable structures could provide axially directed stretching forces to provide enhance baroreceptor activation.

Accordingly, the implant devices and associated methods described herein address the unmet clinical need to treat patients with severe hypertension unresponsive to multiple pharmacologic agents. Existing conventional treatment and therapies (e.g., renal denervation, carotid artery devices) have had minimal or limited impact on this population due to their limited blood pressure lowering effect or risk of adverse events, respectively. The presently described implant is designed to fulfill this unmet clinical need based on historical and animal studies and identifying the unique anatomy and physiology of the aortic arch baroreceptors and the CT angiographic study outlined above. The implants described herein allow for sufficient stretching of a particular target region of the aortic arch which triggers highly sensitive baroreceptors, thereby consistently and reliably lowering blood pressure in the patient, while avoiding the adverse risks and drawbacks associated with conventional approaches targeting other vasculature, such as the carotid artery.

In another aspect, the implant can be configured to better accommodate the curvature of the aortic arch by using asymmetric expandable structures. As noted in FIG. 1C, the radius $r_1$ of the inner curvature of the arch is substantially less than the outer curvature $r_2$, which may cause inconsistent engagement and anchoring challenges for conventional stent structures. In previous embodiments, such as that in FIG. 1A, the implant used multiple structures to address these challenges. In these embodiments, the segments defining the length of each expandable structure are uniform around the circumference of the implant such that in order to accommodate the aortic arch curvature the gap between adjacent expandable structures is greater along the outside curvature as the inner curvature (see FIGS. 1A-1B). Accordingly, these configurations utilized connectors that were sufficiently flexible and extendable to accommodate this variable gap. In other embodiments, such as that in FIG. 1C, the implant can include one or more sections or expandable structures that are asymmetric, that is having a greater length along an outer radius of the aortic arch and a shorter length along the inner radius of the aortic arch, such as shown in the implant 140 in FIG. 1C. This provides a more consistent gap between structures, which simplifies the requirements of the connectors between expandable structures. For example, the connectors are not required to flex or stretch across a longer gap along the outer curvature and can be of a uniform length between expandable structure. This may be advantageous in that the smaller gap means that the aortic arch has more consistent, reliable contact along substantially the entire length of the implant, thereby providing an improved baroreflex response. It is appreciated that these aspects can be incorporated into any of the implants described herein.

FIGS. 27-33 show additional details of these latter embodiments having asymmetric expandable structures. In this exemplary implant, each expandable structure has a trapezoidal shape having a side of greater length along the outer curvature of the aortic arch and a shorter length along the other side for placement along the inner curvature of the aortic arch. As in previous embodiments, the implant can include one or more expandable structures that are interconnected by flexible connectors.

In the embodiment shown in FIG. 27, the implant 140 includes first, second and third expandable structures 10', 20', 40' that are interconnected by flexible connectors 30' of substantially the same length across a more uniform gap. As shown, each expandable structure is of a trapezoidal shape (from a side view) having a short side $L_1$ opposite a longer side $L_2$. FIG. 28 shows a side view of the implant in a constrained configuration. FIG. 29 shows the implant 140 in the constrained configuration but fully unwrapped. By this configuration, the expanded shape of the implant 140 conforms more closely to the natural shape of the arch. In some embodiments, the ratio of the long side to the short side is within the range of 2:1 to 3:1. In some embodiments, these expandable structure are formed by struts of lengths that vary between $L_1$ and $L_2$. The $L_1$ struts are intended to be located at the inner radius of the arch $r_1$ (indicated as the 0 degree position) and the longer $L_2$ struts are intended to be placed along the outer radius of the arch $r_2$ (indicated as the 180 degree position). Accordingly, this embodiment matches the expanded shape of the implant to the natural anatomical shape of the arch, thereby minimizing unintended forces or displacements to the anatomy. In this embodiment, the gap between the expandable structure is more uniform, reducing the magnitude and variation of stretch or compression required of the connectors. This reduces resulting mean and cyclic strains, and improves durability and longevity of the implant. In some embodiments, the implant can include markers thereon to aid in orienting the implant during delivery and placement in the aortic arch.

In another aspect, these implants can be defined in various cross-sectional shapes. In the embodiment in FIG. 30A, implant 140' has three asymmetrical expandable structures 10',20',40' which have cross-sections $P_1$, $P_0$, $P_1'$, where $P_0$ is placed at the apex of the arch and $P_1$ and $P_1'$ are placed proximal and distal from the apex. As shown in FIG. 30B, the cross-sections are all nominally circular. It is appreciated that the cross-sections could all be the same diameter or could be differing diameters (e.g. larger diameter at $P_0$, or increasing or decreasing diameters to accommodate the taper of the aortic arch). In the embodiment in FIG. 31A, implant 140" has three asymmetrical expandable structures 10", 20", 40" which have cross-sections $P_1$, $P_0$, $P_1'$, where $P_0$ is placed at the apex of the arch and $P_1$ and $P_1'$ are placed proximal and distal from the apex. As shown in FIG. 31B, the cross-sections are all non-circular, in particular, oval or ellipsoid in shape. In such embodiments, the orientation of a major axis of the oval/ellipsoid shape can be cranial/caudal, as shown in option 1 or medial/lateral, as shown in option 2. The ratio of major/minor axis may be uniform throughout the length or may be increased at the apex or decreased at the proximal or distal segments. It is appreciated that the cross-sections could all be the same dimension/orientations or could be differing diameters and/or orientations (e.g. larger diameter at P0, or increasing or decreasing diameters to accommodate the taper of the arch).

FIG. 32 shows another example of an implant 140 with three asymmetrical expandable structures, the implant being in a constrained configuration and having connectors 30 extending between the expandable structures. As can be seen, the length of the struts along the top side of the implant are longer than the length of the struts along the bottom side. FIG. 33 shows the implant 140 in a deployed configuration, where the three asymmetrical expandable structures 10, 20, 40 are expanded and the curvature of the overall implant to accommodate the arch is evident despite the connectors 30 being of the same or similar length. It is understood that these depictions are illustrative of the concept of the asymmetrical expandable structures and do not necessarily reflect the actual relative dimensions or geometry.

FIG. 34 depicts an example of a strut configuration 100a of an expandable structure for an implant, such as implant 100 in FIG. 1A, where the struts are of uniform lengths and widths around the circumference of each expanding boxcar segment. This approach provided consistent cell dimensions and mechanical properties, but produces a variable gap between expandable structures when deployed in the aortic arch, as described above.

FIG. 35 depicts an example of a strut configuration 140a of an expandable structure for an implant, such as implant 140 of FIG. 1C, where the struts are of variable length such that each expandable structure is asymmetric from a lateral side view. As shown, the expandable structure 10 includes shorter length struts $L_1$ and longer length struts $L_2$, thereby defining asymmetrical expandable structure that better accommodate the curvature of the aortic arch. By utilizing struts of variable length, this produces an asymmetric arch-conforming shape upon expansion. It is understood that in the art of stent design that struts can be approximated as simple beams considering a beam fixed at one end and free but guided at the other, deflection can be related to strain and force by standard force and strain equations (strut parameters are width (w), length (L) and thickness (t), which is constant) and table below of exemplary strut dimensions.

$$\text{Strain} \qquad \varepsilon \propto \frac{w}{L^2}$$

$$\text{Force} \quad F \propto \frac{t \cdot w^3}{L^3} \propto \frac{w^3}{L^3}$$

TABLE 4

| Exemplary Strut Dimensions (Length L and Width W) | | | | | |
|---|---|---|---|---|---|
| L | W | $\alpha\varepsilon$ | L | w | $\alpha F$ |
| 10 | 1 | $1/100$ | 10 | 1 | $1/1000$ |
| 20 | 1 | $1/400$ | 20 | 1 | $1/8000$ |
| 30 | 1 | $1/900$ | 30 | 1 | $1/27000$ |
| 10 | 1 | $1/100$ | 10 | 1 | $1/1000$ |
| 20 | 4 | $1/100$ | 20 | 2 | $1/1000$ |
| 30 | 9 | $1/100$ | 30 | 3 | $1/1000$ |

As previously described, in some embodiments, the apex conforming shape most preferably is composed of struts of variable length, with the longest struts (at the apex of the arch), typically about 2-3 times longer than the shortest struts. The top three rows of Table 4 estimates the maximum strain for struts of length 10, 20 and 30 mm all with equal width l=1 mm. Strain varies by a factor of 4 when length doubles, or by a factor of 9 when strut width triples. Force varies by a factor of 8 to 27. The bottom three rows of Table 4 estimates the preferred variable strut widths necessary to compensate for strut length variations of 2-3 times. Preferably, in some embodiments, the asymmetrical expandable structure are defined by struts of variable lengths, with the longest struts preferably 2-3 times the length of the shortest strut, with intermediate struts having intermediate lengths. It is appreciated that these dimensions are exemplary and that various other dimension/ratios could be utilized.

FIGS. 36A-36C depict another exemplary implant, a single implant that spans across a substantial portion of the aortic arch, such as implant 150 shown in FIG. 1D. This implant is designed with a non-circular cross-sectional shape so as to change a shape of the aortic arch when deployed within. FIGS. 36A-36B shows the implant design 150a as a stent-like braided or braided expandable structure designed with a non-circular cross section when expanded, although the structure typically includes fewer braids/struts and larger openings, typically 30%, 40%, 50%, 60%, 70% fewer struts or less. As shown in FIG. 36A, the braided structure is sufficiently flexible in a lateral direction to accommodate the curvature of the aortic arch. As shown in FIG. 36B, the non-circular cross section 151 is elliptical. The implant can be formed of one or more wires that are braided such that the wires extend helically, which allows for greater lateral flexibility. FIG. 36C shows another implant design 150b that is formed as a laser-cut tube, the struts configured so that when deployed the implant forms the non-circular cross section 151 that is elliptical. In some embodiments, the implant can optionally include one or more coupling/release features 152 at one or both ends to facilitate delivery and deployment of the implant. Such features can include loops, cut-out portions, or any of those described herein.

In these embodiments, the implant 150 is at least 60 mm in length, typically about 70-90 mm, such that the implant extends along a majority of the aortic arch along the target zone, thereby activating multiple regions of baroreceptors and providing a more consistent, robust response. Moreover, by relying on engagement of the device along a majority of the aorta, the anchoring forces of the implant are distributed over a larger area avoiding the need for separate anchoring structures or features, thereby minimizing trauma to the arterial walls, which can reduce inflammation and formation of thrombus that can contribute to formation of atherosclerotic plaques.

It is understood that these concepts can be utilized in various other shapes/designs, the non-circular cross-section could be other non-circular shapes as well, including but not limited to: triangular, square, rectangular, or any regular polygonal shape.

In another aspect, the implant is sized specifically for the dimensions of the human aortic arch so as to engage the arterial walls with the structure so as to anchor the implant within the aortic arch and sufficiently engage the arterial walls within the target zone. Preferably, the target zone is sufficiently large to include multiple target regions or locations rich in sensitive baroreceptors, including the cylindrical band wrapping the aorta across and adjacent the LSA, as noted previously. Thus, engagement with a non-circular cross-section of a braided implant tensions the arterial wall and stimulates the highly sensitive baroreceptors in this region.

FIGS. 42A-42B shown an exemplary implant of an expandable implant 150 formed by woven or braided wire. The device has an elliptical cross-section 151 when expanded, as shown in FIG. 42A, and having a greatest diameter D of a suitable dimension to reshape the aorta. In some embodiments, D can be 30 mm or greater, typically 40-60 mm. The length (1) is a suitable length to extend along a majority of the aorta to cover the entire target zone. In some embodiments, length/is 60 mm or greater, typically 70-90 mm. As shown in FIG. 42B, the braided structure is designed to include interstitial spaces 153 having an area larger than those in a conventional stent, such as an area A of 9 mm² or greater (about 9-30 mm²). The implant can also include one or more markers 152 at proximal and/or distal ends to aid in placement along the target zone.

FIGS. 43A-43B show alternative implant designs. In FIG. 43A, the implant 160 includes two or more spines 164 that extend along a length and are spaced apart by lateral struts, creating a large open space 165 therebetween to expose the arterial walls to blood flow. The spines engage the arterial walls so as to reshape the arterial walls to an asymmetric, non-circular cross-sectional shape 161, thereby tensioning the walls along the target zone to induce the baroreflex response. This implant design can include the various other aspects and dimensions noted previously, including the marker 162 at proximal and/or distal ends. In FIG. 43B, the implant 170 includes a single coil wire that assumes a non-circular cross-sectional shape 171 when expanded. This implant design can include the various other aspects and dimensions noted previously, including the marker 172 at proximal and/or distal ends. These two designs have the benefit of having much larger side openings or open spaces to allow lateral blood flow and expose the arterial walls to pulsatile flow. It is appreciated that the concepts described herein are not limited to these designs and the implant could be of any design that engages the arterials walls to reshape the aorta to assume a non-circular cross-sectional shape, thereby tensioning the walls to induce the baroreflex response.

28

VII. Sizing of Implant for Aortic Arch for Reshaping

The baroreceptor amplification device is an endovascular implant designed to amplify the baroreflex response by stimulation of highly sensitive baroreceptors in a precise location within the aorta. This is accomplished by appropriately sizing the implant as described herein to achieve sufficient engagement to reshape (e.g., at least 5%, 10%, 15% or more) of the arterial wall within the target region. The implant is dimensioned based on the unique morphology of the aortic arch in humans. In some embodiments, the applicable dimension suitable for such an implant have been determined by a computed tomography angiographic (CTA) study of human aortas. Measurements of the aortic arch CTA were obtained from 50 patients, including both men and women between the ages of 53 and 88. The measurements were tabulated and the means and range were determined per Tables 1 and 2 shown previously.

In one aspect, the diameter and length dimensions could be considered to display relatively little variation as demonstrated by the small standard deviations and narrow ranges. As shown in FIG. 39, the aortic arch region has multiple distinct regions where portions of an implant device may potentially be implanted or anchored by one or more portions of the implantable device. Thus, the implant device design should accommodate the entire target zone. Thus, it is considered that an appropriately sized implant could be made to fit most patients within the above noted ranges. In the alternative, it could be considered that these means and ranges of dimension warrant differing sizes of implants. In some embodiments, a set of differently sized implants (e.g., 3-10 different sizes) could be provided and a size could be readily selected based on the particular measurements of the aortic arch of a given patient. In another alternative, an implant could be custom-made according to the unique measurement of a patient. The latter two options may be well suited for patients with highly variable morphology or particularly complex geometry of the aortic arch.

VIII. Mechanism of Action of Wall Tension

To further understand the sizing of the implant, the mechanism of action by which the implant reduces blood pressure should be understood. It is helpful to consider the aortic arch as a circle in cross-section and to consider the arterial wall in discrete arc lengths, as determined by the figure and the arc length formula.

As noted previously, the conventional approach to baroreceptor stimulation by an intravascular implant had assumed stretching of the arterial wall achieved activation of the baroreceptors. Studies indicated that a narrow cylindrical region of the aorta across from the LSA is rich in baroreceptors such that stretching of this region would necessarily activate baroreceptors and achieve a predictable and appreciable drop in blood pressure.

However, animal studies (using dogs, which generally share this same arrangement of baroreceptors in the aorta as humans) indicated variable results. Experimental studies shows that all of three dog subjects responded to the aortic pinch maneuver along the aortic arch. The maximum drop in systolic blood pressure averaged 18 mm Hg. Although surprisingly, the aortic arch trigger locations varied significantly between the three dogs. The aortic pinch maneuver was performed on each of the dogs at locations, A, B, C on the aortic arch, as shown in FIG. 37. Dog 1 shows the response at only location B. Dog 2 showed the response only at location C. Dog 3 shows the response at all of locations A, B, C. FIG. 38A shows one of the recordings of the typical blood pressure at top, and the recordings of blood pressure during the pinch maneuver at bottom, which illustrates the drop in blood pressure between the points at which the artery is pinched on and off (indicated by arrows). FIGS. 38B-38C illustrate the change in curvature resulting from the pinch maneuver in dog 3 at position B. The ultrasound panels in FIG. 38B represent the baseline curvature, and panels in FIG. 38C represent curvature during the pinch maneuver. Each panel represents a frame (time sample) from the ultrasound recording. Within each frame, the points represent the curvature around the circumference of the vessel, with circumferential position represented by degrees, and curvature expressed in units of 1/mm. Note that in the baseline condition, the mean curvature is about 0.1 (1/mm), with maximum curvature around 0.2 (1/mm); these values correspond to an average radius of 10 mm (or average diameter of 20 mm), and a minimum local radius of about 5 mm (or equivalent minimum local diameter of about 10 mm). Contrast this with the panels in FIG. 38C, showing a mean curvature around 0.2 (1/mm) for an equivalent diameter of 5 mm), and maximum curvature of about 0.4 (1/mm), equivalent to a minimum local radius of 2.5 mm (equivalent to a minimum local diameter of 5 mm). These experimental observations suggest that a shape change which doubles the local curvature (or halves the effective local radius of curvature) is sufficient to elicit the desired baroreceptor response.

FIGS. 39-40 show the distribution of aortic arch baroreceptors from human histology studies. In FIG. 39, the shaded region is the target zone along a majority of the aortic arch that seems to encompass all the potential areas of potential baroreceptor activation. The target zone extends from proximal the LCC to distal the LSA. FIG. 40 shows the nerve count in the various regions showing the higher concentrations in the zone extending along D E and F.

FIGS. 41A-41B show ultrasound images of the aorta during the aortic pinch maneuver. FIG. 41A shows the baseline aortic arch shape, which is generally circular with radius R, and FIG. 41B shows the aortic arch shape while being pinched with radius R' greater than radius R. As shown, the pinch maneuver clearly deforms the geometry of the aortic arch baroreceptor site and increases the radius of curvature, thereby increasing wall tension in the aortic arch.

FIGS. 44A-44B shows the distribution of baroreceptors at one location of the aortic arch found to be rich in baroreceptors. FIG. 44A is a depiction of the aortic arch with the baroreceptor tissue (shown in red). FIG. 44B is a cross-section that shows (in black) the distribution of baroreceptors around the circumference of the aortic arch. At top, the baroreceptor nerve fiber is shown.

FIG. 45 shows the role of the ion channel in baroreceptor activation. The baroreceptor sensor is a mechano-sensitive ion channel (termed Piezo) at the terminus of a nerve fiber that connects the aorta to the brain stem. When the ion channel opens or is triggered, the nerve depolarizes sending a signal to the brain stem to lower blood pressure.

FIG. 46 shows the baroreceptor ion channels (ic) in the aortic artery wall, specifically within the adventitia (a) layer.

FIG. 47 depicts the conventional theory behind stretch of the arterial wall to activate the baroreflex response. It has been commonly thought that stretching of the arterial wall separated or opened the ion channels, such that an implant that stretched the artery wall would open most of the ion channels and result in a robust baroreflex response.

Thus, triggering of the baroreceptor has conventionally been described as a response to "stretching" the arterial wall and baroreceptors are commonly called "stretch receptors." Hence, discrete areas rich in baroreceptors have been targeted to be stretched by expandable intravascular implants.

Various conventional implants, such as those by Vascular Dynamics, are sized and dimensioned specifically to stretch a discrete targeted portion of an intravascular implant. However, recent studies have shown that wall tension rather than stretching results in activation of the baroreceptors. The strain equation is $\Delta\in=p\times\Delta 2r/tE$, where E is wall strain, p is pressure inside the artery, r is the radius of the artery (i.e. carotid bulb), and E is Young's modulus. The r variable is the only variable that can be manipulated by the clinician or the implant. This manipulation is explored by the "pinch" maneuver described above, where the clinician manually pinches the exposed artery between two fingers such that the circular artery assumes an elliptical shape, where the vertex of the ellipse increased in radius and the sides of the ellipse that reduce in radius and under increased wall tension. Similarly, deployment of the barostent implant in the native aorta deforms the aorta, as shown in FIG. 48A. The artery A is deformed from a circular shape to an elliptical shape having areas A of increased curvature and areas B of decreased curvature (barostent implant not shown). Studies have shown that the areas B under increased tension result in greater activation of the baroreceptors (even absent any apparent stretch). By this approach, the barostent implant converts a surgical method of baroreceptor triggering into an endovascular technique for sustained baroreceptor amplification. In some embodiments, the implant can be woven or braided implant and designed to have more braids along the greater axis of the ellipse and fewer braids along minor axis of the ellipse reshape the aorta and minimize the metal in the region of the aorta that needs to be most pulsatile. In some embodiments, the implant can be laser cut from a tube in a design that provides the desired non-circular cross-sectional shape. FIGS. 48B-48C illustrate the aorta wall before and after tensioning with an element of the implant. FIG. 48B depicts a segment of the aortic wall in which there is known to be a gradient of tension through the thickness of the wall and wall stress (i.e. tension) is further influenced by hydrostatic pressure P. FIG. 48C depicts the same segment with a shape changing deformation induced by contact with an element (e.g. strut, wire or similar feature) of the implant, in accordance with some embodiments, imparting a radially outward force F. This localized deformation alters the stretch and tension differently at the inner surface versus the outer surface of the wall. Therefore $T_1'>T_1$, $T_2'>T_2$ and $(T_2'-T_1')\neq(T_2-T_1)$. In some embodiments, the implant may be designed to impart a force F causing a local deformation of the aorta to induce $T_2'$ or $T_1'$ corresponding to a localized stretch of greater than or equal to 20%.

It is known that ion channels are required for baroreception and that these ion channels mediate the neuronal sensing of blood pressure that produce the baroreceptor reflex response. Baroreception is initiated by ion channels (e.g. PIEZO proteins) located in the membrane wall at the terminus of the baroreceptor nerve cell fiber. (see Zeng et al., Science 362, 464-467 (2018)). While baroreceptors have long been known as "stretch receptors", the role of stretch and tension in activating Piczol ion channels has been the subject of previous research studies, which found piezo ion channels activate in response to cellular membrane tension. (see Lewis and Grandl. eLife 4: e12088, 2015.) Thus, baroreceptors have long been mischaracterized as "stretch" receptors, when in fact they are "tension" receptors. Research has found that tension from changes in membrane curvature was the activating stimulus and further that sustained modulation resulted in inactivation suggesting that continuous modulation of the membrane was needed for continued activation. In regard to membrane curvature, it was found that activation occurred where the curvature was flattest. This suggest the clinical response observed during the "pinch" maneuver to be activation of the ion channels of the baroreceptors along the flattened portions on the sides of the elliptical shaped vessel. The relationship between wall tension, pressure and radius is explained by LaPlace's Law, $T=R \times P$, where T is wall tension, R is radius and P is arterial pressure.

LaPlace's Law holds for elastic vessels, elastin-rich segments of the aortic arch are innervated by the baroreceptor nerve cell fibers (see Bergewerff 1999). The histologies shown in FIG. 7 show the presence of these nerve cell fibers are shown in the histology from regions B and C of the aortic arch. Eliminating elasticity diminishes the wall tension in the baroreceptor artery wall; in short, baroreceptor ion channels will not depolarize in the absent of an increase in wall tension. Historically this phenomenon has been demonstrated by 1) applying a rigid cast around the baroreceptor artery, 2) equalizing the pressure inside and outside of the baroreceptor artery wall, and 3) overstretching the artery wall with an endovascular frame. In each case baroreceptor signaling terminates. Past studies showed that baroreceptor signal was eliminated by application of a plaster cast around the carotid sinus (see Hauss 1948) and eliminated by equalization of intra-arterial and extra-mural pressures (James, J. Physiol. 214:89-103 (1971)).

Accordingly, in view of the apparent mechanisms of action of the baroreflex response described above, the barostent implant described herein seeks to achieve three objectives: i) change the cross-sectional geometry of the aortic arch in order to create wall tension therein, ii) preserve the elastic nature of the aortic arch tissue; and iii) preserve the aortic arch curvature (i.e. avoid elongating or straightening the arch).

In yet another aspect, the implant device is especially suited for intravascular delivery and deployment since the implant has a collapsed configuration for advancement through the vasculature and an expanded configuration for engaging the arterial walls, as shown in the embodiments of FIGS. 1A-1D. In the collapsed configuration, the implant is disposed in a delivery catheter to facilitate intravascular delivery to the target site at the aortic arch and subsequent deployment.

In an exemplary embodiment, the implant is a self-expandable structure that is preloaded into a sheathed delivery catheter, as shown in FIG. 49. As shown, the intravascular delivery catheter 400 is designed to deliver the implant 150 in the collapsed configuration, and to position and deploy the implant along the target zone within the aortic arch, as shown in FIGS. 1A-1D and 39. The delivery catheter includes an internal guidewire lumen so that it can be advanced along a guidewire GW positioned in the aortic arch. In the embodiment shown, the delivery catheter 200 includes a catheter shaft 201 on which the implant 150 is collapsed, and over which is disposed a retractable sheath 202 that constrains the implant in the collapsed configuration until the implant is positioned at the desired target zone, for example by visualization of a marker (e.g., radiopaque or ultrasound marker). In some embodiments, the connectors may be made from a differing material than the frames so that the connectors themselves are distinctly visible through visualization techniques. The delivery catheter can further include a distal tip 203 to guide advancement over the GW and a flush port 211 for flushing before, during or after delivery. The delivery catheter includes a handle 210 by which the clinician can retract the sheath to deploy the self-expanding implant. Typically, the overall length (l) of the delivery catheter is between 100-150 cm (e.g., about 135 cm) so as to readily access the aortic arch by insertion of the catheter through the femoral artery.

In some embodiments, the delivery catheter can be configured to deliver the entire implant upon retraction of the sheath. The length of the expandable structure is sufficient such that the expandable structure is deployed at the target zone despite any minor axial movement upon deployment. In some embodiments, the catheter may include incremental retraction to deliver the implant in a precise controlled manner. In still other embodiments, the implant may be balloon expandable and disposed in a collapsed configuration on a balloon of the delivery catheter, the balloon suitably dimensioned for expansion in the aorta to expand and deploy the implant in the target region.

In an exemplary delivery method, a guidewire GW is advanced through an entry point (e.g., the femoral artery) and advanced through the vasculature and into the aortic arch. Visualization techniques, such as fluoroscopy, can verify placement of the GW in the target region. The delivery catheter 200 is advanced along the GW, the catheter having an implant 100 disposed in a collapsed configuration on a catheter shaft 201 and constrained within a retractable outer sheath 202. Once the implant is positioned at the desired target location within the aortic arch, the outer sheath 202 is retracted, thereby allowing the self-expandable implant 100 to resilient deploy into its expanded configuration engaging the arterial walls. The guidewire GW and delivery catheter 201 are withdrawn, leaving the implant anchored at the target zone in the aortic arch for long-term reduction in blood pressure.

FIG. 50 pertains to a method of treating hypertension. The method includes steps of: deploying an implant within an aortic arch of the patient, the implant having a collapsed configuration for advancement through a vasculature of the patient and an expanded configuration for engagement of an arterial wall within an aortic arch of the patient; engaging the arterial wall with the implant in the expanded configuration along a target zone that extends at least between the brachiocephalic artery takeoff and the left subclavian artery takeoff, wherein the implant has a non-circular cross-section when expanded thereby inducing wall tension along the target zone in the aortic arch by reshaping; and exposing a majority of the arterial wall along the target zone to pulsatile blood flow side openings of the implant so as to sustain the baroreflex response induced by the implant long-term In the foregoing specification, the invention is described with reference to specific embodiments thereof, but those skilled in the art will recognize that the invention is not limited thereto. Various features, embodiments and aspects of the above-described invention can be used individually or jointly. Further, the invention can be utilized in any number of environments and applications beyond those described herein without departing from the broader spirit and scope of the specification. The specification and drawings are, accordingly, to be regarded as illustrative rather than restrictive. It will be recognized that the terms "comprising," "including," and "having," as used herein, are specifically intended to be read as open-ended terms of art. It is appreciated that various dimensions of embodiments described herein and that, in some embodiments, a respective dimension could encompass variations, such as within +/−25% or within +/−10% of the recited value. Unless stated otherwise, the term "about" is considered to mean within +/−10%. Any references to publication, patents, or patent applications are incorporated herein by reference in their entirety for all purposes.

What is claimed is:

1. A method for treating hypertension in a patient, said method comprising:

deploying an implant within an aortic arch of the patient, the implant having a collapsed configuration for advancement through a vasculature of the patient and an expanded configuration for engagement of an arterial wall within the aortic arch of the patient, the implant having a length of at least 60 mm when deployed;

engaging the arterial wall with the implant in the expanded configuration along a target zone that includes a region that extends at least between a brachiocephalic artery takeoff and a left subclavian artery takeoff, wherein the implant has a non-circular cross-section when expanded thereby inducing wall tension along the target zone in the aortic arch;

exposing a majority of the arterial wall along the target zone to pulsatile blood flow via side openings of the implant so as to induce a long term baroreflex response;

wherein the implant is woven or braided from one or more wires; and wherein, in the expanded configuration, the side openings each having an area of 9 mm² or greater to allow blood flow therethrough to any lateral arteries in the aortic arch and to expose arterial walls to pulsatile blood flow.

2. The method of claim 1, wherein the non-circular cross-section is elliptical.

3. The method of claim 1, wherein the non-circular cross-section is a regular polygonal shape.

4. The method of claim 1, wherein the non-circular cross-section is constant along an entire length of the implant.

5. The method of claim 1, wherein the length when deployed is between 60-100 mm.

6. The method of claim 5, wherein the implant is dimensioned so that a greatest lateral dimension is greater than 25 mm.

7. The method of claim 1, wherein the implant is self-expandable.

8. The method of claim 1, wherein the one or more wires are Nitinol.

9. A method for treating hypertension in a patient, said method comprising:

deploying an implant within an aortic arch of the patient, the implant having a collapsed configuration for advancement through a vasculature of the patient and an expanded configuration for engagement of an arterial wall within the aortic arch of the patient, the implant having a length of at least 60 mm when deployed;

engaging the arterial wall with the implant in the expanded configuration along a target zone that includes a region that extends at least between a brachiocephalic artery takeoff and a left subclavian artery takeoff, wherein the implant has a non-circular cross-section when in the expanded configuration thereby inducing an increased wall tension along the target zone in the aortic arch and, wherein the implant includes expandable structure segments connected serially by multiple flexible connectors to allow the expandable structure segments to extend axially along a curvature of the aortic arch, and wherein, when the implant is deployed, the expandable structure segments positioned at a proximal end and a distal end of the implant have a diameter greater than a diameter of an expandable structure segment located at a mid-section of the implant to thereby prevent migration of the implant; and exposing a majority of the arterial wall along the target zone to pulsatile blood flow via side openings of the expandable structure segments in order to induce a long term baroreflex response.

10. A method for treating hypertension in a patient, said method comprising:

deploying an implant within an aortic arch of the patient, the implant having a collapsed configuration for advancement through a vasculature of the patient and an expanded configuration for engagement of an arterial wall within the aortic arch of the patient, the implant having a length of at least 60 mm;

engaging the arterial wall with the implant in the expanded configuration along a target zone that corresponds to an area of baroreceptor nerves and includes a region that extends at least between a brachiocephalic artery takeoff and a left subclavian artery takeoff, wherein the implant has a non-circular cross-section when in the expanded configuration thereby inducing increased wall tension along the target zone in the aortic arch;

exposing a majority of the arterial wall along the target zone to pulsatile blood flow via side openings of the implant in order to induce a long term baroreflex response; and wherein the implant includes a middle expandable structure is that at the target location to activate the baroreceptor nerves, and wherein the implant further includes a proximal expandable anchor and a distal expandable anchor to secure the middle structure in the target zone.

* * * * *